US006380369B1

(12) United States Patent
Adams et al.

(10) Patent No.: US 6,380,369 B1
(45) Date of Patent: Apr. 30, 2002

(54) HUMAN DNA MISMATCH REPAIR PROTEINS

(75) Inventors: Mark D. Adams, North Potomac; Robert D. Fleischmann, Gaithersburg; Claire M. Fraser, Potomac; Rebecca A. Fuldner, Barnesville; Ewen F. Kirkness, Olney, all of MD (US); William A. Haseltine, Washington, DC (US); Craig A. Rosen, Laytonsville, MD (US); Steve Ruben, Olney, MD (US); Ying-Fei Wei, Darnestown, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 08/294,312

(22) Filed: Aug. 23, 1994

Related U.S. Application Data

(63) Continuation-in-part of application No. 08/210,143, filed on Mar. 16, 1994, which is a continuation-in-part of application No. 08/187,757, filed on Jan. 27, 1994.

(51) Int. Cl.$^7$ ............................ C07H 21/02; C22Q 1/68
(52) U.S. Cl. ............................ 536/23.1; 435/6
(58) Field of Search .............................. 536/23.1, 23.2, 536/23.5, 24.31

(56) References Cited

U.S. PATENT DOCUMENTS

| | | | | |
|---|---|---|---|---|
| 4,737,454 A | * | 4/1988 | Dattagupta et al. | ............ 435/6 |
| 5,124,443 A | | 6/1992 | Colella et al. | |
| 5,922,855 A | | 7/1999 | Liskay et al. | |
| 6,165,713 A | | 12/2000 | Liskay et al. | |
| 6,191,268 B1 | * | 2/2001 | Liskay et al. | ................ 435/6 |

FOREIGN PATENT DOCUMENTS

| | | |
|---|---|---|
| WO | 95/14772 | 11/1993 |
| WO | WO 95/14085 | 11/1994 |
| WO | WO 95/16793 | 12/1994 |
| WO | 95/14085 A2 | 5/1995 |
| WO | WO 95/14085 | 5/1995 |
| WO | 95/15381 A2 | 6/1995 |
| WO | WO 95/15381 | 6/1995 |
| WO | 95/16793 A1 | 6/1995 |

OTHER PUBLICATIONS

U.S. application No. 08/352,902, Liskay et al., filed Dec. 9, 1994.
U.S. application No. 08/209,521, Liskay et al., filed Mar. 8, 1994.
U.S. application No. 08/168,877, Liskay et al., filed Dec. 17, 1993.
Prolla, et al., *Molecular and Cellular Biology* vol. 14, No. 1, p. 407–415 (Jan. 1994).
Papadopoulos, et al., *Science*, vol. 263, p. 1625–1629 (Mar. 1994).
U.S. application No. 08/154,792, Kolodner et al., filed Nov. 17, 1993.
U.S. application No. 08/163,449, Kolodner et al., filed Dec. 7, 1993.
U.S. application No. 08/259,310, Kolodner et al., Feb. 22, 1995.
U.S. application No. 08/352,902, Liskay et al., filed Dec. 9, 1994.
U.S. application No. 08/209,521, Liskay et al., filed Mar. 8, 1994.
U.S. application No. 08/168,877, Liskay et al., filed Dec. 17, 1993.
GenBank Accession No. D12046, (Dec. 2, 1992).
GenBank Accession No. Z24775, (Aug. 2, 1993).
GenBank Accession No. Z36291, (Aug. 15, 1994).
Bronner et al., Mutation in the DNA mismatch repair gene homologue hMLH 1 is associated with the hereditary non–polyposis colon cancer, *Nature*, 368:258–261 (1994).
Chauhan et al., Proficiency of Mismatch Repair Activity can be Retained in spite of low expression levels of the hMLH–1 gene in the HCT 116 colon cancer cell line, *Gastroenterology*, Suppl. 110:A502 (1996).
Dorland's Medical Dictionary, p. 232 (1995).
Fishel et al., The Human Mutator Gene Homologue MSH2 and Its Association With Hereditary Nonpolyposis Colon Cancer, *Cell*, 75:1027–1038 (1993).
Goldberg et al., Models of Neoplasia and Their Diagnostic Implications: A Historical Perspective, *Clin. Chem.*, 39(11B):2360–2374 (1993).
Green et al., Systematic Generation of Sequence–Tagged Sites for Physical Mapping of Human Chromosomes: Application to the Mapping of Human Chromosome 7 Using Yeast Artificial Chromosomes, *Genomics*, 11:548–564 (1991).
Horii et al., Cloning, Characterization and Chromosomal Assignment of the Human Genes Homologous to Yeast PMS1, A Member of Mismatch Repair Genes, *Biochemical and Biophysical Research Communications*, 204; 1257–1264 (1994).

(List continued on next page.)

*Primary Examiner*—Eggerton A. Campbell
(74) *Attorney, Agent, or Firm*—Human Genome Sciences, Inc.

(57) ABSTRACT

The present invention discloses three human DNA repair proteins and DNA (RNA) encoding such proteins. The DNA repair proteins which may be produced by recombinant DNA techniques. One of the human DNA repair proteins, hMLH1, has been mapped to chromosome 3 while hMLH2 has been mapped to chromosome 2 and hMLH3 has been mapped to chromosome 7. The polynucleotide sequences of the DNA repair proteins may be used for diagnosis of a hereditary susceptibility to cancer.

62 Claims, 26 Drawing Sheets

OTHER PUBLICATIONS

Jacoby et al., Genetic instability associated with adenoma to carcinoma progression in hereditary nonpolyposis colon cancer, *Gastroenterology*, 109(1) 73–82 (1995).

Kramer et al., Cloning and Nucleotide Sequence of DNA Mismatch Repair Gene PMS1 from *Saccharomyces cerevisiae*: Homology of PMS1 to Procaryotic MutL and HexB, *J. of Bacteriology*, 171:5339–5356, (1989).

Leach F. S. et al., Mutations of a mutS Homolog in Hereditary Nonpolyposis Colorectal Cancer, *Cell*, 75:1215–1225 (1993).

Lindblom et al., Genetic mapping of a second locus predisposing to hereditary non–polyposis colon cancer, *Nature Genetics*, 5:279–282 (1993).

New et al., The yeast gene MSH3 defines a new class of eukaryotic MutS homologues, *Mol. Gen. Gent.* 239:97–108 (1993).

Nicolaides et al., Mutations of two PMS homologues in hereditary Nonpolyposis colon–cancer, *Nature*, 371:75–80 (1994).

Nyström–Lahti, Mismatch Repair Genes on Chromosomes 2p and 3p Account for a Major Share of Hereditary Nonpolyposis Colorectal Cancer Families Evaluable by Linkage, *American Journal of Human Genes*, 55:659–665 (1994).

Okubo et al., Large Scale cDNA sequencing for analysis of quantitative and qualitative aspects of gene expression, *Nature Genetics*, 2:173–179 (1992).

Prolla et al., MLH1, PMS1, and MSH2 Interactions During the Initiation of DNA Mismatch in Repair Yeast, *Science*, 265: 1091–1093 (1994).

Radman et al., DNA Mismatch Repair Systems: Mechanisms and Applications in Biotechnology, *Biotechnology and Genetic Engineering Reviews*, 11:357–366 (1993).

\* cited by examiner

Polynucleotide and deduced amino acid sequence of hMLH1

```
-40                 -20                  1
  .         .         .         .         .         .
GTTGAACATCTAGACGTTTCCTTGGCTCTTCTGGCGCCAAAATGTCGTTCGTGGCAGGGG
+---------+---------+---------+---------+---------+---------
CAACTTGTAGATCTGCAAAGGAACCGAGAAGACCGCGGTTTTACAGCAAGCACCGTCCCC
                                            M   S   F   V   A   G   V
 20                  40                  60
  .         .         .         .         .         .
TTATTCGGCGGCTGGACGAGACAGTGGTGAACCGCATCGCGGCGGGGGAAGTTATCCAGC
+---------+---------+---------+---------+---------+---------
AATAAGCCGCCGACCTGCTCTGTCACCACTTGGCGTAGCGCCGCCCCCTTCAATAGGTCG
   I   R   R   L   D   E   T   V   V   N   R   I   A   A   G   E   V   I   Q   R
 80                 100                 120
  .         .         .         .         .         .
GGCCAGCTAATGCTATCAAAGAGATGATTGAGAACTGTTTAGATGCAAAATCCACAAGTA
+---------+---------+---------+---------+---------+---------
CCGGTCGATTACGATAGTTTCTCTACTAACTCTTGACAAATCTACGTTTTAGGTGTTCAT
   P   A   N   A   I   K   E   M   I   E   N   C   L   D   A   K   S   T   S   I
140                 160                 180
  .         .         .         .         .         .
TTCAAGTGATTGTTAAAGAGGGAGGCCTGAAGTTGATTCAGATCCAAGACAATGGCACCG
+---------+---------+---------+---------+---------+---------
AAGTTCACTAACAATTTCTCCCTCCGGACTTCAACTAAGTCTAGGTTCTGTTACCGTGGC
   Q   V   I   V   K   E   G   G   L   K   L   I   Q   I   Q   D   N   G   T   G
200                 220                 240
  .         .         .         .         .         .
GGATCAGGAAAGAAGATCTGGATATTGTATGTGAAAGGTTCACTACTAGTAAACTGCAGT
+---------+---------+---------+---------+---------+---------
CCTAGTCCTTTCTTCTAGACCTATAACATACACTTTCCAAGTGATGATCATTTGACGTCA
   I   R   K   E   D   L   D   I   V   C   E   R   F   T   T   S   K   L   Q   S
260                 280                 300
  .         .         .         .         .         .
CCTTTGAGGATTTAGCCAGTATTTCTACCTATGGCTTTCGAGGTGAGGCTTTGGCCAGCA
+---------+---------+---------+---------+---------+---------
GGAAACTCCTAAATCGGTCATAAAGATGGATACCGAAAGCTCCACTCCGAAACCGGTCGT
   F   E   D   L   A   S   I   S   T   Y   G   F   R   G   E   A   L   A   S   I
320                 340                 360
  .         .         .         .         .         .
TAAGCCATGTGGCTCATGTTACTATTACAACGAAAACAGCTGATGGAAAGTGTGCATACA
+---------+---------+---------+---------+---------+---------
ATTCGGTACACCGAGTACAATGATAATGTTGCTTTTGTCGACTACCTTTCACACGTATGT
   S   H   V   A   H   V   T   I   T   T   K   T   A   D   G   K   C   A   Y   R
```

FIG. 1A

```
               380                 400                 420
                .         .         .         .         .         .
     GAGCAAGTTACTCAGATGGAAAACTGAAAGCCCCTCCTAAACCATGTGCTGGCAATCAAG
     +---------+---------+---------+---------+---------+---------
     CTCGTTCAATGAGTCTACCTTTTGACTTTCGGGGAGGATTTGGTACACGACCGTTAGTTC
       A  S  Y  S  D  G  K  L  K  A  P  P  K  P  C  A  G  N  Q  G
     440                 460                 480
       .         .         .         .         .         .
     GGACCCAGATCACGGTGGAGGACCTTTTTTACAACATAGCCACGAGGAGAAAAGCTTTAA
     +---------+---------+---------+---------+---------+---------
     CCTGGGTCTAGTGCCACCTCCTGGAAAAAATGTTGTATCGGTGCTCCTCTTTTCGAAATT
        T  Q  I  T  V  E  D  L  F  Y  N  I  A  T  R  R  K  A  L  K
     500                 520                 540
       .         .         .         .         .         .
     AAAATCCAAGTGAAGAATATGGGAAAATTTTGGAAGTTGTTGGCAGGTATTCAGTACACA
     +---------+---------+---------+---------+---------+---------
     TTTTAGGTTCACTTCTTATACCCTTTTAAAACCTTCAACAACCGTCCATAAGTCATGTGT
        N  P  S  E  E  Y  G  K  I  L  E  V  V  G  R  Y  S  V  H  N
     560                 580                 600
       .         .         .         .         .         .
     ATGCAGGCATTAGTTTCTCAGTTAAAAAACAAGGAGAGACAGTAGCTGATGTTAGGACAC
     +---------+---------+---------+---------+---------+---------
     TACGTCCGTAATCAAAGAGTCAATTTTTTGTTCCTCTCTGTCATCGACTACAATCCTGTG
        A  G  I  S  F  S  V  K  K  Q  G  E  T  V  A  D  V  R  T  L
     620                 640                 660
       .         .         .         .         .         .
     TACCCAATGCCTCAACCGTGGACAATATTCGCTCCGTCTTTGGAAATGCTGTTAGTCGAG
     +---------+---------+---------+---------+---------+---------
     ATGGGTTACGGAGTTGGCACCTGTTATAAGCGAGGCAGAAACCTTTACGACAATCAGCTC
        P  N  A  S  T  V  D  N  I  R  S  V  F  G  N  A  V  S  R  E
     680                 700                 720
       .         .         .         .         .         .
     AACTGATAGAAATTGGATGTGAGGATAAAACCCTAGCCTTCAAAATGAATGGTTACATAT
     +---------+---------+---------+---------+---------+---------
     TTGACTATCTTTAACCTACACTCCTATTTTGGGATCGGAAGTTTTACTTACCAATGTATA
         L  I  E  I  G  C  E  D  K  T  L  A  F  K  M  N  G  Y  I  S
     740                 760                 780
       .         .         .         .         .         .
     CCAATGCAAACTACTCAGTGAAGAAGTGCATCTTCTTACTCTTCATCAACCATCGTCTGG
     +---------+---------+---------+---------+---------+---------
     GGTTACGTTTGATGAGTCACTTCTTCACGTAGAAGAATGAGAAGTAGTTGGTAGCAGACC
        N  A  N  Y  S  V  K  K  C  I  F  L  L  F  I  N  H  R  L  V
```

FIG. 1B

```
                800                    820                    840
                 .                      .                      .
                 .                      .                      .
        TAGAATCAACTTCCTTGAGAAAAGCCATAGAAACAGTGTATGCAGCCTATTTGCCCAAAA
        +---------+---------+---------+---------+---------+---------
        ATCTTAGTTGAAGGAACTCTTTTCGGTATCTTTGTCACATACGTCGGATAAACGGGTTTT
          E  S  T  S  L  R  K  A  I  E  T  V  Y  A  A  Y  L  P  K  N
                860                    880                    900
                 .                      .                      .
                 .                      .                      .
        ACACACACCCATTCCTGTACCTCAGTTTAGAAATCAGTCCCCAGAATGTGGATGTTAATG
        +---------+---------+---------+---------+---------+---------
        TGTGTGTGGGTAAGGACATGGAGTCAAATCTTTAGTCAGGGGTCTTACACCTACAATTAC
           T  H  P  F  L  Y  L  S  L  E  I  S  P  Q  N  V  D  V  N  V
                920                    940                    960
                 .                      .                      .
                 .                      .                      .
        TGCACCCCACAAAGCATGAAGTTCACTTCCTGCACGAGGAGAGCATCCTGGAGCGGGTGC
        +---------+---------+---------+---------+---------+---------
        ACGTGGGGTGTTTCGTACTTCAAGTGAAGGACGTGCTCCTCTCGTAGGACCTCGCCCACG
           H  P  T  K  H  E  V  H  F  L  H  E  E  S  I  L  E  R  V  Q
                980                   1000                   1020
                 .                      .                      .
                 .                      .                      .
        AGCAGCACATCGAGAGCAAGCTCCTGGGCTCCAATTCCTCCAGGATGTACTTCACCCAGA
        +---------+---------+---------+---------+---------+---------
        TCGTCGTGTAGCTCTCGTTCGAGGACCCGAGGTTAAGGAGGTCCTACATGAAGTGGGTCT
           Q  H  I  E  S  K  L  L  G  S  N  S  S  R  M  Y  F  T  Q  T
               1040                   1060                   1080
                 .                      .                      .
                 .                      .                      .
        CTTTGCTACCAGGACTTGCTGGCCCCTCTGGGGAGATGGTTAAATCCACAACAAGTCTGA
        +---------+---------+---------+---------+---------+---------
        GAAACGATGGTCCTGAACGACCGGGGAGACCCCTCTACCAATTTAGGTGTTGTTCAGACT
           L  L  P  G  L  A  G  P  S  G  E  M  V  K  S  T  T  S  L  T
               1100                   1120                   1140
                 .                      .                      .
                 .                      .                      .
        CCTCGTCTTCTACTTCTGGAAGTAGTGATAAGGTCTATGCCCACCAGATGGTTCGTACAG
        +---------+---------+---------+---------+---------+---------
        GGAGCAGAAGATGAAGACCTTCATCACTATTCCAGATACGGGTGGTCTACCAAGCATGTC
           S  S  S  T  S  G  S  S  D  K  V  Y  A  H  Q  M  V  R  T  D
               1160                   1180                   1200
                 .                      .                      .
                 .                      .                      .
        ATTCCCGGGAACAGAAGCTTGATGCATTTCTGCAGCCTCTGAGCAAACCCCTGTCCAGTC
        +---------+---------+---------+---------+---------+---------
        TAAGGGCCCTTGTCTTCGAACTACGTAAAGACGTCGGAGACTCGTTTGGGGACAGGTCAG
           S  R  E  Q  K  L  D  A  F  L  Q  P  L  S  K  P  L  S  S  Q
```

FIG. 1C

```
                 1220                1240                 1260
                    .                   .                    .
          .         .         .         .         .          .
        AGCCCCAGGCCATTGTCACAGAGGATAAGACAGATATTTCTAGTGGCAGGGCTAGGCAGC
        +---------+---------+---------+---------+---------+---------
        TCGGGGTCCGGTAACAGTGTCTCCTATTCTGTCTATAAAGATCACCGTCCCGATCCGTCG
           P  Q  A  I  V  T  E  D  K  T  D  I  S  S  G  R  A  R  Q  Q
                 1280                1300                 1320
                    .                   .                    .
          .         .         .         .         .          .
        AAGATGAGGAGATGCTTGAACTCCCAGCCCCTGCTGAAGTGGCTGCCAAAAATCAGAGCT
        +---------+---------+---------+---------+---------+---------
        TTCTACTCCTCTACGAACTTGAGGGTCGGGGACGACTTCACCGACGGTTTTTAGTCTCGA
            D  E  E  M  L  E  L  P  A  P  A  E  V  A  A  K  N  Q  S  L
                 1340                1360                 1380
                    .                   .                    .
          .         .         .         .         .          .
        TGGAGGGGGATACAACAAAGGGGACTTCAGAAATGTCAGAGAAGAGAGGACCTACTTCCA
        +---------+---------+---------+---------+---------+---------
        ACCTCCCCCTATGTTGTTTCCCCTGAAGTCTTTACAGTCTCTTCTCTCCTGGATGAAGGT
            E  G  D  T  T  K  G  T  S  E  M  S  E  K  R  G  P  T  S  S
                 1400                1420                 1440
                    .                   .                    .
          .         .         .         .         .          .
        GCAACCCCAGAAAGAGACATCGGGAAGATTCTGATGTGGAAATGGTGGAAGATGATTCCC
        +---------+---------+---------+---------+---------+---------
        CGTTGGGGTCTTTCTCTGTAGCCCTTCTAAGACTACACCTTTACCACCTTCTACTAAGGG
            N  P  R  K  R  H  R  E  D  S  D  V  E  M  V  E  D  D  S  R
                 1460                1480                 1500
                    .                   .                    .
          .         .         .         .         .          .
        GAAAGGAAATGACTGCAGCTTGTACCCCCCGGAGAAGGATCATTAACCTCACTAGTGTTT
        +---------+---------+---------+---------+---------+---------
        CTTTCCTTTACTGACGTCGAACATGGGGGGCCTCTTCCTAGTAATTGGAGTGATCACAAA
            K  E  M  T  A  A  C  T  P  R  R  R  I  I  N  L  T  S  V  L
                 1520                1540                 1560
                    .                   .                    .
          .         .         .         .         .          .
        TGAGTCTCCAGGAAGAAATTAATGAGCAGGGACATGAGGTTCTCCGGGAGATGTTGCATA
        +---------+---------+---------+---------+---------+---------
        ACTCAGAGGTCCTTCTTTAATTACTCGTCCCTGTACTCCAAGAGGCCCTCTACAACGTAT
             S  L  Q  E  E  I  N  E  Q  G  H  E  V  L  R  E  M  L  H  N
                 1580                1600                 1620
                    .                   .                    .
          .         .         .         .         .          .
        ACCACTCCTTCGTGGGCTGTGTGAATCCTCAGTGGGCCTTGGCACAGCATCAAACCAAGT
        +---------+---------+---------+---------+---------+---------
        TGGTGAGGAAGCACCCGACACACTTAGGAGTCACCCGGAACCGTGTCGTAGTTTGGTTCA
             H  S  F  V  G  C  V  N  P  Q  W  A  L  A  Q  H  Q  T  K  L
```

FIG. 1D

```
         1640                1660                1680
           .                   .                   .
TATACCTTCTCAACACCACCAAGCTTAGTGAAGAACTGTTCTACCAGATACTCATTTATG
+---------+---------+---------+---------+---------+---------
ATATGGAAGAGTTGTGGTGGTTCGAATCACTTCTTGACAAGATGGTCTATGAGTAAATAC
   Y  L  N  T  T  K  L  S  E  E  L  F  Y  Q  I  L  I  Y  D
 1700                1720                1740
   .                   .                   .
ATTTTGCCAATTTTGGTGTTCTCAGGTTATCGGAGCCAGCACCGCTCTTTGACCTTGCCA
+---------+---------+---------+---------+---------+---------
TAAAACGGTTAAAACCACAAGAGTCCAATAGCCTCGGTCGTGGCGAGAAACTGGAACGGT
   F  A  N  F  G  V  L  R  L  S  E  P  A  P  L  F  D  L  A  M
 1760                1780                1800
   .                   .                   .
TGCTTGCCTTAGATAGTCCAGAGAGTGGCTGGACAGAGGAAGATGGTCCCAAAGAAGGAC
+---------+---------+---------+---------+---------+---------
ACGAACGGAATCTATCAGGTCTCTCACCGACCTGTCTCCTTCTACCAGGGTTTCTTCCTG
   L  A  L  D  S  P  E  S  G  W  T  E  E  D  G  P  K  E  G  L
 1820                1840                1860
   .                   .                   .
TTGCTGAATACATTGTTGAGTTTCTGAAGAAGAAGGCTGAGATGCTTGCAGACTATTTCT
+---------+---------+---------+---------+---------+---------
AACGACTTATGTAACAACTCAAAGACTTCTTCTTCCGACTCTACGAACGTCTGATAAAGA
   A  E  Y  I  V  E  F  L  K  K  K  A  E  M  L  A  D  Y  F  S
 1880                1900                1920
   .                   .                   .
CTTTGGAAATTGATGAGGAAGGGAACCTGATTGGATTACCCCTTCTGATTGACAACTATG
+---------+---------+---------+---------+---------+---------
GAAACCTTTAACTACTCCTTCCCTTGGACTAACCTAATGGGGAAGACTAACTGTTGATAC
   L  E  I  D  E  E  G  N  L  I  G  L  P  L  L  I  D  N  Y  V
 1940                1960                1980
   .                   .                   .
TGCCCCCTTTGGAGGGACTGCCTATCTTCATTCTTCGACTAGCCACTGAGGTGAATTGGG
---------+---------+---------+---------+---------+---------+
ACGGGGGAAACCTCCCTGACGGATAGAAGTAAGAAGCTGATCGGTGACTCCACTTAACCC
   P  P  L  E  G  L  P  I  F  I  L  R  L  A  T  E  V  N  W  D
 2000                2020                2040
   .                   .                   .
ACGAAGAAAAGGAATGTTTTGAAAGCCTCAGTAAAGAATGCGCTATGTTCTATTCCATCC
+---------+---------+---------+---------+---------+---------
TGCTTCTTTTCCTTACAAAACTTTCGGAGTCATTTCTTACGCGATACAAGATAAGGTAGG
   E  E  K  E  C  F  E  S  L  S  K  E  C  A  M  F  Y  S  I  R
```

FIG. 1E

```
         2060              2080              2100
           .                 .                 .
GGAAGCAGTACATATCTGAGGAGTCGACCCTCTCAGGCCAGCAGAGTGAAGTGCCTGGCT
+---------+---------+---------+---------+---------+---------
CCTTCGTCATGTATAGACTCCTCAGCTGGGAGAGTCCGGTCGTCTCACTTCACGGACCGA
   K  Q  Y  I  S  E  E  S  T  L  S  G  Q  Q  S  E  V  P  G  S
  2120              2140              2160
    .                 .                 .
CCATTCCAAACTCCTGGAAGTGGACTGTGGAACACATTGTCTATAAAGCCTTGCGCTCAC
+---------+---------+---------+---------+---------+---------
GGTAAGGTTTGAGGACCTTCACCTGACACCTTGTGTAACAGATATTTCGGAACGCGAGTG
    I  P  N  S  W  K  W  T  V  E  H  I  V  Y  K  A  L  R  S  H
  2180              2200              2220
    .                 .                 .
ACATTCTGCCTCCTAAACATTTCACAGAAGATGGAAATATCCTGCAGCTTGCTAACCTGC
+---------+---------+---------+---------+---------+---------
TGTAAGACGGAGGATTTGTAAAGTGTCTTCTACCTTTATAGGACGTCGAACGATTGGACG
     I  L  P  P  K  H  F  T  E  D  G  N  I  L  Q  L  A  N  L  P
  2240              2260              2280
    .                 .                 .
CTGATCTATACAAAGTCTTTGAGAGGTGTTAAATATGGTTATTTATGCACTGTGGGATGT
+---------+---------+---------+---------+---------+---------
GACTAGATATGTTTCAGAAACTCTCCACAATTTATACCAATAAATACGTGACACCCTACA
     D  L  Y  K  V  F  E  R  C  *
  2300              2320              2340
    .                 .                 .
GTTCTTCTTTCTCTGTATTCCGATACAAAGTGTTGTATCAAAGTGTGATATACAAAGTGT
+---------+---------+---------+---------+---------+---------
CAAGAAGAAAGAGACATAAGGCTATGTTTCACAACATAGTTTCACACTATATGTTTCACA
  2360              2380              2400
    .                 .                 .
ACCAACATAAGTGTTGGTAGCACTTAAGACTTATACTTGCCTTCTGATAGTATTCCTTTA
+---------+---------+---------+---------+---------+---------
TGGTTGTATTCACAACCATCGTGAATTCTGAATATGAACGGAAGACTATCATAAGGAAAT
  2420              2440              2460
    .                 .                 .
TACACAGTGGATTGATTATAAATAAATAGATGTGTCTTAACATAAAAAAAAAAAAAAAAA
+---------+---------+---------+---------+---------+---------
ATGTGTCACCTAACTAATATTTATTTATCTACACAGAATTGTATTTTTTTTTTTTTTTTT

2480
    .
AAAAA
+----
TTTTT
```

FIG. 1F

Polynucleotide and deduced amino acid sequence of hMLH2

```
         -70                 -50                 -30
          .         .         .         .         .
GGCACGAGTGGCTGCTTGCGGCTAGTGGATGGTAATTGCCTGCCTCGCGCTAGCAGCAAG
----------+---------+---------+---------+---------+---------+
CCGTGCTCACCGACGAACGCCGATCACCTACCATTAACGGACGGAGCGCGATCGTCGTTC
         -10                  10                 30
          .         .         .         .         .
CTGCTCTGTTAAAAGCGAAAATGAAACAATTGCCTGCGGCAACAGTTCGACTCCTTTCAA
----------+---------+---------+---------+---------+---------+
GACGAGACAATTTTCGCTTTTACTTTGTTAACGGACGCCGTTGTCAAGCTGAGGAAAGTT
                    M  K  Q  L  P  A  A  T  V  R  L  L  S  S
          50                  70                 90
          .         .         .         .         .
GTTCTCAGATCATCACTTCGGTGGTCAGTGTTGTAAAAGAGCTTATTGAAAACTCCTTGG
----------+---------+---------+---------+---------+---------+
CAAGAGTCTAGTAGTGAAGCCACCAGTCACAACATTTTCTCGAATAACTTTTGAGGAACC
   S  Q  I  I  T  S  V  V  S  V  V  K  E  L  I  E  N  S  L  D
         110                 130                 150
          .         .         .         .         .
ATGCTGGTGCCACAAGCGTAGATGTTAAACTGGAGAACTATGGATTTGATAAAATTGAGG
----------+---------+---------+---------+---------+---------+
TACGACCACGGTGTTCGCATCTACAATTTGACCTCTTGATACCTAAACTATTTTAACTCC
   A  G  A  T  S  V  D  V  K  L  E  N  Y  G  F  D  K  I  E  V
         170                 190                 210
          .         .         .         .         .
TGCGAGATAACGGGGAGGGTATCAAGGCTGTTGATGCACCTGTAATGGCAATGAAGTACT
----------+---------+---------+---------+---------+---------+
ACGCTCTATTGCCCCTCCCATAGTTCCGACAACTACGTGGACATTACCGTTACTTCATGA
   R  D  N  G  E  G  I  K  A  V  D  A  P  V  M  A  M  K  Y  Y
         230                 250                 270
          .         .         .         .         .
ACACCTCAAAAATAAATAGTCATGAAGATCTTGAAAATTTGACAACTTACGGTTTTCGTG
----------+---------+---------+---------+---------+---------+
TGTGGAGTTTTTATTTATCAGTACTTCTAGAACTTTTAAACTGTTGAATGCCAAAAGCAC
   T  S  K  I  N  S  H  E  D  L  E  N  L  T  T  Y  G  F  R  G
         290                 310                 330
          .         .         .         .         .
GAGAAGCCTTGGGGTCAATTTGTTGTATAGCTGAGGTTTTAATTACAACAAGAACGGCTG
----------+---------+---------+---------+---------+---------+
CTCTTCGGAACCCCAGTTAAACAACATATCGACTCCAAAATTAATGTTGTTCTTGCCGAC
   E  A  L  G  S  I  C  C  I  A  E  V  L  I  T  T  R  T  A  A
```

FIG. 2A

```
                  350                    370                    390
                   .                      .                      .
          .        .         .            .         .            .         .
    CTGATAATTTTAGCACCCAGTATGTTTTAGATGGCAGTGGCCACATACTTTCTCAGAAAC
    ---------+---------+---------+---------+---------+---------+
    GACTATTAAAATCGTGGGTCATACAAAATCTACCGTCACCGGTGTATGAAAGAGTCTTTG
       D  N  F  S  T  Q  Y  V  L  D  G  S  G  H  I  L  S  Q  K  P
                  410                    430                    450
                   .                      .                      .
          .        .         .            .         .            .         .
    CTTCACATCTTGGTCAAGGTACAACTGTAACTGCTTTAAGATTATTTAAGAATCTACCTG
    ---------+---------+---------+---------+---------+---------+
    GAAGTGTAGAACCAGTTCCATGTTGACATTGACGAAATTCTAATAAATTCTTAGATGGAC
       S  H  L  G  Q  G  T  T  V  T  A  L  R  L  F  K  N  L  P  V
                  470                    490                    510
                   .                      .                      .
          .        .         .            .         .            .         .
    TAAGAAAGCAGTTTTACTCAACTGCAAAAAAATGTAAAGATGAAATAAAAAAGATCCAAG
    ---------+---------+---------+---------+---------+---------+
    ATTCTTTCGTCAAAATGAGTTGACGTTTTTTTACATTTCTACTTTATTTTTTCTAGGTTC
       R  K  Q  F  Y  S  T  A  K  K  C  K  D  E  I  K  K  I  Q  D
                  530                    550                    570
                   .                      .                      .
          .        .         .            .         .            .         .
    ATCTCCTCATGAGCTTTGGTATCCTTAAACCTGACTTAAGGATTGTCTTTGTACATAACA
    ---------+---------+---------+---------+---------+---------+
    TAGAGGAGTACTCGAAACCATAGGAATTTGGACTGAATTCCTAACAGAAACATGTATTGT
       L  L  M  S  F  G  I  L  K  P  D  L  R  I  V  F  V  H  N  K
                  590                    610                    630
                   .                      .                      .
          .        .         .            .         .            .         .
    AGGCAGTTATTTGGCAGAAAAGCAGAGTATCAGATCACAAGATGGCTCTCATGTCAGTTC
    ---------+---------+---------+---------+---------+---------+
    TCCGTCAATAAACCGTCTTTTCGTCTCATAGTCTAGTGTTCTACCGAGAGTACAGTCAAG
       A  V  I  W  Q  K  S  R  V  S  D  H  K  M  A  L  M  S  V  L
                  650                    670                    690
                   .                      .                      .
          .        .         .            .         .            .         .
    TGGGGACTGCTGTTATGAACAATATGGAATCCTTTCAGTACCACTCTGAAGAATCTCAGA
    ---------+---------+---------+---------+---------+---------+
    ACCCCTGACGACAATACTTGTTATACCTTAGGAAAGTCATGGTGAGACTTCTTAGAGTCT
       G  T  A  V  M  N  N  M  E  S  F  Q  Y  H  S  E  E  S  Q  I
                  710                    730                    750
                   .                      .                      .
          .        .         .            .         .            .         .
    TTTATCTCAGTGGATTTCTTCCAAAGTGTGATGCAGACCACTCTTTCACTAGTCTTTCAA
    ---------+---------+---------+---------+---------+---------+
    AAATAGAGTCACCTAAAGAAGGTTTCACACTACGTCTGGTGAGAAAGTGATCAGAAAGTT
       Y  L  S  G  F  L  P  K  C  D  A  D  H  S  F  T  S  L  S  T
```

FIG. 2B

```
                    770               790                810
                      .                 .                  .
         CACCAGAAAGAAGTTTCATCTTCATAAACAGTCGACCAGTACATCAAAAAGATATCTTAA
         ----------+---------+---------+---------+---------+---------+
         GTGGTCTTTCTTCAAAGTAGAAGTATTTGTCAGCTGGTCATGTAGTTTTTCTATAGAATT
            P  E  R  S  F  I  F  I  N  S  R  P  V  H  Q  K  D  I  L  K
                    830               850                870
                      .                 .                  .
         AGTTAATCCGACATCATTACAATCTGAAATGCCTAAAGGAATCTACTCGTTTGTATCCTG
         ----------+---------+---------+---------+---------+---------+
         TCAATTAGGCTGTAGTAATGTTAGACTTTACGGATTTCCTTAGATGAGCAAACATAGGAC
            L  I  R  H  H  Y  N  L  K  C  L  K  E  S  T  R  L  Y  P  V
                    890               910                930
                      .                 .                  .
         TTTTCTTTCTGAAAATCGATGTTCCTACAGCTGATGTTGATGTAAATTTAACACCAGATA
         ----------+---------+---------+---------+---------+---------+
         AAAAGAAAGACTTTTAGCTACAAGGATGTCGACTACAACTACATTTAAATTGTGGTCTAT
            F  F  L  K  I  D  V  P  T  A  D  V  D  V  N  L  T  P  D  K
                    950               970                990
                      .                 .                  .
         AAAGCCAAGTATTATTACAAAATAAGGAATCTGTTTTAATTGCTCTTGAAAATCTGATGA
         ----------+---------+---------+---------+---------+---------+
         TTTCGGTTCATAATAATGTTTTATTCCTTAGACAAAATTAACGAGAACTTTTAGACTACT
            S  Q  V  L  L  Q  N  K  E  S  V  L  I  A  L  E  N  L  M  T
                    1010              1030               1050
                      .                 .                  .
         CGACTTGTTATGGACCATTACCTAGTACAAATTCTTATGAAAATAATAAAACAGATGTTT
         ----------+---------+---------+---------+---------+---------+
         GCTGAACAATACCTGGTAATGGATCATGTTTAAGAATACTTTTATTATTTTGTCTACAAA
            T  C  Y  G  P  L  P  S  T  N  S  Y  E  N  N  K  T  D  V  S
                    1070              1090               1110
                      .                 .                  .
         CCGCAGCTGACATCGTTCTTAGTAAAACAGCAGAAACAGATGTGCTTTTTAATAAAGTGG
         ----------+---------+---------+---------+---------+---------+
         GGCGTCGACTGTAGCAAGAATCATTTTGTCGTCTTTGTCTACACGAAAAATTATTTCACC
            A  A  D  I  V  L  S  K  T  A  E  T  D  V  L  F  N  K  V  E
                    1130              1150               1170
                      .                 .                  .
         AATCATCTGGAAAGAATTATTCAAATGTTGATACTTCAGTCATTCCATTCCAAAATGATA
         ----------+---------+---------+---------+---------+---------+
         TTAGTAGACCTTTCTTAATAAGTTTACAACTATGAAGTCAGTAAGGTAAGGTTTTACTAT
            S  S  G  K  N  Y  S  N  V  D  T  S  V  I  P  F  Q  N  D  M
```

FIG. 2C

```
                  1190                1210                1230
                    .                   .                   .
                    .                   .                   .
       TGCATAATGATGAATCTGGAAAAAACACTGATGATTGTTTAAATCACCAGATAAGTATTG
       ----------+---------+---------+---------+---------+---------+
       ACGTATTACTACTTAGACCTTTTTTGTGACTACTAACAAATTTAGTGGTCTATTCATAAC
        H  N  D  E  S  G  K  N  T  D  D  C  L  N  H  Q  I  S  I  G
                  1250                1270                1290
                    .                   .                   .
                    .                   .                   .
       GTGACTTTGGTTATGGTCATTGTAGTAGTGAAATTTCTAACATTGATAAAAACACTAAGA
       ----------+---------+---------+---------+---------+---------+
       CACTGAAACCAATACCAGTAACATCATCACTTTAAAGATTGTAACTATTTTGTGATTCT
        D  F  G  Y  G  H  C  S  S  E  I  S  N  I  D  K  N  T  K  N
                  1310                1330                1350
                    .                   .                   .
                    .                   .                   .
       ATGCATTTCAGGACATTTCAATGAGTAATGTATCATGGGAGAACTCTCAGACGGAATATA
       ----------+---------+---------+---------+---------+---------+
       TACGTAAAGTCCTGTAAAGTTACTCATTACATAGTACCCTCTTGAGAGTCTGCCTTATAT
        A  F  Q  D  I  S  M  S  N  V  S  W  E  N  S  Q  T  E  Y  S
                  1370                1390                1410
                    .                   .                   .
                    .                   .                   .
       GTAAAACTTGTTTTATAAGTTCCGTTAAGCACACCCAGTCAGAAAATGGCAATAAAGACC
       ----------+---------+---------+---------+---------+---------+
       CATTTTGAACAAAATATTCAAGGCAATTCGTGTGGGTCAGTCTTTTACCGTTATTTCTGG
        K  T  C  F  I  S  S  V  K  H  T  Q  S  E  N  G  N  K  D  H
                  1430                1450                1470
                    .                   .                   .
                    .                   .                   .
       ATATAGATGAGAGTGGGGAAAATGAGGAAGAAGCAGGTCTTGAAAACTCTTCGGAAATTT
       ----------+---------+---------+---------+---------+---------+
       TATATCTACTCTCACCCCTTTTACTCCTTCTTCGTCCAGAACTTTTGAGAAGCCTTTAAA
        I  D  E  S  G  E  N  E  E  E  A  G  L  E  N  S  S  E  I  S
                  1490                1510                1530
                    .                   .                   .
                    .                   .                   .
       CTGCAGATGAGTGGAGCAGGGGAAATATACTTAAAAATTCAGTGGGAGAGAATATTGAAC
       ----------+---------+---------+---------+---------+---------+
       GACGTCTACTCACCTCGTCCCCTTTATATGAATTTTTAAGTCACCCTCTCTTATAACTTG
        A  D  E  W  S  R  G  N  I  L  K  N  S  V  G  E  N  I  E  P
                  1550                1570                1590
                    .                   .                   .
                    .                   .                   .
       CTGTGAAAATTTTAGTGCCTGAAAAAAGTTTACCATGTAAAGTAAGTAATAATAATTATC
       ----------+---------+---------+---------+---------+---------+
       GACACTTTTAAAATCACGGACTTTTTTCAAATGGTACATTTCATTCATTATTATTAATAG
        V  K  I  L  V  P  E  K  S  L  P  C  K  V  S  N  N  N  Y  P

FIG. 2D
```

```
                 1610                1630                1650
                   .                   .                   .
         CAATCCCTGAACAAATGAATCTTAATGAAGATTCATGTAACAAAAAATCAAATGTAATAG
         ---------+---------+---------+---------+---------+---------+
         GTTAGGGACTTGTTTACTTAGAATTACTTCTAAGTACATTGTTTTTTAGTTTACATTATC
             I  P  E  Q  M  N  L  N  E  D  S  C  N  K  K  S  N  V  I  D
                 1670                1690                1710
                   .                   .                   .
         ATAATAAATCTGGAAAAGTTACAGCTTATGATTTACTTAGCAATCGAGTAATCAAGAAAC
         ---------+---------+---------+---------+---------+---------+
         TATTATTTAGACCTTTTCAATGTCGAATACTAAATGAATCGTTAGCTCATTAGTTCTTTG
             N  K  S  G  K  V  T  A  Y  D  L  L  S  N  R  V  I  K  K  P
                 1730                1750                1770
                   .                   .                   .
         CCATGTCAGCAAGTGCTCTTTTTGTTCAAGATCATCGTCCTCAGTTTCTCATAGAAAATC
         ---------+---------+---------+---------+---------+---------+
         GGTACAGTCGTTCACGAGAAAAACAAGTTCTAGTAGCAGGAGTCAAAGAGTATCTTTTAG
             M  S  A  S  A  L  F  V  Q  D  H  R  P  Q  F  L  I  E  N  P
                 1790                1810                1830
                   .                   .                   .
         CTAAGACTAGTTTAGAGGATGCAACACTACAAATTGAAGAACTGTGGAAGACATTGAGTG
         ---------+---------+---------+---------+---------+---------+
         GATTCTGATCAAATCTCCTACGTTGTGATGTTTAACTTCTTGACACCTTCTGTAACTCAC
             K  T  S  L  E  D  A  T  L  Q  I  E  E  L  W  K  T  L  S  E
                 1850                1870                1890
                   .                   .                   .
         AAGAGGAAAAACTGAAATATGAAGAGAAGGCTACTAAAGACTTGGAACGATACAATAGTC
         ---------+---------+---------+---------+---------+---------+
         TTCTCCTTTTTGACTTTATACTTCTCTTCCGATGATTTCTGAACCTTGCTATGTTATCAG
             E  E  K  L  K  Y  E  E  K  A  T  K  D  L  E  R  Y  N  S  Q
                 1910                1930                1950
                   .                   .                   .
         AAATGAAGAGAGCCATTGAACAGGAGTCACAAATGTCACTAAAAGATGGCAGAAAAAAGA
         ---------+---------+---------+---------+---------+---------+
         TTTACTTCTCTCGGTAACTTGTCCTCAGTGTTTACAGTGATTTTCTACCGTCTTTTTTCT
             M  K  R  A  I  E  Q  E  S  Q  M  S  L  K  D  G  R  K  K  I
                 1970                1990                2010
                   .                   .                   .
         TAAAACCCACCAGCGCATGGAATTTGGCCCAGAAGCACAAGTTAAAAACCTCATTATCTA
         ---------+---------+---------+---------+---------+---------+
         ATTTTGGGTGGTCGCGTACCTTAAACCGGGTCTTCGTGTTCAATTTTTGGAGTAATAGAT
             K  P  T  S  A  W  N  L  A  Q  K  H  K  L  K  T  S  L  S  N
```

FIG. 2E

```
              2030                2050                 2070
                .                   .                    .
     ATCAACCAAAACTTGATGAACTCCTTCAGTCCCAAATTGAAAAAGAAGGAGTCAAAATA
     ---------+---------+---------+---------+---------+---------+
     TAGTTGGTTTTGAACTACTTGAGGAAGTCAGGGTTTAACTTTTTTCTTCCTCAGTTTTAT
       Q  P  K  L  D  E  L  L  Q  S  Q  I  E  K  R  R  S  Q  N  I
              2090                2110                 2130
                .                   .                    .
     TTAAAATGGTACAGATCCCCTTTTCTATGAAAAACTTAAAAATAAATTTTAAGAAACAAA
     ---------+---------+---------+---------+---------+---------+
     AATTTTACCATGTCTAGGGGAAAAGATACTTTTTGAATTTTTATTTAAAATTCTTTGTTT
         K  M  V  Q  I  P  F  S  M  K  N  L  K  I  N  F  K  K  Q  N
              2150                2170                 2190
                .                   .                    .
     ACAAAGTTGACTTAGAAGAGAAGGATGAACCTTGCTTGATCCACAATCTCAGGTTTCCTG
     ---------+---------+---------+---------+---------+---------+
     TGTTTCAACTGAATCTTCTCTTCCTACTTGGAACGAACTAGGTGTTAGAGTCCAAAGGAC
        K  V  D  L  E  E  K  D  E  P  C  L  I  H  N  L  R  F  P  D
              2210                2230                 2250
                .                   .                    .
     ATGCATGGCTAATGACATCCAAAACAGAGGTAATGTTATTAAATCCATATAGAGTAGAAG
     ---------+---------+---------+---------+---------+---------+
     TACGTACCGATTACTGTAGGTTTTGTCTCCATTACAATAATTTAGGTATATCTCATCTTC
         A  W  L  M  T  S  K  T  E  V  M  L  L  N  P  Y  R  V  E  E
              2270                2290                 2310
                .                   .                    .
     AAGCCCTGCTATTTAAAAGACTTCTTGAGAATCATAAACTTCCTGCAGAGCCACTGGAAA
     ---------+---------+---------+---------+---------+---------+
     TTCGGGACGATAAATTTTCTGAAGAACTCTTAGTATTTGAAGGACGTCTCGGTGACCTTT
         A  L  L  F  K  R  L  L  E  N  H  K  L  P  A  E  P  L  E  K
              2330                2350                 2370
                .                   .                    .
     AGCCAATTATGTTAACAGAGAGTCTTTTTAATGGATCTCATTATTTAGACGTTTTATATA
     ---------+---------+---------+---------+---------+---------+
     TCGGTTAATACAATTGTCTCTCAGAAAAATTACCTAGAGTAATAAATCTGCAAAATATAT
         P  I  M  L  T  E  S  L  F  N  G  S  H  Y  L  D  V  L  Y  K
              2390                2410                 2430
                .                   .                    .
     AAATGACAGCAGATGACCAAAGATACAGTGGATCAACTTACCTGTCTGATCCTCGTCTTA
     ---------+---------+---------+---------+---------+---------+
     TTTACTGTCGTCTACTGGTTTCTATGTCACCTAGTTGAATGGACAGACTAGGAGCAGAAT
         M  T  A  D  D  Q  R  Y  S  G  S  T  Y  L  S  D  P  R  L  T
```

FIG. 2F

```
              2450               2470               2490
               .                  .                  .
CAGCGAATGGTTTCAAGATAAAATTGATACCAGGAGTTTCAATTACTGAAAATTACTTGG
---------+---------+---------+---------+---------+---------+
GTCGCTTACCAAAGTTCTATTTTAACTATGGTCCTCAAAGTTAATGACTTTTAATGAACC
  A  N  G  F  K  I  K  L  I  P  G  V  S  I  T  E  N  Y  L  E
              2510               2530               2550

.                  .                  .
AAATAGAAGGAATGGCTAATTGTCTCCCATTCTATGGAGTAGCAGATTTAAAAGAAATTC
---------+---------+---------+---------+---------+---------+
TTTATCTTCCTTACCGATTAACAGAGGGTAAGATACCTCATCGTCTAAATTTTCTTTAAG
   I  E  G  M  A  N  C  L  P  F  Y  G  V  A  D  L  K  E  I  L
              2570               2590               2610

.                  .                  .
TTAATGCTATATTAAACAGAAATGCAAAGGAAGTTTATGAATGTAGACCTCGCAAAGTGA
---------+---------+---------+---------+---------+---------+
AATTACGATATAATTTGTCTTTACGTTTCCTTCAAATACTTACATCTGGAGCGTTTCACT
    N  A  I  L  N  R  N  A  K  E  V  Y  E  C  R  P  R  K  V  I
              2630               2650               2670

.                  .                  .
TAAGTTATTTAGAGGGAGAAGCAGTGCGTCTATCCAGACAATTACCCATGTACTTATCAA
---------+---------+---------+---------+---------+---------+
ATTCAATAAATCTCCCTCTTCGTCACGCAGATAGGTCTGTTAATGGGTACATGAATAGTT
   S  Y  L  E  G  E  A  V  R  L  S  R  Q  L  P  M  Y  L  S  K
              2690               2710               2730

.                  .                  .
AAGAGGACATCCAAGACATTATCTACAGAATGAAGCACCAGTTTGGAAATGAAATTAAAG
---------+---------+---------+---------+---------+---------+
TTCTCCTGTAGGTTCTGTAATAGATGTCTTACTTCGTGGTCAAACCTTTACTTTAATTTC
    E  D  I  Q  D  I  I  Y  R  M  K  H  Q  F  G  N  E  I  K  E
              2750               2770               2790

.                  .                  .
AGTGTGTTCATGGTCGCCCATTTTTTCATCATTTAACCTATCTTCCAGAAACTACATGAT
---------+---------+---------+---------+---------+---------+
TCACACAAGTACCAGCGGGTAAAAAAGTAGTAAATTGGATAGAAGGTCTTTGATGTACTA
    C  V  H  G  R  P  F  F  H  H  L  T  Y  L  P  E  T  T  *
              2810               2830               2850

.                  .                  .
TAAATATGTTTAAGAAGATTAGTTACCATTGAAATTGGTTCTGTCATAAAACAGCATGAG
---------+---------+---------+---------+---------+---------+
ATTTATACAAATTCTTCTAATCAATGGTAACTTTAACCAAGACAGTATTTTGTCGTACTC
```

FIG. 2G

```
              2870                2890                 2910
                 .                   .                    .
       TCTGGTTTTAAATTATCTTTGTATTATGTGTCACATGGTTATTTTTTAAATGAGGATTCA
       ---------+---------+---------+---------+---------+---------+
       AGACCAAAATTTAATAGAAACATAATACACAGTGTACCAATAAAAAATTTACTCCTAAGT
              2930                2950                 2970
                 .                   .                    .
       CTGACTTGTTTTTATATTGAAAAAGTTCCACGTATTGTAGAAAACGTAAATAAACTAAT
       ---------+---------+---------+---------+---------+---------+
       GACTGAACAAAAATATAACTTTTTTCAAGGTGCATAACATCTTTTGCATTTATTTGATTA

AAC
       ---
       TTG
```

FIG. 2H

Polynucleotide and deduced amino acid sequence of hMLH3

```
      -20                    0                    20
        .          .          .          .          .          .
    CGAGGCGGATCGGGTGTTGCATCCATGGAGCGAGCTGAGAGCTCGAGTACAGAACCTGCT
    ---+----------+----------+----------+----------+----------+------
    GCTCCGCCTAGCCCACAACGTAGGTACCTCGCTCGACTCTCGAGCTCATGTCTTGGACGA
                            M  E  R  A  E  S  S  T  E  P  A
       40                   60                   80
        .          .          .          .          .          .
    AAGGCCATCAAACCTATTGATCGGAAGTCAGTCCATCAGATTTGCTCTGGGCAGGTGGTA
    ---+----------+----------+----------+----------+----------+------
    TTCCGGTAGTTTGGATAACTAGCCTTCAGTCAGGTAGTCTAAACGAGACCCGTCCACCAT
    K  A  I  K  P  I  D  R  K  S  V  H  Q  I  C  S  G  Q  V  V
      100                  120                  140
        .          .          .          .          .          .
    CTGAGTCTAAGCACTGCGGTAAAGGAGTTAGTAGAAAACAGTCTGGATGCTGGTGCCACT
    ---+----------+----------+----------+----------+----------+------
    GACTCAGATTCGTGACGCCATTTCCTCAATCATCTTTTGTCAGACCTACGACCACGGTGA
    L  S  L  S  T  A  V  K  E  L  V  E  N  S  L  D  A  G  A  T
      160                  180                  200
        .          .          .          .          .          .
    AATATTGATCTAAAGCTTAAGGACTATGGAGTGGATCTTATTGAAGTTTCAGACAATGGA
    ---+----------+----------+----------+----------+----------+------
    TTATAACTAGATTTCGAATTCCTGATACCTCACCTAGAATAACTTCAAAGTCTGTTACCT
    N  I  D  L  K  L  K  D  Y  G  V  D  L  I  E  V  S  D  N  G
       220                  240                  260
        .          .          .          .          .          .
    TGTGGGGTAGAAGAAGAAAACTTCGAAGGCTTAACTCTGAAACATCACACATCTAAGATT
    ---+----------+----------+----------+----------+----------+------
    ACACCCCATCTTCTTCTTTTGAAGCTTCCGAATTGAGACTTTGTAGTGTGTAGATTCTAA
    C  G  V  E  E  E  N  F  E  G  L  T  L  K  H  H  T  S  K  I
       280                  300                  320
        .          .          .          .          .          .
    CAAGAGTTTGCCGACCTAACTCAGGTTGAAACTTTTGGCTTTCGGGGGGAAGCTCTGAGC
    ---+----------+----------+----------+----------+----------+------
    GTTCTCAAACGGCTGGATTGAGTCCAACTTTGAAAACCGAAAGCCCCCCTTCGAGACTCG
    Q  E  F  A  D  L  T  Q  V  E  T  F  G  F  R  G  E  A  L  S
       340                  360                  380
        .          .          .          .          .          .
    TCACTTTGTGCACTGAGCGATGTCACCATTTCTACCTGCCACGCATCGGCGAAGGTTGGA
    ---+----------+----------+----------+----------+----------+------
    AGTGAAACACGTGACTCGCTACAGTGGTAAAGATGGACGGTGCGTAGCCGCTTCCAACCT
    S  L  C  A  L  S  D  V  T  I  S  T  C  H  A  S  A  K  V  G
```

FIG. 3A

```
              400                 420                 440
               .                   .                   .
               .                   .                   .
    ACTCGACTGATGTTTGATCACAATGGGAAAATTATCCAGAAAACCCCCTACCCCCGCCCC
    ---+---------+---------+---------+---------+---------+------
    TGAGCTGACTACAAACTAGTGTTACCCTTTTAATAGGTCTTTTGGGGGATGGGGGCGGGG
     T  R  L  M  F  D  H  N  G  K  I  I  Q  K  T  P  Y  P  R  P
              460                 480                 500
               .                   .                   .
               .                   .                   .
    AGAGGGACCACAGTCAGCGTGCAGCAGTTATTTTCCACACTACCTGTGCGCCATAAGGAA
    ---+---------+---------+---------+---------+---------+------
    TCTCCCTGGTGTCAGTCGCACGTCGTCAATAAAAGGTGTGATGGACACGCGGTATTCCTT
     R  G  T  T  V  S  V  Q  Q  L  F  S  T  L  P  V  R  H  K  E
              520                 540                 560
               .                   .                   .
               .                   .                   .
    TTTCAAAGGAATATTAAGAAGGAGTATGCCAAAATGGTCCAGGTCTTACATGCATACTGT
    ---+---------+---------+---------+---------+---------+------
    AAAGTTTCCTTATAATTCTTCCTCATACGGTTTTACCAGGTCCAGAATGTACGTATGACA
     F  Q  R  N  I  K  K  E  Y  A  K  M  V  Q  V  L  H  A  Y  C
              580                 600                 620
               .                   .                   .
               .                   .                   .
    ATCATTTCAGCAGGCATCCGTGTAAGTTGCACCAATCAGCTTGGACAAGGAAAACGACAG
    ---+---------+---------+---------+---------+---------+------
    TAGTAAAGTCGTCCGTAGGCACATTCAACGTGGTTAGTCGAACCTGTTCCTTTTGCTGTC
     I  I  S  A  G  I  R  V  S  C  T  N  Q  L  G  Q  G  K  R  Q
              640                 660                 680
               .                   .                   .
               .                   .                   .
    CCTGTGGTATGCACAGGTGGAAGCCCCAGCATAAAGGAAAATATCGGCTCTGTGTTTGGG
    ---+---------+---------+---------+---------+---------+------
    GGACACCATACGTGTCCACCTTCGGGGTCGTATTTCCTTTTATAGCCGAGACACAAACCC
     P  V  V  C  T  G  G  S  P  S  I  K  E  N  I  G  S  V  F  G
              700                 720                 740
               .                   .                   .
               .                   .                   .
    CAGAAGCAGTTGCAAAGCCTCATTCCTTTTGTTCAGCTGCCCCCTAGTGACTCCGTGTGT
    ---+---------+---------+---------+---------+---------+------
    GTCTTCGTCAACGTTTCGGAGTAAGGAAAACAAGTCGACGGGGGATCACTGAGGCACACA
     Q  K  Q  L  Q  S  L  I  P  F  V  Q  L  P  P  S  D  S  V  C
              760                 780                 800
               .                   .                   .
               .                   .                   .
    GAAGAGTACGGTTTGAGCTGTTCGGATGCTCTGCATAATCTTTTTTACATCTCAGGTTTC
    ---+---------+---------+---------+---------+---------+------
    CTTCTCATGCCAAACTCGACAAGCCTACGAGACGTATTAGAAAAAATGTAGAGTCCAAAG
     E  E  Y  G  L  S  C  S  D  A  L  H  N  L  F  Y  I  S  G  F
```

FIG. 3B

```
                820                 840                 860
                 .                   .                   .
       ATTTCACAATGCACGCATGGAGTTGGAAGGAGTTCAACAGACAGACAGTTTTTCTTTATC
       ---+---------+---------+---------+---------+---------+------
       TAAAGTGTTACGTGCGTACCTCAACCTTCCTCAAGTTGTCTGTCTGTCAAAAGAAATAG
        I  S  Q  C  T  H  G  V  G  R  S  S  T  D  R  Q  F  F  F  I
              880                 900                 920
                 .                   .                   .
       AACCGGCGGCCTTGTGACCCAGCAAAGGTCTGCAGACTCGTGAATGAGGTCTACCACATG
       ---+---------+---------+---------+---------+---------+------
       TTGGCCGCCGGAACACTGGGTCGTTTCCAGACGTCTGAGCACTTACTCCAGATGGTGTAC
        N  R  R  P  C  D  P  A  K  V  C  R  L  V  N  E  V  Y  H  M
              940                 960                 980
                 .                   .                   .
       TATAATCGACACCAGTATCCATTTGTTGTTCTTAACATTTCTGTTGATTCAGAATGCGTT
       ---+---------+---------+---------+---------+---------+------
       ATATTAGCTGTGGTCATAGGTAAACAACAAGAATTGTAAAGACAACTAAGTCTTACGCAA
        Y  N  R  H  Q  Y  P  F  V  V  L  N  I  S  V  D  S  E  C  V
             1000                1020                1040
                 .                   .                   .
       GATATCAATGTTACTCCAGATAAAAGGCAAATTTTGCTACAAGAGGAAAAGCTTTTGTTG
       ---+---------+---------+---------+---------+---------+------
       CTATAGTTACAATGAGGTCTATTTTCCGTTTAAAACGATGTTCTCCTTTTCGAAAACAAC
        D  I  N  V  T  P  D  K  R  Q  I  L  L  Q  E  E  K  L  L  L
             1060                1080                1100
                 .                   .                   .
       GCAGTTTTAAAGACCTCTTTGATAGGAATGTTTGATAGTGATGTCAACAAGCTAAATGTC
       ---+---------+---------+---------+---------+---------+------
       CGTCAAAATTTCTGGAGAAACTATCCTTACAAACTATCACTACAGTTGTTCGATTTACAG
        A  V  L  K  T  S  L  I  G  M  F  D  S  D  V  N  K  L  N  V
             1120                1140                1160
                 .                   .                   .
       AGTCAGCAGCCACTGCTGGATGTTGAAGGTAACTTAATAAAAATGCATGCAGCGGATTTG
       ---+---------+---------+---------+---------+---------+------
       TCAGTCGTCGGTGACGACCTACAACTTCCATTGAATTATTTTTACGTACGTCGCCTAAAC
        S  Q  Q  P  L  L  D  V  E  G  N  L  I  K  M  H  A  A  D  L
             1180                1200                1220
                 .                   .                   .
       GAAAAGCCCATGGTAGAAAAGCAGGATCAATCCCCTTCATTAAGGACTGGAGAAGAAAAA
       ---+---------+---------+---------+---------+---------+------
       CTTTTCGGGTACCATCTTTTCGTCCTAGTTAGGGGAAGTAATTCCTGACCTCTTCTTTTT
        E  K  P  M  V  E  K  Q  D  Q  S  P  S  L  R  T  G  E  E  K
```

FIG. 3C

```
                1240                1260                1280
                 .                   .                   .
      AAAGACGTGTCCATTTCCAGACTGCGAGAGGCCTTTTCTCTTCGTCACACAACAGAGAAC
      ---+---------+---------+---------+---------+---------+------
      TTTCTGCACAGGTAAAGGTCTGACGCTCTCCGGAAAAGAGAAGCAGTGTGTTGTCTCTTG
       K  D  V  S  I  S  R  L  R  E  A  F  S  L  R  H  T  T  E  N
                1300                1320                1340
                 .                   .                   .
      AAGCCTCACAGCCCAAAGACTCCAGAACCAAGAAGGAGCCCTCTAGGACAGAAAAGGGGT
      ---+---------+---------+---------+---------+---------+------
      TTCGGAGTGTCGGGTTTCTGAGGTCTTGGTTCTTCCTCGGGAGATCCTGTCTTTTCCCCA
       K  P  H  S  P  K  T  P  E  P  R  R  S  P  L  G  Q  K  R  G
                1360                1380                1400
                 .                   .                   .
      ATGCTGTCTTCTAGCACTTCAGGTGCCATCTCTGACAAAGGCGTCCTGAGACCTCAGAAA
      ---+---------+---------+---------+---------+---------+------
      TACGACAGAAGATCGTGAAGTCCACGGTAGAGACTGTTTCCGCAGGACTCTGGAGTCTTT
       M  L  S  S  S  T  S  G  A  I  S  D  K  G  V  L  R  P  Q  K
                1420                1440                1460
                 .                   .                   .
      GAGGCAGTGAGTTCCAGTCACGGACCCAGTGACCCTACGGACAGAGCGGAGGTGGAGAAG
      ---+---------+---------+---------+---------+---------+------
      CTCCGTCACTCAAGGTCAGTGCCTGGGTCACTGGGATGCCTGTCTCGCCTCCACCTCTTC
       E  A  V  S  S  H  G  P  S  D  P  T  D  R  A  E  V  E  K
                1480                1500                1520
                 .                   .                   .
      GACTCGGGGCACGGCAGCACTTCCGTGGATTCTGAGGGGTTCAGCATCCCAGACACGGGC
      ---+---------+---------+---------+---------+---------+------
      CTGAGCCCCGTGCCGTCGTGAAGGCACCTAAGACTCCCCAAGTCGTAGGGTCTGTGCCCG
       D  S  G  H  G  S  T  S  V  D  S  E  G  F  S  I  P  D  T  G
                1540                1560                1580
                 .                   .                   .
      AGTCACTGCAGCAGCGAGTATGCGGCCAGCTCCCCAGGGGACAGGGGCTCGCAGGAACAT
      ---+---------+---------+---------+---------+---------+------
      TCAGTGACGTCGTCGCTCATACGCCGGTCGAGGGGTCCCCTGTCCCCGAGCGTCCTTGTA
       S  H  C  S  S  E  Y  A  A  S  S  P  G  D  R  G  S  Q  E  H
                1600                1620                1640
                 .                   .                   .
      GTGGACTCTCAGGAGAAAGCGCCTGAAACTGACGACTCTTTTTCAGATGTGGACTGCCAT
      ---+---------+---------+---------+---------+---------+------
      CACCTGAGAGTCCTCTTTCGCGGACTTTGACTGCTGAGAAAAAGTCTACACCTGACGGTA
       V  D  S  Q  E  K  A  P  E  T  D  D  S  F  S  D  V  D  C  H
```

FIG. 3D

```
                1660                1680                1700
                 .                   .                   .
          TCAAACCAGGAAGATACCGGATGTAAATTTCGAGTTTTGCCTCAGCCAACTAATCTCGCA
          ---+---------+---------+---------+---------+---------+------
          AGTTTGGTCCTTCTATGGCCTACATTTAAAGCTCAAAACGGAGTCGGTTGATTAGAGCGT
           S  N  Q  E  D  T  G  C  K  F  R  V  L  P  Q  P  T  N  L  A
                1720                1740                1760
                 .                   .                   .
          ACCCCAAACACAAAGCGTTTTAAAAAAGAAGAAATTCTTTCCAGTTCTGACATTTGTCAA
          ---+---------+---------+---------+---------+---------+------
          TGGGGTTTGTGTTTCGCAAAATTTTTTCTTCTTTAAGAAAGGTCAAGACTGTAAACAGTT
           T  P  N  T  K  R  F  K  K  E  E  I  L  S  S  S  D  I  C  Q
                1780                1800                1820
                 .                   .                   .
          AAGTTAGTAAATACTCAGGACATGTCAGCCTCTCAGGTTGATGTAGCTGTGAAAATTAAT
          ---+---------+---------+---------+---------+---------+------
          TTCAATCATTTATGAGTCCTGTACAGTCGGAGAGTCCAACTACATCGACACTTTTAATTA
           K  L  V  N  T  Q  D  M  S  A  S  Q  V  D  V  A  V  K  I  N
                1840                1860                1880
                 .                   .                   .
          AAGAAAGTTGTGCCCCTGGACTTTTCTATGAGTTCTTTAGCTAAACGAATAAAGCAGTTA
          ---+---------+---------+---------+---------+---------+------
          TTCTTTCAACACGGGGACCTGAAAAGATACTCAAGAAATCGATTTGCTTATTTCGTCAAT
           K  K  V  V  P  L  D  F  S  M  S  S  L  A  K  R  I  K  Q  L
                1900                1920                1940
                 .                   .                   .
          CATCATGAAGCACAGCAAAGTGAAGGGGAACAGAATTACAGGAAGTTTAGGGCAAAGATT
          ---+---------+---------+---------+---------+---------+------
          GTAGTACTTCGTGTCGTTTCACTTCCCCTTGTCTTAATGTCCTTCAAATCCCGTTTCTAA
           H  H  E  A  Q  Q  S  E  G  E  Q  N  Y  R  K  F  R  A  K  I
                1960                1980                2000
                 .                   .                   .
          TGTCCTGGAGAAAATCAAGCAGCCGAAGATGAACTAAGAAAAGAGATAAGTAAAACGATG
          ---+---------+---------+---------+---------+---------+------
          ACAGGACCTCTTTTAGTTCGTCGGCTTCTACTTGATTCTTTTCTCTATTCATTTTGCTAC
           C  P  G  E  N  Q  A  A  E  D  E  L  R  K  E  I  S  K  T  M
                2020                2040                2060
                 .                   .                   .
          TTTGCAGAAATGGAAATCATTGGTCAGTTTAACCTGGGATTTATAATAACCAAACTGAAT
          ---+---------+---------+---------+---------+---------+------
          AAACGTCTTTACCTTTAGTAACCAGTCAAATTGGACCCTAAATATTATTGGTTTGACTTA
           F  A  E  M  E  I  I  G  Q  F  N  L  G  F  I  I  T  K  L  N
```

FIG. 3E

```
              2080                2100                2120
                .                   .                   .
                .                   .                   .
         GAGGATATCTTCATAGTGGACCAGCATGCCACGGACGAGAAGTATAACTTCGAGATGCTG
         ---+---------+---------+---------+---------+---------+------
         CTCCTATAGAAGTATCACCTGGTCGTACGGTGCCTGCTCTTCATATTGAAGCTCTACGAC
          E  D  I  F  I  V  D  Q  H  A  T  D  E  K  Y  N  F  E  M  L
            2140                2160                2180
              .                   .                   .
              .                   .                   .
         CAGCAGCACACCGTGCTCCAGGGGCAGAGGCTCATAGCACCTCAGACTCTCAACTTAACT
         ---+---------+---------+---------+---------+---------+------
         GTCGTCGTGTGGCACGAGGTCCCCGTCTCCGAGTATCGTGGAGTCTGAGAGTTGAATTGA
          Q  Q  H  T  V  L  Q  G  Q  R  L  I  A  P  Q  T  L  N  L  T
            2200                2220                2240
              .                   .                   .
              .                   .                   .
         GCTGTTAATGAAGCTGTTCTGATAGAAAATCTGGAAATATTTAGAAAGAATGGCTTTGAT
         ---+---------+---------+---------+---------+---------+------
         CGACAATTACTTCGACAAGACTATCTTTTAGACCTTTATAAATCTTTCTTACCGAAACTA
          A  V  N  E  A  V  L  I  E  N  L  E  I  F  R  K  N  G  F  D
            2260                2280                2300
              .                   .                   .
              .                   .                   .
         TTTGTTATCGATGAAAATGCTCCAGTCACTGAAAGGGCTAAACTGATTTCCTTGCCAACT
         ---+---------+---------+---------+---------+---------+------
         AAACAATAGCTACTTTTACGAGGTCAGTGACTTTCCCGATTTGACTAAAGGAACGGTTGA
          F  V  I  D  E  N  A  P  V  T  E  R  A  K  L  I  S  L  P  T
            2320                2340                2360
              .                   .                   .
              .                   .                   .
         AGTAAAAACTGGACCTTCGGACCCCAGGACGTCGATGAACTGATCTTCATGCTGAGCGAC
         ---+---------+---------+---------+---------+---------+------
         TCATTTTTGACCTGGAAGCCTGGGGTCCTGCAGCTACTTGACTAGAAGTACGACTCGCTG
          S  K  N  W  T  F  G  P  Q  D  V  D  E  L  I  F  M  L  S  D
            2380                2400                2420
              .                   .                   .
              .                   .                   .
         AGCCCTGGGGTCATGTGCCGGCCTTCCCGAGTCAAGCAGATGTTTGCCTCCAGAGCCTGC
         ---+---------+---------+---------+---------+---------+------
         TCGGGACCCCAGTACACGGCCGGAAGGGCTCAGTTCGTCTACAAACGGAGGTCTCGGACG
          S  P  G  V  M  C  R  P  S  R  V  K  Q  M  F  A  S  R  A  C
             2440                2460                2480
              .                   .                   .
              .                   .                   .
         CGGAAGTCGGTGATGATTGGGACTGCTCTTAACACAAGCGAGATGAAGAAACTGATCACC
         ---+---------+---------+---------+---------+---------+------
         GCCTTCAGCCACTACTAACCCTGACGAGAATTGTGTTCGCTCTACTTCTTTGACTAGTGG
          R  K  S  V  M  I  G  T  A  L  N  T  S  E  M  K  K  L  I  T
```

FIG. 3F

```
               2500                2520                2540
                 .                   .                   .
         .         .         .         .         .         .
    CACATGGGGGAGATGGACCACCCCTGGAACTGTCCCCATGGAAGGCCAACCATGAGACAC
    ---+---------+---------+---------+---------+---------+------
    GTGTACCCCCTCTACCTGGTGGGGACCTTGACAGGGGTACCTTCCGGTTGGTACTCTGTG
      H  M  G  E  M  D  H  P  W  N  C  P  H  G  R  P  T  M  R  H
               2560                2580                2600
                 .                   .                   .
         .         .         .         .         .         .
    ATCGCCAACCTGGGTGTCATTTCTCAGAACTGACCGTAGTCACTGTATGGAATAATTGGT
    ---+---------+---------+---------+---------+---------+------
    TAGCGGTTGGACCCACAGTAAAGAGTCTTGACTGGCATCAGTGACATACCTTATTAACCA
      I  A  N  L  G  V  I  S  Q  N  *
               2620                2640                2660
                 .                   .                   .
         .         .         .         .         .         .
    TTTATCGCAGATTTTTATGTTTTGAAAGACAGAGTCTTCACTAACCTTTTTTGTTTTAAA
    ---+---------+---------+---------+---------+---------+------
    AAATAGCGTCTAAAAATACAAAACTTTCTGTCTCAGAAGTGATTGGAAAAAACAAAATTT
               2680                2700                2720
                 .                   .                   .
         .         .         .         .         .         .
    ATGAAACCTGCTACTTAAAAAAAATACACATCACACCCATTTAAAAGTGATCTTGAGAAC
    ---+---------+---------+---------+---------+---------+------
    TACTTTGGACGATGAATTTTTTTATGTGTAGTGTGGGTAAATTTTCACTAGAACTCTTG
                 2740
                   .
         .        .
    CTTTTCAAACC
    ---+--------
    GAAAAGTTTGG

FIG. 3G
```

```
YPMS1  mfhhienllietekrckqkegryipvkylfsmtqIHQINDIDVHRITSGQVITDLTTAVKELVDNSIDANANQIEIIFKD
HMLH2  ------------------------------------MKQLPAATVRLLSSQITSVVKELIENSLDAGATSVDVKLEN
HMLH3  meraesstepaka----------------------IKPIDRKSVHQICSGQVVLSLSTAVKELVENSLDAGATNIDLKLKD YPMS1  YGLESIECSDNGDGIDPSNYEFLALKHYTSKIAKFQDVAKVQTLGFRGEALSICGIAKLSVITTSPPK-ADKLEYDMV
HMLH2  YGFDKIEVRDNGEGIKAVDAPVMAMKYYTSKINSHEDLENLTTYGFRGEALGSICCIAEVLITTRTAADNFSTQYVLDGS
HMLH3  YGVDLIEVSDNGCVEENFEGLTLKHHTSKIQEFADLTQVETFGFRGEALSSLCALSDVTISTCHASAKVGTRLMFDHN YPMS1  GHITSKTTTSRNKGTTVLVSQLFHNLPVRQKEFSKTfkrqftkcltviqgyalinaaikfsvwnitpkgkknlilstmrn
HMLH2  GHILSQKPSHLGQGTTVTALRLFKNLPVRKQFYSTAkkckdeikkiqdllmsfgilkpdlrivfvhnkaviwqksrvsdh
HMLH3  GKIIQKTPYPRPRGTTVSVQQLFSTLPVRHKEFQRNikeyakmvqvlhayclisagirvsctnqlgqgkrqpvvctggs YPMS1  ssmrknissvfgaggmrgleevdlvldlnpfknrmlgkytddpdfldldykirvkgyisqnsfgcgrNSKDRQFIYVNKR
HMLH2  kmalmsylgtavmnnmesfqyhseesqiylsgflpkcdadhsfts1---------------STPERSFIFINSR
HMLH3  psikenigsvfggkqlqslipfvqlppsdsvceeyglscsdalhnlfyisgfisqcthgvgr----SSTDRQFFFINRR
```

FIG. 4A

```
YPMS1  PVEYSTLLKCCNEVYKTFNNVQ----FPAVFLNLELPMSLIDVNVTPDKRVILLHNERAVIDIFKTTLSDYYNrqelalp
HMLH2  PVHQKDILKLIRHHYNLKCLKESTRLYPVFFLKIDVPTADVDVNLTPDKSQVLLQNKESVLIALENLMTTCYGplpstns
HMLH3  PCDPAKVCRLVNEVYHMYNRHQ----YPFVVLNISVDSECVDINVTPDKRQILLQEEKLLAVLKTSLIGMFDsdvnkln YPMS1  krmcsqseqqaqkrlktevfddrstthesdnenyhtarsesngsnhahfnsttgvidksngteltsvmdgnytnvtdvig
HMLH2  yennktdvsaadivlsktaetdvlfnkvessgknysnvdtsvipfqndmhndesgkntddclnhqisigdfgyghcssei
HMLH3  vsqqplldvegnlikmhaadlekpmvekqdqspslrtgeekkdvsisrlreafslrhttenkphspktpeprrsplgkkr YPMS1  secevsvdssvvldegnsstptkklpsiktdsqnlsdlnlnnfsnpefqnitspdkarslekvveepvyfdidgekfqek
HMLH2  snidkntknafqdismsnvswensqteysktcfissvkhtqsengnkdhidesgeneeeaglensseisadewsrgnilk
HMLH3  gmlsststsgaisdkgvlrpqkeavssshgpsdptdraevekdsghgstsvdsegfsipdtgshcsseyaasspgdrgsqe YPMS1  avlsqadglvfvdnechehtndcchgerrgstdteqddeadsiyaeiepveinvrtplknsrksiskdnyrslsdglthr
HMLH2  nsvgeniepvkilvpekslpckvsnnnypipeqmnlnedscnkksnvidnksgkvtaydllsnrvikkpmsasalfvqdh
HMLH3  hvdsqekapetddsfsdvdchsnqedtgckfrvlpqptnlatpntkrfkkeeilssdicqklvntqdmsasqvdvavki
```

FIG. 4B

```
YPMS1  kfedeileynlstknfkeiskngkqmssiiskrkseageniiknkdeledfeggekyltltvsknfdfkkmevvgqfnlgf
HMLH2  rpqflienpktsledatlqieelwktlseeeklkyeekatkdlerynsqmkraiegesqmslkdgrkkikptsawnlaqk
HMLH3  nkkvvpldfsmsslakrikqlhheaggsegegnyrkfrakicpgengaaedelrkeisktmfaemeiggfnlgfiiitkl YPMS1  iivtrkvdnksdlfivdqhasdekynfetlgavtvfksgkliipqpvvelsvidelvvldnlpvfekngfklkideeefg
HMLH2  hklktslsnqpkldellqsqiekrrsqnikmvqipfsmknlkinfkkgnkvdleekdepclihnlrfpdawlmtsktevm
HMLH3  nedifivdqhatdekynfemlqqhtvlqqrliapqtlnltavneavlienleifrkngfdfvidenapvteraklislp YPMS1  srvkllslptskqtlfdlgdfnelihlikedgglrrdni----------------------------------------
HMLH2  llnpyrveeallfkrllenhklpaeplekpimlteslfngshyldvlykmtaddqrysgstylsdprltangfkiklipg
HMLH3  tsknwtfgpqdvdelifmlsdspgvmc----------------------------------------------------

YPMS1  ------------------------------------------RCSKIRSMFAMRACRSSIMIGKPLNKKTMTRVVHNLs
HMLH2  vsitenyleiegmanclpfygvadlkeilnailnrnakevyecRPRKVISYLEGEAVRLSRQLPMYLSKEDIQDIIYRMk
HMLH3  ------------------------------------------RPSRVKQMFASRACRKSVMIGTALNTSEMKKLITHMg YPMS1  eldkpw--NCPHGRPTMRHLMEIrdwssfskdyei
HMLH2  hqfgneikECVHGRPFFHHLTYLpett-------
HMLH3  emdhpw--NCPHGRPTMRHIANLgvisqn-----
```

FIG. 4C

HUMAN DNA MISMATCH REPAIR PROTEINS

This application is a continuation-in-part of application Ser. No. 08/210,143 filed Mar. 16, 1994 which is a continuation-in-part of Ser. No. 08/187,757, filed Jan. 27, 1994 both of which are pending.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human homologs of the prokaryotic mutL4 gene and are hereinafter referred to as HMLH1, HMLH2 and HMLH3.

In both procaryotes and eucaryotes, DNA mismatch repair plays a prominent role in the correction of errors made during DNA replication and genetic recombination. The *E. coli* methyl-directed DNA mismatch repair system is the best understood DNA mismatch repair system to date. In *E. coli*, this repair pathway involves the products of the mutator genes mutS, mutL, mutH, and uvrD. Mutants of any one of these genes will reveal a mutator phenotype. MutS is a DNA mismatch-binding protein which initiates this repair process, uvrD is a DNA helicase and MutH is a latent endonuclease that incises at the unmethylated strands of a hemi-methylated GATC sequence. MutL protein is believed to recognize and bind to the mismatch-DNA-MutS-MutH complex to enhance the endonuclease activity of MutH protein. After the unmethylated DNA strand is cut by the MutH, single-stranded DNA-binding protein, DNA polymerase III, exonuclease I and DNA ligase are required to complete this repair process (Modrich P., Annu. Rev. Genetics, 25:229–53 (1991)).

Elements of the *E. coli* MutLHS system appears to be conserved during evolution in procaryotes and eucaryotes. Genetic study analysis suggests that *Saccharomyces cerevisiae* has a mismatch repair system similar to the bacterial MutLHS system. In *S. cerevisiae,* at least two MutL homologs, PMS1 and MLH1, have been reported. Mutation of either one of them leads to a mitotic mutator phenotype (Prolla et al, Mol. Cell. Biol. 14:407–415 [1994]). At least three MutS homologs have been found in *S. cerevisiae*, namely MSH1, MSH2, and MSH3. Disruption of the msh2 gene affects nuclear mutation rates. Mutants in *S. cerevisae*, msh2, pms1, and mlh1 have been found to exhibit increased rates of expansion and contraction of dinucleotide repeat sequences (Strand et al., Nature, 365:274–276 (1993)).

It has been reported by various laboratories that a number of human tumors such as lung cancer, prostate cancer, ovarian cancer, breast cancer, colon cancer and stomach cancer show instability of repeated DNA sequences (Han et al., Cancer, 53:5087–5089 [1993]; Thibodeau et al., *Science* 260:816–819 [1993]; Risinger et al., Cancer 53:5100–5103 [1993]). This phenomenon suggests that lack of the DNA mismatch repair is probably the cause of these tumors. Little was known about the DNA mismatch repair system in humans until recently, the human homolog of the MutS gene was cloned and found to be responsible for hereditary nonpolyposis colon cancer (HNPCC), (Fishel et al., Cell, 75:1027–1038 [1993] and Leach et al., Cell, 75:1215–1225 [1993]). HNPCC was first linked to a locus at chromosome 2p16 which causes dinucleotide instability. It was then demonstrated that a DNA mismatch repair protein (MutS) homolog was located at this locus, and that C→T transitional mutations at several conserved regions were specifically observed in HNPCC patients. Hereditary nonpolyposis colorectal cancer is one of the most common hereditable diseases of man, affecting as many as one in two hundred individuals in the western world.

It has been demonstrated that hereditary colon cancer can result from mutations in several loci. Familial adenomatosis polyposis coli (APC), linked to a gene on chromosome 5, is responsible for a small minority of hereditary colon cancer. Hereditary colon cancer is also associated with Gardner's syndrome, Turcot's syndrome, Peutz-Jaeghers syndrome and juvenile polyposis coli. In addition, hereditary nonpolyposis colon cancer (HNPCC) may be involved in 5% of all human colon cancer. All of the different types of familial colon cancer have been shown to be transmitted by a dominant autosomal mode of inheritance.

In addition to localization of HNPCC, to the short arm of chromosome 2, a second locus has been linked to a predisposition to HNPCC (Lindholm, et al., Nature Genetics, 5:279–282 (1993)). A strong linkage was demonstrated between a polymorphic marker on the short arm of chromosome 3 and the disease locus. It was also suggested that these families show signs of a general defect in the DNA repair process.

This finding suggests that mutations on various DNA mismatch repair proteins probably play crucial roles in the development of human hereditary diseases and cancers.

HNPCC is characterized clinically by an apparent autosomal dominantly inherited predisposition to cancer of the colon, endometrium and other organs. (Lynch, H. T. et al., *Gastroenterology,* 104:1535–1549 (1993)). Tumors from HNPCC patients are characterized by widespread alterations of simple repeated sequences (microsatellites) (Aaltonen, L. A., et al., *Science,* 260:812–816 (1993)). This type of genetic instability was originally observed in a subset (12 to 18% of sporadic colorectal cancers (Id.). Studies in bacteria and yeast indicated that a defect in DNA mismatch repair genes can result in a similar instability of microsatellites (Levinson, G. and Gutman, G. A., *Nuc. Acids Res.,* 15:5325–5338 (1987)), and it was hypothesized that deficiency in mismatched repair was responsible for HNPCC (Strand, M. et al., *Nature,* 365:274–276 (1993)). Analysis of extracts from HNPCC tumor cell lines showed mismatch repair was indeed deficient, adding definitive support to this conjecture (Parsons, R. P., et al., Cell, 75:1227–1236 (1993)). As not all HNPCC kindred can be linked to the same loci, and as at least three genes can produce a similar phenotype in yeast, it seems likely that other mismatch repair genes could play a role in some cases of HNPCC.

hMLH1 is most homologous to the yeast mutL-homolog yMLH1 while hMLH2 and hMLH3 have greater homology to the yeast mutL-homolog yPMS1 (hMLH2 and hMLH3 due to their homology to yeast PMS1 gene are sometimes referred to in the literature as hPMS1 and hPMS2). Both the hMLH2 gene on chromosome 2q32 and the hMLH3 gene, on chromosome 7p22, were found to be mutated in the germ line of HNPCC patients. This doubles the number of genes implicated in HNPCC and may help explain the relatively high incidence of this disease.

In accordance with one aspect of the present invention, there are provided novel putative mature polypeptides which are hMLH1, hMLH2 and hMLH3, as well as fragments, analogs and derivatives thereof. The polypeptides of the present invention are of human origin.

In accordance with another aspect of the present invention, there are provided polynucleotides (DNA or RNA) which encode such polypeptides.

In accordance with yet a further aspect of the present invention there is provided a process for producing such polypeptides by recombinant techniques.

In accordance with yet a further aspect of the present invention, there is provided a process for utilizing such polypeptide, or polynucleotide encoding such polypeptide, for therapeutic purposes, for example, for diagnostic and therapeutic purposes.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is the cDNA sequence (SEQ ID NO:1) and deduced amino acid sequence (SEQ ID NO:2) for the human DNA repair protein hMLH1. The amino acids are represented by their standard one-letter abbreviations.

FIG. 2. Structure of human hMLH2. The cDNA sequence (SEQ ID NO:3) and corresponding deduced amino acid sequence (SEQ ID NO:4) of the putative mature hMLH2.

FIG. 3. Structure of human hMLH3. The cDNA sequence (SEQ ID NO:5) and corresponding deduced amino acid sequence (SEQ ID NO:6) of the putative mature polypeptide hMLH3.

FIG. 4. Alignment of the predicted amino acid sequences of *S. cerevisiae* PMS1 (yPMS1), with the hMLH2 and hMLH3 amino acid sequences using MACAW (version 1.0) program. Amino acid in conserved blocks are capitalized and shaded on the mean of their pair-wise scores.

DESCRIPTION OF THE INVENTION

Figure 5A:
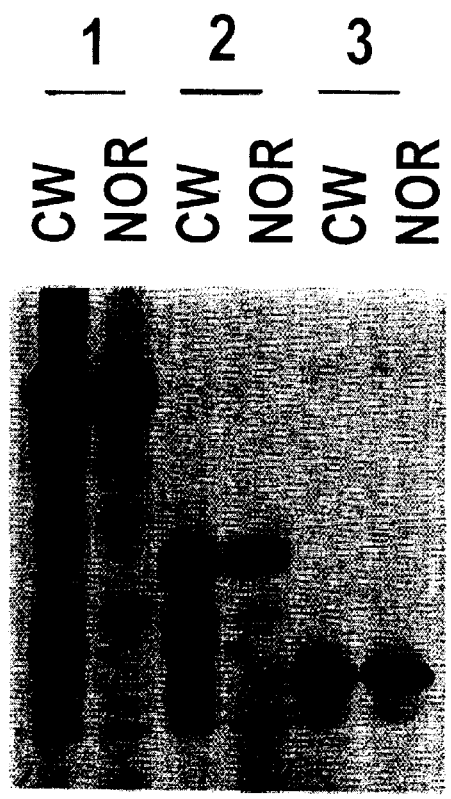
FIG. 5. Mutational analysis of hMLH2. (A) IVSP analysis and mapping of the transcriptional stop mutation in HNPCC patient CW. Translation of codons 1 to 369 (lane 1), codons 1 to 290 (lane 2), and codons 1 to 214 (lane 3). CW is translated from the cDNA of patient CW, while NOR was translated from the cDNA of a normal individual. The arrowheads indicate the truncated polypeptide due to the potential stop mutation. The arrows indicate molecular weight markers in kilodaltons. (B) Sequence analysis of CW indicates a C to T transition at codon 233 (indicated by the arrow). Lanes 1 and 3 are sequence derived from control patients; lane 2 is sequence derived from genomic DNA of CW. The ddA mixes from each sequencing mix were loaded in adjacent lanes to facilitate comparison as were those for ddC, ddG, and ddT mixes.

In accordance with an aspect of the present invention, there are provided isolated nucleic acids (polynucleotides) which encode for the mature polypeptides having the deduced amino acid sequence of FIGS. 1, 2 and 3 (SEQ ID NOS:2, 4 and 6, respectively) or for the mature polypeptides encoded by the cDNA of the clone deposited as ATCC Deposit No. 75649, 75651, 75650, deposited on Jan. 25, 1994.

ATCC Deposit No. 75649 is a cDNA clone which contains the full length sequence encoding the human DNA repair protein referred to herein as hMLH1 (SEQ ID NO:2); ATCC Deposit No. 75651 is a cDNA clone containing the full length cDNA sequence encoding the human DNA repair protein referred to herein as hMLH2 (SEQ ID NO:4); ATCC Deposit No. 75650 is a cDNA clone containing the full length DNA sequence referred to herein as hMLH3 (SEQ ID NO:6). The address of the American Type Culture Collection (ATCC) Depository referred to herein is: American Type Culture Collection, 10801 University Boulevard, Manassas, Va. 20110-2209.

Polynucleotides encoding the polypeptides of the present invention may be obtained from one or more libraries prepared from heart, lung, prostate, spleen, liver, gallbladder, fetal brain and testes tissues. The polynucleotides of hMLH1 were discovered from a human gallbladder cDNA library. In addition, six cDNA clones which are identical to the hMLH1 at the N-terminal ends were obtained from human cerebellum, eight-week embryo, fetal heart, HSC172 cells and Jurket cell cDNA libraries. The hMLH1 gene contains an open reading frame of 756 amino acids encoding for an 85 kD protein which exhibits homology to the bacterial and yeast mutL protein. However, the 5' non-translated region was obtained from the cDNA clone obtained from the fetal heart for the purpose of extending the non-translated region to design the oligonucleotides.

The hMLH2 gene was derived from a human T-cell lymphoma cDNA library. The hMLH2 cDNA clone identified an open reading frame of 2,796 base pairs flanked on both sides by in-frame termination codons. It is structurally related to the yeast PMS1 family. It contains an open reading frame encoding a protein of 932 amino acid residues. The protein exhibits the highest degree of homology to yeast PMS1 with 27% identity and 82% similarity over the entire protein. It is also important that the GFRGEAL domain which is preferably conserved in mutL homologs derived from *E. coli* in human is conserved in the amino acid sequence of hMLH2. A second region of significant homology among the three PMS related proteins is in the carboxyl terminus, between codons 800 to 900. This region shares a 22% and 47% homology between yeast PMS1 protein and hMLH2 and hMLH3 proteins, respectively, while very little homology of this region was observed between these proteins, and the other yeast mutL homolog, yMLH1.

The hMLH3 gene was derived from a human endometrial tumor cDNA library. The hMLH3 clone identified a 2,586 base pair open reading frame. It is structurally related to the yPMS2 protein family. It contains an open reading frame encoding a protein of 862 amino acid residues. The protein exhibits the highest degree of homology to yPMS2 with 32% identity and 66% similarity over the entire protein. It is also important that the GFRGEAL domain which is preferably conserved in mutL homologs derived from *E. coli* in human is conserved in the amino acid sequence of hMLH3.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1, 2 and 3 (SEQ ID NOS:1, 3, and 5, respectively) or that of the deposited clone or may be a different coding sequence which coding sequence, as a result of the redundancy or degeneracy of the genetic code, encodes the same mature polypeptides as the DNA of FIGS. 1, 2 and 3 (SEQ ID NOS: 2, 4 and 6, respectively) or the deposited cDNA(s).

The polynucleotides which encode for the mature polypeptides of FIGS. 1, 2 and 3 or for the mature polypeptides encoded by the deposited cDNAs may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptides having the deduced amino acid sequences of FIGS. 1, 2 and 3 (SEQ ID NOS: 2, 4 and 6, respectively) or the polypeptides encoded by the cDNA of the deposited clones. The variants of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1, 2 and 3 (SEQ ID NOS: 2, 4 and 6, respectively) or the same mature polypeptides encoded by the cDNA of the deposited clones as well as variants of such polynucleotides which variants encode for a fragment, derivative or analog of the polypeptides of FIGS. 1, 2 and 3 (SEQ ID NOS: 2, 4 and 6, respectively) or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIGS. 1, 2 and 3 (SEQ ID NOS:1, 3 and 5, respectively) or of the coding sequence of the deposited clones. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved, an active mature protein remains.

Thus for example, the polynucleotides of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1, 2 and 3 (SEQ ID NO:1, 3 and 5, respectively) or the deposited cDNA(s).

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polypeptides which have the deduced amino acid sequence of FIGS. 1, 2 and 3 (SEQ ID NOS:2, 4 and 6, respectively) or which have the amino acid sequence encoded by the deposited cDNA(s), as well as fragments, analogs and derivatives of such polypeptides.

The terms "fragment," "derivative" and "analog" when referring to the polypeptides of FIGS. 1, 2 and 3 or that encoded by the deposited cDNA(s), means polypeptides which retain essentially the same biological function or activity as such polypeptides. Thus, an analog includes a proprotein which can be activated by cleavage of the proprotein portion to produce an active mature polypeptide.

The polypeptides of the present invention may be a recombinant polypeptide, a natural polypeptide or a synthetic polypeptide, preferably a recombinant polypeptide.

The fragment, derivative or analog of the polypeptides of FIGS. 1, 2 and 3 (SEQ ID NOS:2, 4 and 6, respectively) or that encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol) or (iv) one in which the additional amino acids are fused to the mature polypeptide, such as a leader or secretory sequence which is employed for purification of the mature polypeptides or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hMLH1, hMLH2 and hMLH3 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the proteins. As representative examples of appropriate hosts, there may be mentioned: bacterial cells, such as $E.$ $coli$, Streptomyces, $Salmonella$ $typhimurium;$ fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

DNA mismatch can be generated during DNA replication and recombination. If these mutations were left unrepaired, mutated protein would result in altered or lost function of the normal protein. It has been found, for example, mutation of the human DNA mismatch repair gene hMLH2 is responsible for the hereditary non-polyposis colon cancer (Fishel et al., Cell, 75:1027–1038 (1993) and Leach et al., Cell, 75:1215–1225 (1993)).

In accordance with a further aspect of the invention, there is provided a process for determining susceptibility to cancer, in particular, a hereditary cancer. Thus, a mutation in a human repair protein, which is a human homolog of mutL and in particular those described herein, indicates a susceptibility to cancer, and the nucleic acid sequences encoding such human homologs may be employed in an assay for ascertaining such susceptibility. Thus, for example, the assay may be employed to determine a mutation in a human DNA repair protein as herein described, such as a deletion, truncation, insertion, frame shift, etc., with such mutation being indicative of a susceptibility to cancer.

A mutation may be ascertained for example, by a DNA sequencing assay. Tissue samples including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of 15 to 30 and preferably from 18 to 25 consecutive bases of the human DNA repair gene. Table 1 sets forth an illustrative example of oligonucleotide primer sequences based on hMLH1. The primers are used in pairs (one "sense" strand and one "anti-sense") to amplify the cDNA from the patients by the PCR method such that three overlapping fragments of the patient's cDNA's for such protein are generated. Table 1 also shows a list of preferred primer sequence pairs. The overlapping fragments are then subjected to dideoxynucleotide sequencing using a set of primer sequences synthesized to correspond to the base pairs of the cDNA's at a point approximately every 200 base pairs throughout the gene. Table 2 lists representative examples of oligonucleotide primer sequences (sense and anti-sense) which may be used, and preferably the entire set of primer sequences are used, for sequencing to determine where a muation in the patient DNA repair protein may be. The primer sequences may be from 15 to 30 bases in length and are preferably between 18 and 25 bases in length. The sequence information determined from the patient is then compared to non-mutated sequences to determine if any muations are present.

TABLE 1

Primer Sequences used to amplify gene region using PCR

| Name | SEQ ID NO: | Start Site and Arrangement | Sequence |
|---|---|---|---|
| 758 | 7 | sense-(-41) | GTTGAACATCTAGACGTCTC |
| 1319 | 8 | sense-8 | TCGTGGCAGGGGTTATTCG |
| 1321 | 9 | sense-619 | CTACCCAATGCCTCAACCG |
| 1322 | 10 | sense-677 | GAGAACTGATAGAAATTGGATG |
| 1314 | 11 | sense-1548 | GGGACATGAGGTTCTCCG |
| 1323 | 12 | sense-1593 | GGGCTGTGTGAATCCTCAG |
| 773 | 13 | anti-53 | CGGTTCACCACTGTCTCGTC |
| 1313 | 14 | anti-971 | TCCAGGATGCTCTCCTCG |
| 1320 | 15 | anti-1057 | CAAGTCCTGGTAGCAAAGTC |
| 1315 | 16 | anti-1760 | ATGGCAAGGTCAAAGAGCG |
| 1316 | 17 | anti-1837 | CAACAATGTATTCAGXAAGTCC |
| 1317 | 18 | anti-2340 | TTGATACAACACTTTGTATCG |
| 1318 | 19 | anti-2415 | GGAATACTATCAGAAGGCAAG |

*Numbers corresponding to location along nucleotide sequence of Figure 1 where ATG is number 1.
Preferred primer sequences pairs:
758, 1313
1319, 1320
660, 1909
725, 1995
1680, 2536
1727, 2610

The nucleotide sequences shown in Table 1 represent SEQ ID NOS:7 through 19, respectively.

TABLE 2

Primer Sequences Used to Sequence the Amplified Fragments

| Name | SEQ ID NO: | Start Site and Arrangement | Sequence |
|---|---|---|---|
| 5282 | 20 | sense-377 | ACAGAGCAAGTTACTCAGATG |
| 5283 | 21 | sense-552 | GTACACAATGCAGGCATTAG |
| 5284 | 22 | sense-904 | AATGTGGATGTTAATGTGCAC |

TABLE 2-continued

Primer Sequences Used to Sequence the Amplified Fragments

| Name | SEQ ID NO: | Start Site and Arrangement | Sequence |
|---|---|---|---|
| 5285 | 23 | sense-1096 | CTGACCTCGTCTTCCTAC |
| 5286 | 24 | sense-1276 | CAGCAAGATGAGGAGATGC |
| 5287 | 25 | sense-1437 | GGAAATGGTGGAAGATGATTC |
| 5288 | 26 | sense-1645 | CTTCTCAACACCAAGC |
| 5289 | 27 | sense-1895 | GAAATTGATGAGGAAGGGAAC |
| 5295 | 28 | sense-1921 | CTTCTGATTGACAACTATGTGC |
| 5294 | 29 | sense-2202 | CACAGAAGATGGAAATATCCTG |
| 5293 | 30 | sense-2370 | GTGTTGGTAGCACTTAAGAC |
| 5291 | 31 | anti-525 | TTTCCCATATTCTTCACTTG |
| 5290 | 32 | anti-341 | GTAACATGAGCCACATGGC |
| 5292 | 33 | anti-46 | CCACTGTCTCGTCCAGCCG |

*Numbers corresponding to location along nucleotide sequence of Figure 1 where ATG is number 1.

The nucleotide sequences shown in Table 2 represent SEQ ID NOS:20 through 33, respectively.

In another embodiment, the primer sequences from Table 2 could be used in the PCR method to amplify a mutated region. The region could be sequenced and used as a diagnostic to predict a predisposition to such mutated genes.

Alternatively, the assay to detect mutations in the hMLH1 gene may be performed by generating cDNA from the RNA and expressing the protein encoded by the cDNA by in vitro transcription and translation (see example 4 and 7). The expressed protein may then be analyzed by electrophoresis on SDS, polyacrylamide or other gel. Also electrophoresed is a "normal" gene product. The gel is then dried and subjected to autoradiography and the suspected muatted gene product and "normal" gene product are analyzed and any differences in the banding pattern is indicative of a mutation in the cDNA. The gene product can also be detected by using antibodies against the particular gene by Western Blot analysis.

Accordingly, the mutations in the genes of the present invention may be determined directly by sequencing or indirectly by examining an expressed protein.

The polypeptides may also be employed in accordance with the present invention by expressing of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Each of the cDNA sequences identified herein or a portion thereof can be used in numerous ways as polynucleotide reagents. The sequences can be used as diagnostic probes for the presence of a specific mRNA in a particular cell type. In addition, these sequences can be used as diagnostic probes suitable for use in genetic linkage analysis (polymorphisms).

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2000 bp have a higher likelihood of binding to unique chromosomal location with sufficient sugnal intensity for simple detection. FISH requires use of the clones from which the EST was derived, and the longer the better. For example, 2000 bp is good, 4000 is better, and more than 4000 is probably not necessary to get good results a reasonable percentage of the time. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

hMLH2 has been localized using a genomic P1 clone (1670) which contained the 5' region of the hMLH2 gene. Detailed analysis of human metaphase chromosome spreads, counterstained to reveal banding, indicated that the hMLH2 gene was located within bands 2q32. Likewise, hMLH3 was localized using a genomic P1 clone (2053) which contained the 3' region of the hMLH3 gene. Detailed analysis of human metaphase chromosome spreads, counterstained to reveal banding, indicated that the hMLH3 gene was located within band 7p22, the most distal band on chromosome 7. Analysis with a variety of genomic clones showed that hMLH3 was a member of a subfamily of related genes, all on chromosome 7.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 •g of plasmid or DNA fragment is used with about 2 units of enzyme in about 20 •1 of buffer solution. For the purpose of isolating DNA fragments for plasmid construction, typically 5 to 50 •g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 •g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression of hMLH1

The full length DNA sequence encoding for human DNA mismatch repair protein hMLH1, ATCC # 75649, is initially amplified using PCR oligonucleotide primers corresponding to the 5' and 3' ends of the DNA sequence to synthesize insertion fragments. The 5' oligonucleotide primer has the sequence 5'-CGGGATCCATGTCGTTCGTGGCAGGG-3' (SEQ ID NO:34), contains a BamHI restriction enzyme site followed by 18 nucleotides of hMLH1 coding sequence following the initiation codon; the 3' sequence 5'-GCTCTAGATTAACACCTCTCAAAGAC-3' (SEQ ID NO:35) contains complementary sequences to an XbaI site and is at the end of the gene. The restriction enzyme sites correspond to the restriction enzyme sites on the bacterial expression vector pQE-9 (Qiagen, Inc. 9259 Eton Avenue, Chatsworth, Calif., 91311). The plasmid vector encodes antibiotic resistance (Amp$^r$), a bacterial origin of replication (ori), an IPTG-regulatable promoter/operator (P/O), a ribosome binding site (RBS), a 6-histidine tag (6-His) and restriction enzyme cloning sites. The pQE-9 vector was digested with BamHI and XbaI and the insertion fragments were then ligated into the pQE-9 vector maintaining the reading frame initiated at the bacterial RBS. The ligation mixture was then used to transform the E. coli strain GW3733 (k12, argE3 hisG4,LeuB6 proA2 thr-1 ara-1 rpsL31 supE44 tsx-33 mut1218::Tn10). Transformants are identified by their ability to grow on LB plates containing Amp.

Clones containing the desired constructs were grown overnight (O/N) in liquid culture in LB media supplemented with Amp (100 mg/ml). Tho O/N culture is used to inoculate a large culture at a ratio of 1:100 to 1:250. The cells were grown to an optical density 600 nm (O.D.$^{600}$) of between 0.4 and 0.6. Cells are grown an extra 2–4 hours and then harvested by centrifugation. Expression hMLH1 is tested by solubilizing a portion of the E. coli and analyzing on a SDS polyacrylamide gel. Purification of the protein is accomplished by utilization of the hexa-histidine sequence. Following induction of the E. coli pellet is solubilized in 6M guanidine HCl. The protein is purified using a Nickel-Chelate resin column having a high affinity for the hexa-histidine sequence. (Hachule, E. et al., Genetic Engineering, Principles and Methods, 12:87–98, Plenum Press, NY (1990). The column was washed and the protein is eluted at a pH of 5.0. Protein renaturation is accomplished by removing the guanidine HCl from the protein isolated by any one of several protocols. (Jaenicke, R. et al., Protein Structure—A Practical Approach. IRL Press, New York (1990). The purified protein is analyzed by SDS-PAGE.

EXAMPLE 2

Spontaneous Mutation Assay for Detection of the Expression of hMLH1, hMLH2 and hMLH3 and Complementation to the E. coli mut1

The pQE9hMLH1, pQE9hMLH2 or pQE9hMLH3/GW3733, transformants were subjected to the spontaneous mutation assay. The plasmid vector pQE9 was also transformed to AB1157 (k-12, argE3 hisG4,LeuB6 proA2 thr-1 ara-1 rpsL31 supE44 tsx-33) and GW3733 to use as the positive and negative control respectively.

Fifteen 2 ml cultures, inoculated with approximately 100 to 1000 E. coli, were grown 2×10$^8$ cells per ml in LB ampicillin medium at 37° C. Ten microliters of each culture were diluted and plated on the LB ampicillin plates to measure the number of viable cells. The rest of the cells from each culture were then concentrated in saline and plated on minimal plates lacking of arginine to measure reversion of Arg$^+$. The mean number of mutations per culture (m) was calculated from the median number (r) of mutants per distribution, according to the equation (r/m)−ln(m)=1.24 (Lea et al., J. Genetics 49:264–285 [1949]). Mutation rates per generation were recorded as m/N, with N representing the average number of cells per culture.

TABLE 3

| Spontaneous Mutation Rates | |
|---|---|
| Strain | Mutation/generation |
| AB1157 + vector | (5.6 ± 0.1) × 10-9a |
| GW3733 + vector | (1.1 ± 0.2) × 10-6a |
| GW3733 + phMLH1 | (3.7 ± 1.3) × 10-7a |
| GW3733 + phMLH2 | (3.1 ± 0.6) × 10-7b |
| GW3733 + phMLH3 | (2.1 ± 0.8) × 10-7b | a: Average of three experiments.
b: Average of four experiments.

The functional complementation result showed that the human mutL can partially rescue the E. coli mutL mutator phenotype, suggesting that the human mutL can not only express but also function in bacteria.

17

EXAMPLE 3

Chromosomal Mapping of the hMLH1

An oligonucleotide primer set was designed according to the sequence at the 5' end of the cDNA for hMLH1. This primer set would span a 94 bp segment. This primer set was used in a polymerase chain reaction under the following set of conditions:

30 seconds, 95 degrees C.

1 minute, 56 degrees C.

1 minute, 70 degrees C.

This cycle was repeated 32 times followed by one 5 minute cycle at 70 degrees C. Human, mouse, and hamster DNA were used as template in addition to a somatic cell hybrid panel (Bios, Inc). The reactions were analyzed on either 8% polyacrylamide gels or 3.5% agarose gels. A 94 base pair band was observed in the human genomic DNA sample and in the somatic cell hybrid sample corresponding to chromosome 3. In addition, using various other somatic cell hybrid genomic DNA, the hMLH1 gene was localized to chromosome 3p.

EXAMPLE 4

Method for Determination of Mutation of hMLH1 Gene in HNPCC Kindred cDNA was produced from RNA obtained from tissue samples from persons who are HNPCC kindred and the cDNA was used as a template for PCR, employing the primers 5'-GCATCTAGACGTTTCCTTGGC-3' (SEQ ID NO:36) and 5'-CATCCAAGCTTCTGTTCCCG-3' (SEQ ID NO:37), allowing amplification of codons 1 to 394 of FIG. 1; 5'-GGGGTGCAGCAGCACATCG-3' (SEQ ID NO:38) and 5'-GGAGGCAGAATGTGTGAGCG-3' (SEQ ID NO:39), allowing amplification of codons 326 to 729 of FIG. 1; and 5'-TCCCAAAGAAGGACTTGCT-3' (SEQ ID NO:40) and 5'-AGTATAAGTCTTAAGTGCTACC-3' (SEQ ID NO:41), allowing amplification of codons 602 to 756 plus 128 nt of 3'-untranslated sequences of FIG. 1. The PCR conditions for all analyses used consisted of 35 cycles at 95° C. for 30 seconds, 52–58° C. for 60 to 120 seconds, and 70° C. for 60 to 120 seconds, in the buffer solution described in San Sidransky, D. et al., Science, 252:706 (1991). PCR products were sequenced using primers labeled at their 5' end with T4 polynucleotide kinase, employing SequiTherm Polymerase (Epicentre Technologies). The intron-exon borders of selected exons were also determined and genomic PCR products analyzed to confirm the results. PCR products harboring suspected mutations were then cloned and sequenced to validate the results of the direct sequencing. PCR products were cloned into T-tailed vectors as described in Holton, T. A. and Graham, M. W., Nucleic Acids Research, 19:1156 (1991) and sequenced with T7 polymerase (United States Biochemical). Affected individuals from seven kindreds all exhibited a heterozygous deletion of codons 578 to 632 of the hMLH1 gene. The derivation of five of these seven kindreds could be traced to a common ancestor. The genomic sequences surrounding codons 578–632 were determined by cycle-sequencing of the P1 clones (a human genomic P1 library which contains the entire hMLH1 gene (Genome Systems)) using SequiTherm Polymerase, as described by the manufacturer, with the primers were labeled with T4 polynucleotide kinase, and by sequencing PCR products of genomic DNA. The primers used to amplify the exon containing codons 578–632 were 5'-TTTATGGTTTCTCACCTGCC-3' (SEQ ID NO:42) and 5'-GTTATCTGCCCACCTCAGC03' (SEQ ID NO:43). The PCR product included 105 bp of intron C sequence upstream

18 of the exon and 117 bp downstream. No mutations in the PCR product were observed in the kindreds, so the deletion in the RNA was not due to a simple splice site mutation. Codons 578 to 632 were found to constitute a single exon which was deleted from the gene product in the kindreds described above. This exon contains several highly conserved amino acids.

In a second family (L7), PCR was performed using the above primers and a 4 bp deletion was observed beginning at the first nucleotide (nt) of codon 727. This produced a frame shift with a new stop codon 166 nt downstream, resulting in a substitution of the carboxy-terminal 29 amino acids of hMLH1 with 53 different amino acids, some encoded by nt normally in the 3' untranslated region.

A different mutation was found in a different kindred (L2516) after PCR using the above primers, the mutation consisting of a 4 bp insert between codons 755 and 756. This insertion resulted in a frame shift and extension of the ORF to include 102 nucleotides (34 amino acids) downstream of the normal termination codon. The mutations in both kindreds L7 and L2516 were therefore predicted to alter the C-terminus of hMLH1.

Figure 5B:
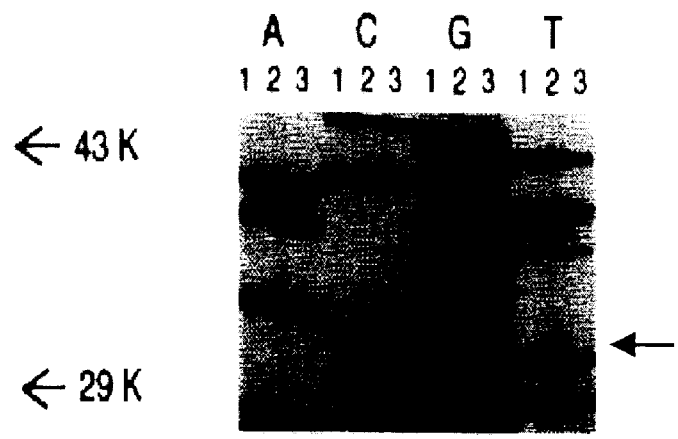
Figure 6A:
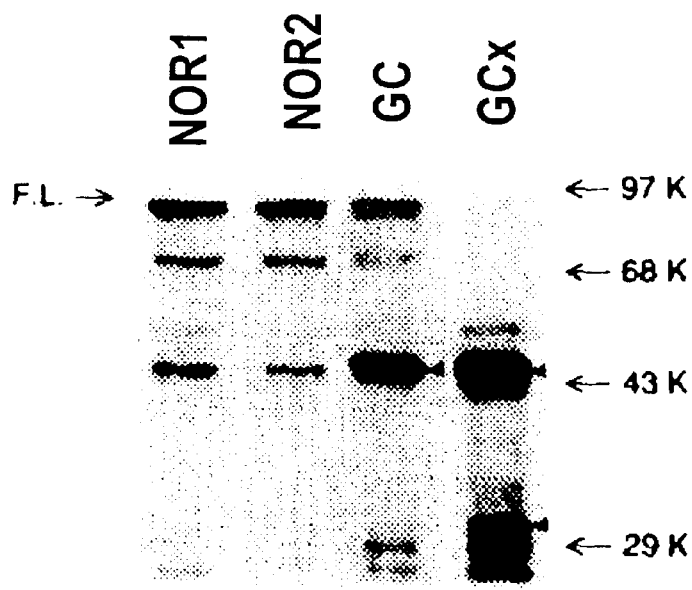
FIG. 6. Mutational analysis of hMLH3. (A) IVSP analysis of hMLH3 from patient GC. Lane GC is from fibroblasts of individual GC; lane GCx is from the tumor of patient GC; lanes NOR1 and 2 are from normal control individuals. FL indicates full-length protein, and the arrowheads indicate the germ line truncated polypeptide. The arrows indicate molecular weight markers in kilodaltons. (B) PCR analysis of DNA from a patient GC shows that the lesion in present in both hMLH3 alleles in tumor cells. Amplification was done using primers that amplify 5', 3', or within (MID) the region deleted in the cDNA. Lane 1, DNA derived from fibroblasts of patient GC; lane 2, DNA derived from tumor of patient GC; lane 3, DNA derived from a normal control patient; lane 4, reactions without DNA template. Arrows indicate molecular weight in base pairs.
Figure 6B:
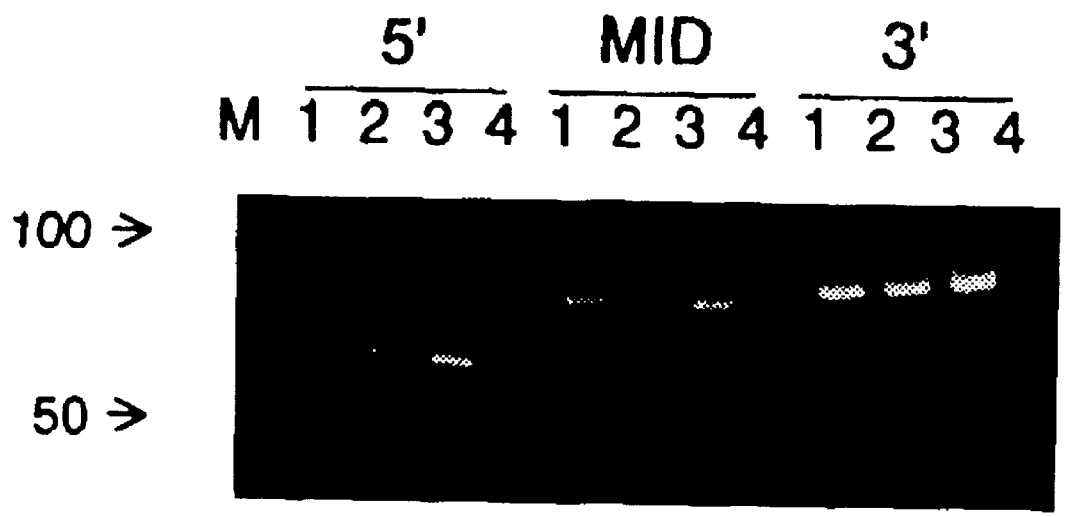

A possible mutation in the hMLH1 gene was determined from alterations in size of the encoded protein, where kindreds were too few for linkage studies. The primers used for coupled transcription-translation of hMLH1 were 5'-GGATCCTAATACGACTCACTATAGGGAGACCACC-ATGGCATCTAGACGTTTCCCTTGGC-3' (SEQ ID NO:44) and 5'-CATCCAAGCTTCTGTTCCCG-3' (SEQ ID NO:45) for codons 1 to 394 of FIG. 1 and 5'-GGATCCTAATACGACTCACTATAGGGAGACCAC-CATGGGGGTGCAGCAGCACATCG-3' (SEQ ID NO:46) and 5'-GGAGGCAGAATGTGTGAGCG-3' (SEQ ID NO:47) for codons 326 to 729 of FIG. 1. The resultant PCR products had signals for transcription by T7 RNA polymerase and for the initiation of translation at their 5' ends. RNA from lymphoblastoid cells of patients from 18 kindreds was used to amplify two products, extending from codon 1 to codon 394 or from codon 326 to codon 729, respectively. The PCR products were then transcribed and translated in vitro, making use of transcription-translation signals incorporated into the PCR primers. PCR products were used as templates in coupled transcription-translation reactions performed as described by Powell, S. M. et al., New England Journal of Medicine, 329:1982, (1993), using 40 micro CI of $^{35}$S labeled methionine. Samples were diluted in sample buffer, boiled for five minutes and analyzed by electrophoresis on sodium dodecyl sulfate-polyacrylamide gels containing a gradient of 10% to 20% acrylamide. The gels were dried and subjected to radiography. All samples exhibited a polypeptide of the expected size, but an abnormally migrating polypeptide was additionally found in one case. The sequence of the relevant PCR product was determined and found to include a 371 bp deletion beginning at the first nt of codon 347. This alteration was present in heterozygous form, and resulted in a frame shift in a new stop codon 30 nt downstream of codon 346, thus explaining the truncated polypeptide observed.

Four colorectal tumor cell lines manifesting microsatellite instability were examined. One of the four (cell line H6) showed no normal peptide in this assay and produced only a short product migrating at 27 kd. The sequence of the corresponding cDNA was determined and found to harbor a C to A transversion at codon 252, resulting in the substitution of a termination codon for serine. In accord with the translational analyses, no band at the normal C position was identified in the cDNA or genomic DNA from this tumor, indicating that it was devoid of a functional hMLH1 gene.

Table 4 sets forth the results of these sequencing assays. Deletions were found in those people who were known to have a family history of the colorectal cancer. More particularly, 9 of 10 families showed an hMLH1 mutation.

TABLE 4

Summary of Mutations in hMLH1

| Sample | Codon | cDNA Nucleotide Change | Predicted Coding Change |
|---|---|---|---|
| Kindreds F2, F3, F6, F8, F10, F11, F52 | 578–632 | 165 bp deletion | In-frame deletion |
| Kindred L7 | 727/728 | 4 bp deletion (TCACACATTC to TCATTCT) | Frameshift and substitution of new amino acids |
| Kindred L2516 | 755/756 | 4 bp insertion (GTGTTAA to GTGTTTGTTAA) | Extension of C-terminus |
| Kindred RA | 347 | 371 bp deletion | Frameshift/ Truncation |
| H6 Colorectal Tumor | 252 | Transversion (TCA to TAA) | Serine to Stop |

EXAMPLE 5

Bacterial Expression and Purification of hMLH2

The DNA sequence encoding for hMLH2, ATCC #75651, is initially amplified using PCR oligonucleotide primers corresponding to the 5' end and 3' end. Additional nucleotides corresponding to hMLH2 were added to the 5' and 3' sequences respectively. The 5' oligonucleotide primer has the sequence 5' CGGGATCCATGAAACAATTGCCTGCGGC 3' (SEQ ID NO:48) contains a BamHI restriction enzyme site followed by 20 nucleotides of hMLH2 coding sequence starting from the presume terminal amino acid of the processed protein codon. The 3' sequence 5' GCTCTAGACCAGACTCATGCTGTTTT 3' (SEQ ID NO:49) contains complementary sequences to an XbaI site and is followed by 18 nucleotides of hMLH2. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. The amplified sequences and pQE-9 were then digested with BamHI and XbaI. The amplified sequences were ligated into pQE-9 and were inserted in frame with the sequence encoding for the histidine tag and the RBS. The ligation mixture was then used to transform E. coli strain GW3733 by the procedure described in Sambrook, J. et al., Molecular Cloning: A Laboratory Manual, Cold Spring Laboratory Press, (1989). Transformants are identified by their ability to grow on LB plates and ampicillin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. Cells were grown an extra 3 to 4 hours. Cells were then harvested by centrifugation. The cell pellet was solubilized in the chaotropic agent 6 Molar Guanidine HCl. After clarification, solubilized hMLH2 was purified from this solution by chromatography on a Nickel-Chelate column under conditions that allow for tight binding by proteins containing the 6-His tag. (Hochuli, E. et al., J. Chromatography 411:177–184 (1984). hMLH2 was eluted from the column in 6 molar guanidine HCl pH 5.0 and for the purpose of renaturation adjusted to 3 molar guanindine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 6

Bacterial Expression and Purification of hMLH3

The DNA sequence encoding hMLH3, ATCC #75650, is initially amplified using PCR oligonucleotide primers corresponding to the 5' and 3' end sequences of the processed hMLH3 protein. Additional nucleotides corresponding to hMLH3 were added to the 5' and 3' sequences respectively. The 5' oligonucleotide primer has the sequence 5' CGGGATCCATGGAGCGAGCTGAGAGC 3' (SEQ ID NO:50) contains a BamHI restriction enzyme site followed by 18 nucleotides of hMLH3 coding sequence starting from the presumed terminal amino acid of the processed protein codon. The 3' sequence 5' GCTCTAGAGTGAAGACTCTGTCT 3' (SEQ ID NO:51) contains complementary sequences to an XbaI site and is followed by 18 nucleotides of hMLH3. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. The amplified sequences and pQE-9 were then digested with BamHI and XbaI. The amplified sequences were ligated into pQE-9 and were inserted in frame with the sequence encoding for the histidine tag and the RBS. The ligation mixture was then used to transform E. coli strain GW3733 by the procedure described in Sambrook, J. et al, Molecular Cloning: A Laboratory Manual, Cold Spring Laboratory Press, (1989). Transformants are identified by their ability to grow on LB plates and ampicillin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). Tho O/N culture is used to inoculate a large culture at a ratio of 1:100 to 1:250. The cells were grown to an optical density 600 (O.D.$^{600}$) of between 0.4 and 0.6. Cells were grown an extra 3 to 4 hours. Cells were then harvested by centrifugation. The cell pellet was solubilized in the chaotropic agent 6 Molar Guanidine HCl. After clarification, solubilized hMLH3 was purified from this solution by chromatography on a Nickel-Chelate column under conditions that allow for tight binding by proteins containing the 6-His tag Hochuli, E. et al., J. Chromatography 411:177–184 (1984). hMLH3 was eluted from the column in 6 molar guanidine HCl pH 5.0 and for the purpose of renaturation adjusted to 3 molar guanindine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 7

Method for Determination of Mutation of hMLH2 and hMLH3 in Hereditary Cancer

Isolation of Genomic Clones

A human genomic P1 library (Genomic Systems, Inc.) was screened by PCR using primers selected for the cDNA sequence of hMLH2 and hMLH3. Two clones were isolated for hMLH2 using primers 5'-AAGCTGCTCTGTTAAAAGCG-3' (SEQ ID NO:52)

and 5'-GCACCAGCATCCAAGGAG-3' (SEQ ID NO:53) and resulting in a 133 bp product. Three clones were isolated for hMLH3, using primers 5'-CAACCATGAGACACATCGC-3' (SEQ ID NO:54) and 5'AGGTTAGTGAAGACTCTGTC-3' (SEQ ID NO:55) resulting in a 121 bp product. Genomic clones were nick-translated with digoxigenindeoxy-uridine 5'-triphosphate (Boehringer Manheim), and FISH was performed as described (Johnson, Cg. et al., Methods Cell Biol., 35:73–99 (1991)). Hybridization with the hMLH3 probe were carried out using a vast excess of human cot-1 DNA for specific hybridization to the expressed hMLH3 locus. Chromosomes were counterstained with 4,6-diamino-2-phenylidole and propidium iodide, producing a combination of C- and R-bands. Aligned images for precise mapping were obtained using a triple-band filter set (Chroma Technology, Brattleboro, Vt.) in combination with a cooled charge-coupled device camera (Photometrics, Tucson, Ariz.) and variable excitation wavelength filters (Johnson, Cv. et al., Genet. Anal. Tech. Appl., 8:75 (1991)). Image collection, analysis and chromosomal fractional length measurements were done using the ISee Graphical Program System (Inovision Corporation, Durham, N.C.).

Transcription Coupled Translation Mutation Analysis

For purposes of IVSP analysis the hMLH2 gene was divided into three overlapping segments. The first segment included codons 1 to 500, while the middle segment included codons 270 to 755, and the last segment included codons 485 to the translational termination site at codon 933. The primers for the first segment were 5'-GGATCCTAATACGACTCACTATAGGGAGACCAC-CATGGAACAATTGCCTGCGG-3' (SEQ ID NO:56) and 5'CCTGCTCCACTCATCTGC-3' (SEQ ID NO:57), for the middle segment were 5'-GGATCCTAATACGACTCACT-ATAGGGAGACCACCATGGAAGATATCTTAAAGTTA-ATCCG-3' (SEQ ID NO:58) and 5'-GGCTTCTTCTACTCTATATGG-3' (SEQ ID NO:59), and for the final segment were 5'-GGATCCTAATACGACTCACTATAGGGAGACCAC-CATGGCAGGTCTTGAAAACTCTTCG3' (SEQ ID NO:60) and 5'AAAACAAGTCAGTGAATCCTC-3' (SEQ ID NO:61). The primers used for mapping the stop mutation in patient CW all used the same 5' primer as the first segment. The 3' nested primers were: 5'-AAGCACATCTGTTTCTGCTG3' (SEQ ID NO:62) codons 1 to 369; 5'-ACGAGTAGATTCCTTTAGGC-3' (SEQ ID NO:63) codons 1 to 290; and 5'-CAGAACTGACATGAGAGCC-3' (SEQ ID NO:64) codons 1 to 214.

For analysis of hMLH3, the hMLH3 cDNA was amplified as a full-length product or as two overlapping segments. The primers for full-length hMLH3 were 5'-GGATCCTAATACGACTCACTATAGGGAGA CCACCATGGAGCGAGCTGAGAGC-3' (SEQ ID NO:65) and 5'AGGTTAGTGAAGACTCTGTC-3' (SEQ ID NO:66) (codons 1 to 863). For segment 1, the sense primer was the same as above and the antisense primer was 5'-CTGAGGTCTCAGCAGGC-3' (SEQ ID NO:67) (codons 1 to 472). Segment 2 primers were 5'-GGATCCTAATACGACTCACTATAGGGAGACCAC-CATGGTGTCCATTCCAGACTGCG-3' (SEQ ID NO:68) and 5'-AGGTTAGTGAAGACTCTGTC-3' (SEO ID NO:69) (codons 415 to 863). Amplifications were done as described below.

The PCR products contained recognition signals for transcription by T7 RNA polymerase and for the initiation of translation at the 5' ends. PCR products were used as templates in coupled transcription-translation reactions containing 40 uCi of $^{35}$S-methionine (NEN, Dupont). Samples were diluted in SDS sample buffer, and analyzed by electrophoresis on SDS-polyacrylamide gels containing a gradient of 10 to 20% acrylamide. The gels were fixed, treated with EnHance (Dupont), dried and subjected to autoradiography.

RT-PCR and Direct Sequencing of PCR Products cDNAs were generated from RNA of lymphoblastoid or tumor cells with Superscript II (Life Technologies). The cDNAs were then used as templates for PCR. The conditions for all amplifications were 35 cycles at 95° C. for 30 s, 52° C. to 62° C. for 60 to 120 s, and 70° C. for 60 to 120 s, in buffer. The PCR products were directly sequenced and cloned into the T-tailed cloning vector PCR2000 (Invitrogen) and sequenced with T7 polymerase (United States Biochemical). For the direct sequencing of PCR products, PCR reactions were first phenolchloroform extracted and ethanol precipitated. Templates were directly sequenced using Sequitherm polymerase (Epicentre Technologies) and gamma-$^{32}$P labelled primers as described by the manufacturer.

Intron/Exon Boundaries and Genomic Analysis of Mutations

Intron/exon borders were determined by cycle-sequencing P1 clones using gamma-$^{32}$P end labelled primers and SequiTherm polymerase as described by the manufacturer. The primers used to amplify the hMLH2 exon containing codons 195 to 233 were 5'-TTATTTGGCAGAAAAGCAGAG-3' (SEQ ID NO:70) and 5'-TTAAAAGACTAACCTCTTGCC-3' (SEQ ID NO:71), which produced a 215 bp product. The product was cycle sequenced using the primer 5'-CTGCTGTTATGAACAATATGG-3' (SEQ ID NO:72). The primers used to analyze the genomic deletion of hMLH3 in patient GC were: for the 5' region amplification 5'-CAGAAGCAGTTGCAAAGCC-3' (SEQ ID NO:73) and 5'-AAACCGTACTCTTCACACAC-3' (SEQ ID NO:74) which produces a 74 bp product containing codons 233 to 257, primers 5'-GAGGAAAAGCTTTTGTTGGC-3' (SEQ ID NO:75) and 5'-CAGTGGCTGCTGACTGAC-3' (SEQ ID NO:76) which produce a 93 bp product containing the codons 347 to 377, and primers 5'-TCCAGAACCAAGAAGGAGC-3' (SEQ ID NO:77) and 5'-TGAGGTCTCAGCAGGC-3' (SEQ ID NO:78) which produce a 99 bp product containing the codons 439 to 472 of hMLH3.

TABLE 5

Summary of Mutations in HMLH2 and HMLH3 from patients affected with HNPCC

| Sample | Codon | Nucleotides | cDNA Change | Genomic Change | Predicted Coding Change |
|---|---|---|---|---|---|
| HMLH2 | | | | | |
| CW | 233 | | Skipped Exon | CAG to TAG | GLN to Stop Codon |
| HMLH3 | | | | | |
| MM, NS, TF | 20 | | CGG to CAG | CGG to CAG | ARG to GLN |
| GC | 268 to 669 | | 1,203 bp Deletion | Deletion | In-frame deletion |
| GCx | 268 to 669 | | 1,203 bp Deletion | Deletion | Frameshift, truncation |

Numerous modifications and variations of the present invention are possible in light of the above teachings and, therefore, within the scope of the appended claims, the invention may be practiced otherwise than as particularly described.

What is claimed is:

1. An isolated nucleic acid molecule comprising a polynucleotide sequence selected from the group consisting of:
   (a) a polynucleotide sequence encoding amino acids +1 to +932 of SEQ ID NO:4;
   (b) a polynucleotide sequence encoding a fragment of the polypeptide sequence set forth SEQ ID NO:4 wherein said fragment has DNA mismatch repair activity; and
   (c) a polynucleotide sequence complementary to the full length of the polynucleotide sequence of (a) or (b).

2. The isolated nucleic acid molecule of claim 1, wherein said polynucleotide sequence is (a).

3. The isolated nucleic acid molecule of claim 2, comprising polynucleotides +81 to +2876 of SEQ ID NO:3.

4. The isolated nucleic acid molecule of claim 2 wherein said isolated nucleic acid molecule also comprises a heterologous polynucleotide sequence.

5. The isolated nucleic acid molecule of claim 4, wherein the heterologous polynucleotide sequence encodes a heterologous polypeptide.

6. A vector comprising the isolated nucleic acid molecule of claim 2.

7. A host cell comprising the nucleic acid molecule of claim 2 operably associated with a heterologous regulatory sequence.

8. A method of producing a polypeptide comprising:
(a) culturing the host cell of claim 7 under conditions such that the polypeptide is expressed; and
(b) recovering said polypeptide.

9. A composition comprising the isolated nucleic acid molecule of claim 2 and a carrier.

10. The isolated nucleic acid molecule of claim 1, wherein said nucleic acid sequence is (b).

11. The isolated nucleic acid molecule of claim 10 wherein said isolated nucleic acid molecule also comprises a heterologous polynucleotide sequence.

12. The isolated nucleic acid molecule of claim 11, wherein the heterologous polynucleotide sequence encodes a heterologous polypeptide.

13. A vector comprising the isolated nucleic acid molecule of claim 10.

14. A host cell comprising the isolated nucleic acid molecule of claim 10 operably associated with a heterologous regulatory sequence.

15. A method of producing a polypeptide comprising:
(a) culturing the host cell of claim 14 under conditions such that the polypeptide is expressed; and
(b) recovering said polypeptide.

16. A composition comprising the isolated nucleic acid molecule of claim 10 and a carrier.

17. An isolated nucleic acid molecule comprising a polynucleotide sequence selected from the group consisting of:
(a) a polynucleotide sequence encoding the full-length polypeptide encoded by the cDNA contained in ATCC Deposit No. 75651;
(b) a polynucleotide sequence encoding a fragment of the polypeptide encoded by the cDNA contained in ATCC Deposit No. 75651 wherein the fragment has DNA mismatch repair activity; and,
(c) a polynucleotide sequence complementary to the full length of the polynucleotide sequence of (a) or (b).

18. The isolated nucleic acid molecule of claim 17, wherein said nucleic acid sequence is (a).

19. The isolated nucleic acid molecule of claim 18, comprising the open-reading frame of the cDNA contained in ATCC Deposit No. 75651.

20. The isolated nucleic acid molecule of claim 18 wherein said isolated nucleic acid molecule also comprises a heterologous polynucleotide sequence.

21. The isolated nucleic acid molecule of claim 20, wherein the heterologous polynucleotide sequence encodes a heterologous polypeptide.

22. A vector comprising the isolated nucleic acid molecule of claim 18.

23. A host cell comprising the isolated nucleic acid molecule of claim 18 operably associated with a heterologous regulatory sequence.

24. A method of producing a polypeptide comprising:
(a) culturing the host cell of claim 23 under conditions such that the polypeptide is expressed; and
(b) recovering said polypeptide.

25. A composition comprising the isolated nucleic acid molecule of claim 18 and a carrier.

26. The isolated nucleic acid molecule of claim 17, wherein said nucleic acid sequence is (b).

27. The isolated nucleic acid molecule of claim 26 wherein said isolated nucleic acid molecule also comprises a heterologous polynucleotide sequence.

28. The isolated nucleic acid molecule of claim 27, wherein the heterologous polynucleotide sequence encodes a heterologous polypeptide.

29. A vector comprising the isolated nucleic acid molecule of claim 26.

30. A host cell comprising the isolated nucleic acid molecule of claim 26 operably associated with a heterologous regulatory sequence.

31. A method of producing a polypeptide comprising:
(a) culturing the host cell of claim 30 under conditions such that the polypeptide is expressed; and
(b) recovering said polypeptide.

32. A composition comprising the isolated nucleic acid molecule of claim 26 and a carrier.

33. An isolated nucleic acid molecule comprising a first polynucleotide sequence that is at least 95% identical to a second polynucleotide sequence selected from the group consisting of:
(a) a polynucleotide sequence encoding amino acids +1 to +932 of SEQ ID NO:4;
(b) a polynucleotide sequence encoding a fragment of the polypeptide sequence set forth in SEQ ID NO:4 wherein said fragment has DNA mismatch repair activity; and
(c) a polynucleotide sequence complementary to the full length of the polynucleotide sequence of (a) or (b).

34. The isolated nucleic acid molecule of claim 33, wherein said second polynucleotide sequence is (a).

35. The isolated nucleic acid molecule of claim 34 wherein said isolated nucleic acid molecule also comprises a heterologous polynucleotide sequence.

36. The isolated nucleic acid molecule of claim 35, wherein the heterologous polynucleotide sequence encodes a heterologous polypeptide.

37. A vector comprising the isolated nucleic acid molecule of claim 34.

38. A host cell comprising the isolated nucleic acid molecule of claim 34 operably associated with a heterologous regulatory sequence.

39. A method of producing a polypeptide comprising:
(a) culturing the host cell of claim 38 under conditions such that the polypeptide is expressed; and
(b) recovering said polypeptide.

40. A composition comprising the isolated nucleic acid molecule of claim 34 and a carrier.

41. The isolated nucleic acid molecule of claim 33, wherein said second polynucleotide sequence is (b).

42. The isolated nucleic acid molecule of claim 41 further comprising a heterologous polynucleotide.

43. The isolated nucleic acid molecule of claim 42, wherein the heterologous polynucleotide encodes a heterologous polypeptide.

44. A vector comprising the isolated nucleic acid molecule of claim 41.

45. A host cell comprising the isolated nucleic acid molecule of claim 41 operably associated with a heterologous regulatory sequence.

46. A method of producing a polypeptide comprising:
(a) culturing the host cell of claim 45 under conditions such that the polypeptide is expressed; and
(b) recovering said polypeptide.

47. A composition comprising the isolated nucleic acid molecule of claim 41 and a carrier.

48. An isolated nucleic acid molecule comprising a first polynucleotide sequence that is at least 95% identical to a second polynucleotide sequence selected from the group consisting of:
(a) a polynucleotide sequence encoding the full-length polypeptide encoded by the cDNA contained in ATCC Deposit No. 75651;
(b) a polynucleotide sequence encoding a fragment of the polypeptide encoded by the cDNA contained in ATCC Deposit No. 75651 wherein said fragment has DNA mismatch repair activity; and,
(c) a polynucleotide sequence complementary to the full length of the polynucleotide sequence of (a) or (b).

49. The isolated nucleic acid molecule of claim 48, wherein said second polynucleotide sequence is (a).

50. The isolated nucleic acid molecule of claim 49 wherein said isolated nucleic acid molecule also comprises a heterologous polynucleotide sequence.

51. The isolated nucleic acid molecule of claim 50, wherein the heterologous polynucleotide sequence encodes a heterologous polypeptide.

52. A vector comprising the isolated nucleic acid molecule of claim 49.

53. A host cell comprising the isolated nucleic acid molecule of claim 49 operably associated with a heterologous regulatory sequence.

54. A method of producing a polypeptide comprising:
(a) culturing the host cell of claim 53 under conditions such that the polypeptide is expressed; and
(b) recovering said polypeptide.

55. A composition comprising the isolated nucleic acid molecule of claim 49 and a carrier.

56. The isolated nucleic acid molecule of claim 48, wherein said said second polynucleotide sequence is (b).

57. The isolated nucleic acid molecule of claim 56 wherein said isolated nucleic acid molecule also comprises a heterologous polynucleotide sequence.

58. The isolated nucleic acid molecule of claim 57, wherein the heterologous polynucleotide sequence encodes a heterologous polypeptide.

59. A vector comprising the isolated nucleic acid molecule of claim 56.

60. A host cell comprising the isolated nucleic acid molecule of claim 56 operably associated with a heterologous regulatory sequence.

61. A method of producing a polypeptide comprising:
(a) culturing the host cell of claim 60 under conditions such that the polypeptide is expressed; and
(b) recovering said polypeptide.

62. A composition comprising the isolated nucleic acid molecule of claim 56 and a carrier.

* * * * *

SEQUENCE LISTING

<160> NUMBER OF SEQ ID NOS: 78

<210> SEQ ID NO 1
<211> LENGTH: 2525
<212> TYPE: DNA
<213> ORGANISM: homo sapiens
<220> FEATURE:
<221> NAME/KEY: CDS
<222> LOCATION: (42)..(2312)

<400> SEQUENCE: 1

```
gttgaacatc tagacgtttc cttggctctt ctggcgccaa a atg tcg ttc gtg gca      56
                                              Met Ser Phe Val Ala
                                                1               5 ggg gtt att cgg cgg ctg gac gag aca gtg g tg aac cgc atc gcg gcg      104
Gly Val Ile Arg Arg Leu Asp Glu Thr Val V al Asn Arg Ile Ala Ala
             10                  15                     20 ggg gaa gtt atc cag cgg cca gct aat gct a tc aaa gag atg att gag      152
Gly Glu Val Ile Gln Arg Pro Ala Asn Ala I le Lys Glu Met Ile Glu
         25                  30                 35 aac tgt tta gat gca aaa tcc aca agt att c aa gtg att gtt aaa gag      200
Asn Cys Leu Asp Ala Lys Ser Thr Ser Ile G ln Val Ile Val Lys Glu
        40                  45                  50 gga ggc ctg aag ttg att cag atc caa gac a at ggc acc ggg atc agg      248
Gly Gly Leu Lys Leu Ile Gln Ile Gln Asp A sn Gly Thr Gly Ile Arg
 55                  60                  65 aaa gaa gat ctg gat att gta tgt gaa agg t tc act act agt aaa ctg      296
Lys Glu Asp Leu Asp Ile Val Cys Glu Arg P he Thr Thr Ser Lys Leu
70                  75                  80                  85 cag tcc ttt gag gat tta gcc agt att tct a cc tat ggc ttt cga ggt      344
Gln Ser Phe Glu Asp Leu Ala Ser Ile Ser T hr Tyr Gly Phe Arg Gly
                 90                  95                 100 gag gct ttg gcc agc ata agc cat gtg gct c at gtt act att aca acg      392
Glu Ala Leu Ala Ser Ile Ser His Val Ala H is Val Thr Ile Thr Thr
            105                 110                 115 aaa aca gct gat gga aag tgt gca tac aga g ca agt tac tca gat gga      440
Lys Thr Ala Asp Gly Lys Cys Ala Tyr Arg A la Ser Tyr Ser Asp Gly
        120                 125                 130 aaa ctg aaa gcc cct cct aaa cca tgt gct g gc aat caa ggg acc cag      488
Lys Leu Lys Ala Pro Pro Lys Pro Cys Ala G ly Asn Gln Gly Thr Gln
135                 140                 145 atc acg gtg gag gac ctt ttt tac aac ata g cc acg agg aga aaa gct      536
Ile Thr Val Glu Asp Leu Phe Tyr Asn Ile A la Thr Arg Arg Lys Ala
150                 155                 160                 165 tta aaa aat cca agt gaa gaa tat ggg aaa a tt ttg gaa gtt gtt ggc      584
Leu Lys Asn Pro Ser Glu Glu Tyr Gly Lys I le Leu Glu Val Val Gly
                170                 175                 180 agg tat tca gta cac aat gca ggc att agt t tc tca gtt aaa aaa caa      632
Arg Tyr Ser Val His Asn Ala Gly Ile Ser P he Ser Val Lys Lys Gln
            185                 190                 195 gga gag aca gta gct gat gtt agg aca cta c cc aat gcc tca acc gtg      680
Gly Glu Thr Val Ala Asp Val Arg Thr Leu P ro Asn Ala Ser Thr Val
        200                 205                 210 gac aat att cgc tcc gtc ttt gga aat gct g tt agt cga gaa ctg ata      728
Asp Asn Ile Arg Ser Val Phe Gly Asn Ala V al Ser Arg Glu Leu Ile
    215                 220                 225 gaa att gga tgt gag gat aaa acc cta gcc t tc aaa atg aat ggt tac      776
Glu Ile Gly Cys Glu Asp Lys Thr Leu Ala P he Lys Met Asn Gly Tyr
230                 235                 240                 245
```

| | |
|---|---|
| ata tcc aat gca aac tac tca gtg aag aag t gc atc ttc tta ctc ttc<br>Ile Ser Asn Ala Asn Tyr Ser Val Lys Lys C ys Ile Phe Leu Leu Phe<br>250 255 260 | 824 |
| atc aac cat cgt ctg gta gaa tca act tcc t tg aga aaa gcc ata gaa<br>Ile Asn His Arg Leu Val Glu Ser Thr Ser L eu Arg Lys Ala Ile Glu<br>265 270 275 | 872 |
| aca gtg tat gca gcc tat ttg ccc aaa aac a ca cac cca ttc ctg tac<br>Thr Val Tyr Ala Ala Tyr Leu Pro Lys Asn T hr His Pro Phe Leu Tyr<br>280 285 290 | 920 |
| ctc agt tta gaa atc agt ccc cag aat gtg g at gtt aat gtg cac ccc<br>Leu Ser Leu Glu Ile Ser Pro Gln Asn Val A sp Val Asn Val His Pro<br>295 300 305 | 968 |
| aca aag cat gaa gtt cac ttc ctg cac gag g ag agc atc ctg gag cgg<br>Thr Lys His Glu Val His Phe Leu His Glu G lu Ser Ile Leu Glu Arg<br>310 315 320 325 | 1016 |
| gtg cag cag cac atc gag agc aag ctc ctg g gc tcc aat tcc tcc agg<br>Val Gln Gln His Ile Glu Ser Lys Leu Leu G ly Ser Asn Ser Ser Arg<br>330 335 340 | 1064 |
| atg tac ttc acc cag act ttg cta cca gga c tt gct ggc ccc tct ggg<br>Met Tyr Phe Thr Gln Thr Leu Leu Pro Gly L eu Ala Gly Pro Ser Gly<br>345 350 355 | 1112 |
| gag atg gtt aaa tcc aca aca agt ctg acc t cg tct tct act tct gga<br>Glu Met Val Lys Ser Thr Thr Ser Leu Thr S er Ser Ser Thr Ser Gly<br>360 365 370 | 1160 |
| agt agt gat aag gtc tat gcc cac cag atg g tt cgt aca gat tcc cgg<br>Ser Ser Asp Lys Val Tyr Ala His Gln Met V al Arg Thr Asp Ser Arg<br>375 380 385 | 1208 |
| gaa cag aag ctt gat gca ttt ctg cag cct c tg agc aaa ccc ctg tcc<br>Glu Gln Lys Leu Asp Ala Phe Leu Gln Pro L eu Ser Lys Pro Leu Ser<br>390 395 400 405 | 1256 |
| agt cag ccc cag gcc att gtc aca gag gat a ag aca gat att tct agt<br>Ser Gln Pro Gln Ala Ile Val Thr Glu Asp L ys Thr Asp Ile Ser Ser<br>410 415 420 | 1304 |
| ggc agg gct agg cag caa gat gag gag atg c tt gaa ctc cca gcc cct<br>Gly Arg Ala Arg Gln Gln Asp Glu Glu Met L eu Glu Leu Pro Ala Pro<br>425 430 435 | 1352 |
| gct gaa gtg gct gcc aaa aat cag agc ttg g ag ggg gat aca aca aag<br>Ala Glu Val Ala Ala Lys Asn Gln Ser Leu G lu Gly Asp Thr Thr Lys<br>440 445 450 | 1400 |
| ggg act tca gaa atg tca gag aag aga gga c ct act tcc agc aac ccc<br>Gly Thr Ser Glu Met Ser Glu Lys Arg Gly P ro Thr Ser Ser Asn Pro<br>455 460 465 | 1448 |
| aga aag aga cat cgg gaa gat tct gat gtg g aa atg gtg gaa gat gat<br>Arg Lys Arg His Arg Glu Asp Ser Asp Val G lu Met Val Glu Asp Asp<br>470 475 480 485 | 1496 |
| tcc cga aag gaa atg act gca gct tgt acc c cc cgg aga agg atc att<br>Ser Arg Lys Glu Met Thr Ala Ala Cys Thr P ro Arg Arg Arg Ile Ile<br>490 495 500 | 1544 |
| aac ctc act agt gtt ttg agt ctc cag gaa g aa att aat gag cag gga<br>Asn Leu Thr Ser Val Leu Ser Leu Gln Glu G lu Ile Asn Glu Gln Gly<br>505 510 515 | 1592 |
| cat gag gtt ctc cgg gag atg ttg cat aac c ac tcc ttc gtg ggc tgt<br>His Glu Val Leu Arg Glu Met Leu His Asn H is Ser Phe Val Gly Cys<br>520 525 530 | 1640 |
| gtg aat cct cag tgg gcc ttg gca cag cat c aa acc aag tta tac ctt<br>Val Asn Pro Gln Trp Ala Leu Ala Gln His G ln Thr Lys Leu Tyr Leu<br>535 540 545 | 1688 |
| ctc aac acc acc aag ctt agt gaa gaa ctg t tc tac cag ata ctc att<br>Leu Asn Thr Thr Lys Leu Ser Glu Glu Leu P he Tyr Gln Ile Leu Ile<br>550 555 560 565 | 1736 |

-continued

| | |
|---|---|
| tat gat ttt gcc aat ttt ggt gtt ctc agg t ta tcg gag cca gca ccg<br>Tyr Asp Phe Ala Asn Phe Gly Val Leu Arg L eu Ser Glu Pro Ala Pro<br>570                575                580 | 1784 |
| ctc ttt gac ctt gcc atg ctt gcc tta gat a gt cca gag agt ggc tgg<br>Leu Phe Asp Leu Ala Met Leu Ala Leu Asp S er Pro Glu Ser Gly Trp<br>585                590                595 | 1832 |
| aca gag gaa gat ggt ccc aaa gaa gga ctt g ct gaa tac att gtt gag<br>Thr Glu Glu Asp Gly Pro Lys Glu Gly Leu A la Glu Tyr Ile Val Glu<br>600                605                610 | 1880 |
| ttt ctg aag aag aag gct gag atg ctt gca g ac tat ttc tct ttg gaa<br>Phe Leu Lys Lys Lys Ala Glu Met Leu Ala A sp Tyr Phe Ser Leu Glu<br>615                620                625 | 1928 |
| att gat gag gaa ggg aac ctg att gga tta c cc ctt ctg att gac aac<br>Ile Asp Glu Glu Gly Asn Leu Ile Gly Leu P ro Leu Leu Ile Asp Asn<br>630                635                640                645 | 1976 |
| tat gtg ccc cct ttg gag gga ctg cct atc t tc att ctt cga cta gcc<br>Tyr Val Pro Pro Leu Glu Gly Leu Pro Ile P he Ile Leu Arg Leu Ala<br>650                655                660 | 2024 |
| act gag gtg aat tgg gac gaa gaa aag gaa t gt ttt gaa agc ctc agt<br>Thr Glu Val Asn Trp Asp Glu Glu Lys Glu C ys Phe Glu Ser Leu Ser<br>665                670                675 | 2072 |
| aaa gaa tgc gct atg ttc tat tcc atc cgg a ag cag tac ata tct gag<br>Lys Glu Cys Ala Met Phe Tyr Ser Ile Arg L ys Gln Tyr Ile Ser Glu<br>680                685                690 | 2120 |
| gag tcg acc ctc tca ggc cag cag agt gaa g tg cct ggc tcc att cca<br>Glu Ser Thr Leu Ser Gly Gln Gln Ser Glu V al Pro Gly Ser Ile Pro<br>695                700                705 | 2168 |
| aac tcc tgg aag tgg act gtg gaa cac att g tc tat aaa gcc ttg cgc<br>Asn Ser Trp Lys Trp Thr Val Glu His Ile V al Tyr Lys Ala Leu Arg<br>710                715                720                725 | 2216 |
| tca cac att ctg cct cct aaa cat ttc aca g aa gat gga aat atc ctg<br>Ser His Ile Leu Pro Pro Lys His Phe Thr G lu Asp Gly Asn Ile Leu<br>730                735                740 | 2264 |
| cag ctt gct aac ctg cct gat cta tac aaa g tc ttt gag agg tgt taa<br>Gln Leu Ala Asn Leu Pro Asp Leu Tyr Lys V al Phe Glu Arg Cys<br>745                750                755 | 2312 |
| atatggttat ttatgcactg tgggatgtgt tcttctttct ctgtattccg a tacaaagtg | 2372 |
| ttgtatcaaa gtgtgatata caaagtgtac aacataagt gttggtagca c ttaagactt | 2432 |
| atacttgcct tctgatagta ttcctttata cacagtggat tgattataaa t aaatagatg | 2492 |
| tgtcttaaca taaaaaaaaa aaaaaaaaaa aaa | 2525 |

<210> SEQ ID NO 2
<211> LENGTH: 756
<212> TYPE: PRT
<213> ORGANISM: homo sapiens

<400> SEQUENCE: 2

Met Ser Phe Val Ala Gly Val Ile Arg Arg L eu Asp Glu Thr Val Val
1                5                10                15

Asn Arg Ile Ala Ala Gly Glu Val Ile Gln A rg Pro Ala Asn Ala Ile
                20                25                30

Lys Glu Met Ile Glu Asn Cys Leu Asp Ala L ys Ser Thr Ser Ile Gln
            35                40                45

Val Ile Val Lys Glu Gly Gly Leu Lys Leu I le Gln Ile Gln Asp Asn
        50                55                60

Gly Thr Gly Ile Arg Lys Glu Asp Leu Asp I le Val Cys Glu Arg Phe
65                70                75                80

```
Thr Thr Ser Lys Leu Gln Ser Phe Glu Asp L eu Ala Ser Ile Ser Thr
                85                  90                  95

Tyr Gly Phe Arg Gly Glu Ala Leu Ala Ser I le Ser His Val Ala His
                100                 105                 110

Val Thr Ile Thr Thr Lys Thr Ala Asp Gly L ys Cys Ala Tyr Arg Ala
                115                 120                 125

Ser Tyr Ser Asp Gly Lys Leu Lys Ala Pro P ro Lys Pro Cys Ala Gly
    130                 135                 140

Asn Gln Gly Thr Gln Ile Thr Val Glu Asp L eu Phe Tyr Asn Ile Ala
145                 150                 155                 160

Thr Arg Arg Lys Ala Leu Lys Asn Pro Ser G lu Glu Tyr Gly Lys Ile
                165                 170                 175

Leu Glu Val Val Gly Arg Tyr Ser Val His A sn Ala Gly Ile Ser Phe
                180                 185                 190

Ser Val Lys Lys Gln Gly Glu Thr Val Ala A sp Val Arg Thr Leu Pro
                195                 200                 205

Asn Ala Ser Thr Val Asp Asn Ile Arg Ser V al Phe Gly Asn Ala Val
                210                 215                 220

Ser Arg Glu Leu Ile Glu Ile Gly Cys Glu A sp Lys Thr Leu Ala Phe
225                 230                 235                 240

Lys Met Asn Gly Tyr Ile Ser Asn Ala Asn T yr Ser Val Lys Lys Cys
                245                 250                 255

Ile Phe Leu Leu Phe Ile Asn His Arg Leu V al Glu Ser Thr Ser Leu
                260                 265                 270

Arg Lys Ala Ile Glu Thr Val Tyr Ala Ala T yr Leu Pro Lys Asn Thr
                275                 280                 285

His Pro Phe Leu Tyr Leu Ser Leu Glu Ile S er Pro Gln Asn Val Asp
    290                 295                 300

Val Asn Val His Pro Thr Lys His Glu Val H is Phe Leu His Glu Glu
305                 310                 315                 320

Ser Ile Leu Glu Arg Val Gln Gln His Ile G lu Ser Lys Leu Leu Gly
                325                 330                 335

Ser Asn Ser Ser Arg Met Tyr Phe Thr Gln T hr Leu Leu Pro Gly Leu
                340                 345                 350

Ala Gly Pro Ser Gly Glu Met Val Lys Ser T hr Thr Ser Leu Thr Ser
                355                 360                 365

Ser Ser Thr Ser Gly Ser Ser Asp Lys Val T yr Ala His Gln Met Val
    370                 375                 380

Arg Thr Asp Ser Arg Glu Gln Lys Leu Asp A la Phe Leu Gln Pro Leu
385                 390                 395                 400

Ser Lys Pro Leu Ser Ser Gln Pro Gln Ala I le Val Thr Glu Asp Lys
                405                 410                 415

Thr Asp Ile Ser Ser Gly Arg Ala Arg Gln G ln Asp Glu Glu Met Leu
                420                 425                 430

Glu Leu Pro Ala Pro Ala Glu Val Ala Ala L ys Asn Gln Ser Leu Glu
                435                 440                 445

Gly Asp Thr Thr Lys Gly Thr Ser Glu Met S er Glu Lys Arg Gly Pro
    450                 455                 460

Thr Ser Ser Asn Pro Arg Lys Arg His Arg G lu Asp Ser Asp Val Glu
465                 470                 475                 480

Met Val Glu Asp Asp Ser Arg Lys Glu Met T hr Ala Ala Cys Thr Pro
                485                 490                 495
```

-continued

```
Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Asp Gly Pro Lys Glu Gly Leu Ala
        595                 600                 605

Glu Tyr Ile Val Glu Phe Leu Lys Lys Ala Glu Met Leu Ala Asp
    610                 615                 620

Tyr Phe Ser Leu Glu Ile Asp Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 3
<211> LENGTH: 3063
<212> TYPE: DNA
<213> ORGANISM: homo sapiens
<220> FEATURE:
<221> NAME/KEY: CDS
<222> LOCATION: (81)..(2879)

<400> SEQUENCE: 3
ggcacgagtg  gctgcttgcg  gctagtggat  ggtaattgcc  tgcctcgcgc  t agcagcaag        60 ctgctctgtt  aaaagcgaaa  atg aaa caa ttg cct gcg g ca aca gtt cga ctc       113
                        Met Lys Gln Leu Pro Ala Ala Thr Val Arg Leu
                          1               5                  10 ctt tca agt tct cag atc atc act tcg gtg g tc agt gtt gta aaa gag         161
Leu Ser Ser Ser Gln Ile Ile Thr Ser Val Val Ser Val Val Lys Glu
            15                  20                  25 ctt att gaa aac tcc ttg gat gct ggt gcc a ca agc gta gat gtt aaa         209
Leu Ile Glu Asn Ser Leu Asp Ala Gly Ala Thr Ser Val Asp Val Lys
        30                  35                  40 ctg gag aac tat gga ttt gat aaa att gag g tg cga gat aac ggg gag         257
Leu Glu Asn Tyr Gly Phe Asp Lys Ile Glu Val Arg Asp Asn Gly Glu
    45                  50                  55
```

```
ggt atc aag gct gtt gat gca cct gta atg g ca atg aag tac tac acc    305
Gly Ile Lys Ala Val Asp Ala Pro Val Met A la Met Lys Tyr Tyr Thr
 60              65                  70                  75 tca aaa ata aat agt cat gaa gat ctt gaa a at ttg aca act tac ggt    353
Ser Lys Ile Asn Ser His Glu Asp Leu Glu A sn Leu Thr Thr Tyr Gly
             80                  85                  90 ttt cgt gga gaa gcc ttg ggg tca att tgt t gt ata gct gag gtt tta    401
Phe Arg Gly Glu Ala Leu Gly Ser Ile Cys C ys Ile Ala Glu Val Leu
         95                 100                 105 att aca aca aga acg gct gct gat aat ttt a gc acc cag tat gtt tta    449
Ile Thr Thr Arg Thr Ala Ala Asp Asn Phe S er Thr Gln Tyr Val Leu
        110                 115                 120 gat ggc agt ggc cac ata ctt tct cag aaa c ct tca cat ctt ggt caa    497
Asp Gly Ser Gly His Ile Leu Ser Gln Lys P ro Ser His Leu Gly Gln
    125                 130                 135 ggt aca act gta act gct tta aga tta ttt a ag aat cta cct gta aga    545
Gly Thr Thr Val Thr Ala Leu Arg Leu Phe L ys Asn Leu Pro Val Arg
140                 145                 150                 155 aag cag ttt tac tca act gca aaa aaa tgt a aa gat gaa ata aaa aag    593
Lys Gln Phe Tyr Ser Thr Ala Lys Lys Cys L ys Asp Glu Ile Lys Lys
                160                 165                 170 atc caa gat ctc ctc atg agc ttt ggt atc c tt aaa cct gac tta agg    641
Ile Gln Asp Leu Leu Met Ser Phe Gly Ile L eu Lys Pro Asp Leu Arg
            175                 180                 185 att gtc ttt gta cat aac aag gca gtt att t gg cag aaa agc aga gta    689
Ile Val Phe Val His Asn Lys Ala Val Ile T rp Gln Lys Ser Arg Val
        190                 195                 200 tca gat cac aag atg gct ctc atg tca gtt c tg ggg act gct gtt atg    737
Ser Asp His Lys Met Ala Leu Met Ser Val L eu Gly Thr Ala Val Met
    205                 210                 215 aac aat atg gaa tcc ttt cag tac cac tct g aa gaa tct cag att tat    785
Asn Asn Met Glu Ser Phe Gln Tyr His Ser G lu Glu Ser Gln Ile Tyr
220                 225                 230                 235 ctc agt gga ttt ctt cca aag tgt gat gca g ac cac tct ttc act agt    833
Leu Ser Gly Phe Leu Pro Lys Cys Asp Ala A sp His Ser Phe Thr Ser
                240                 245                 250 ctt tca aca cca gaa aga agt ttc atc ttc a ta aac agt cga cca gta    881
Leu Ser Thr Pro Glu Arg Ser Phe Ile Phe I le Asn Ser Arg Pro Val
            255                 260                 265 cat caa aaa gat atc tta aag tta atc cga c at cat tac aat ctg aaa    929
His Gln Lys Asp Ile Leu Lys Leu Ile Arg H is His Tyr Asn Leu Lys
        270                 275                 280 tgc cta aag gaa tct act cgt ttg tat cct g tt ttc ttt ctg aaa atc    977
Cys Leu Lys Glu Ser Thr Arg Leu Tyr Pro V al Phe Phe Leu Lys Ile
    285                 290                 295 gat gtt cct aca gct gat gtt gat gta aat t ta aca cca gat aaa agc    1025
Asp Val Pro Thr Ala Asp Val Asp Val Asn L eu Thr Pro Asp Lys Ser
300                 305                 310                 315 caa gta tta tta caa aat aag gaa tct gtt t ta att gct ctt gaa aat    1073
Gln Val Leu Leu Gln Asn Lys Glu Ser Val L eu Ile Ala Leu Glu Asn
                320                 325                 330 ctg atg acg act tgt tat gga cca tta cct a gt aca aat tct tat gaa    1121
Leu Met Thr Thr Cys Tyr Gly Pro Leu Pro S er Thr Asn Ser Tyr Glu
            335                 340                 345 aat aat aaa aca gat gtt tcc gca gct gac a tc gtt ctt agt aaa aca    1169
Asn Asn Lys Thr Asp Val Ser Ala Ala Asp I le Val Leu Ser Lys Thr
        350                 355                 360 gca gaa aca gat gtg ctt ttt aat aaa gtg g aa tca tct gga aag aat    1217
Ala Glu Thr Asp Val Leu Phe Asn Lys Val G lu Ser Ser Gly Lys Asn
    365                 370                 375
```

-continued

| | |
|---|---|
| tat tca aat gtt gat act tca gtc att cca t tc caa aat gat atg cat<br>Tyr Ser Asn Val Asp Thr Ser Val Ile Pro P he Gln Asn Asp Met His<br>380    385    390    395 | 1265 |
| aat gat gaa tct gga aaa aac act gat gat t gt tta aat cac cag ata<br>Asn Asp Glu Ser Gly Lys Asn Thr Asp Asp C ys Leu Asn His Gln Ile<br>    400    405    410 | 1313 |
| agt att ggt gac ttt ggt tat ggt cat tgt a gt agt gaa att tct aac<br>Ser Ile Gly Asp Phe Gly Tyr Gly His Cys S er Ser Glu Ile Ser Asn<br>415    420    425 | 1361 |
| att gat aaa aac act aag aat gca ttt cag g ac att tca atg agt aat<br>Ile Asp Lys Asn Thr Lys Asn Ala Phe Gln A sp Ile Ser Met Ser Asn<br>430    435    440 | 1409 |
| gta tca tgg gag aac tct cag acg gaa tat a gt aaa act tgt ttt ata<br>Val Ser Trp Glu Asn Ser Gln Thr Glu Tyr S er Lys Thr Cys Phe Ile<br>445    450    455 | 1457 |
| agt tcc gtt aag cac acc cag tca gaa aat g gc aat aaa gac cat ata<br>Ser Ser Val Lys His Thr Gln Ser Glu Asn G ly Asn Lys Asp His Ile<br>460    465    470    475 | 1505 |
| gat gag agt ggg gaa aat gag gaa gaa gca g gt ctt gaa aac tct tcg<br>Asp Glu Ser Gly Glu Asn Glu Glu Glu Ala G ly Leu Glu Asn Ser Ser<br>    480    485    490 | 1553 |
| gaa att tct gca gat gag tgg agc agg gga a at ata ctt aaa aat tca<br>Glu Ile Ser Ala Asp Glu Trp Ser Arg Gly A sn Ile Leu Lys Asn Ser<br>495    500    505 | 1601 |
| gtg gga gag aat att gaa cct gtg aaa att t ta gtg cct gaa aaa agt<br>Val Gly Glu Asn Ile Glu Pro Val Lys Ile L eu Val Pro Glu Lys Ser<br>510    515    520 | 1649 |
| tta cca tgt aaa gta agt aat aat aat tat c ca atc cct gaa caa atg<br>Leu Pro Cys Lys Val Ser Asn Asn Asn Tyr P ro Ile Pro Glu Gln Met<br>525    530    535 | 1697 |
| aat ctt aat gaa gat tca tgt aac aaa aaa t ca aat gta ata gat aat<br>Asn Leu Asn Glu Asp Ser Cys Asn Lys Lys S er Asn Val Ile Asp Asn<br>540    545    550    555 | 1745 |
| aaa tct gga aaa gtt aca gct tat gat tta c tt agc aat cga gta atc<br>Lys Ser Gly Lys Val Thr Ala Tyr Asp Leu L eu Ser Asn Arg Val Ile<br>    560    565    570 | 1793 |
| aag aaa ccc atg tca gca agt gct ctt ttt g tt caa gat cat cgt cct<br>Lys Lys Pro Met Ser Ala Ser Ala Leu Phe V al Gln Asp His Arg Pro<br>575    580    585 | 1841 |
| cag ttt ctc ata gaa aat cct aag act agt t ta gag gat gca aca cta<br>Gln Phe Leu Ile Glu Asn Pro Lys Thr Ser L eu Glu Asp Ala Thr Leu<br>590    595    600 | 1889 |
| caa att gaa gaa ctg tgg aag aca ttg agt g aa gag gaa aaa ctg aaa<br>Gln Ile Glu Glu Leu Trp Lys Thr Leu Ser G lu Glu Glu Lys Leu Lys<br>605    610    615 | 1937 |
| tat gaa gag aag gct act aaa gac ttg gaa c ga tac aat agt caa atg<br>Tyr Glu Glu Lys Ala Thr Lys Asp Leu Glu A rg Tyr Asn Ser Gln Met<br>620    625    630    635 | 1985 |
| aag aga gcc att gaa cag gag tca caa atg t ca cta aaa gat ggc aga<br>Lys Arg Ala Ile Glu Gln Glu Ser Gln Met S er Leu Lys Asp Gly Arg<br>640    645    650 | 2033 |
| aaa aag ata aaa ccc acc agc gca tgg aat t tg gcc cag aag cac aag<br>Lys Lys Ile Lys Pro Thr Ser Ala Trp Asn L eu Ala Gln Lys His Lys<br>655    660    665 | 2081 |
| tta aaa acc tca tta tct aat caa cca aaa c tt gat gaa ctc ctt cag<br>Leu Lys Thr Ser Leu Ser Asn Gln Pro Lys L eu Asp Glu Leu Leu Gln<br>670    675    680 | 2129 |
| tcc caa att gaa aaa aga agg agt caa aat a tt aaa atg gta cag atc<br>Ser Gln Ile Glu Lys Arg Arg Ser Gln Asn I le Lys Met Val Gln Ile<br>685    690    695 | 2177 |

```
ccc ttt tct atg aaa aac tta aaa ata aat t tt aag aaa caa aac aaa      2225
Pro Phe Ser Met Lys Asn Leu Lys Ile Asn P he Lys Lys Gln Asn Lys
700             705                 710                 715 gtt gac tta gaa gag aag gat gaa cct tgc t tg atc cac aat ctc agg      2273
Val Asp Leu Glu Glu Lys Asp Glu Pro Cys L eu Ile His Asn Leu Arg
            720                 725                 730 ttt cct gat gca tgg cta atg aca tcc aaa a ca gag gta atg tta tta     2321
Phe Pro Asp Ala Trp Leu Met Thr Ser Lys T hr Glu Val Met Leu Leu
        735                 740                 745 aat cca tat aga gta gaa gaa gcc ctg cta t tt aaa aga ctt ctt gag     2369
Asn Pro Tyr Arg Val Glu Glu Ala Leu Leu P he Lys Arg Leu Leu Glu
    750                 755                 760 aat cat aaa ctt cct gca gag cca ctg gaa a ag cca att atg tta aca     2417
Asn His Lys Leu Pro Ala Glu Pro Leu Glu L ys Pro Ile Met Leu Thr
765                 770                 775 gag agt ctt ttt aat gga tct cat tat tta g ac gtt tta tat aaa atg     2465
Glu Ser Leu Phe Asn Gly Ser His Tyr Leu A sp Val Leu Tyr Lys Met
780                 785                 790                 795 aca gca gat gac caa aga tac agt gga tca a ct tac ctg tct gat cct    2513
Thr Ala Asp Asp Gln Arg Tyr Ser Gly Ser T hr Tyr Leu Ser Asp Pro
                800                 805                 810 cgt ctt aca gcg aat ggt ttc aag ata aaa t tg ata cca gga gtt tca    2561
Arg Leu Thr Ala Asn Gly Phe Lys Ile Lys L eu Ile Pro Gly Val Ser
            815                 820                 825 att act gaa aat tac ttg gaa ata gaa gga a tg gct aat tgt ctc cca    2609
Ile Thr Glu Asn Tyr Leu Glu Ile Glu Gly M et Ala Asn Cys Leu Pro
        830                 835                 840 ttc tat gga gta gca gat tta aaa gaa att c tt aat gct ata tta aac    2657
Phe Tyr Gly Val Ala Asp Leu Lys Glu Ile L eu Asn Ala Ile Leu Asn
    845                 850                 855 aga aat gca aag gaa gtt tat gaa tgt aga c ct cgc aaa gtg ata agt    2705
Arg Asn Ala Lys Glu Val Tyr Glu Cys Arg P ro Arg Lys Val Ile Ser
860                 865                 870                 875 tat tta gag gga gaa gca gtg cgt cta tcc a ga caa tta ccc atg tac    2753
Tyr Leu Glu Gly Glu Ala Val Arg Leu Ser A rg Gln Leu Pro Met Tyr
                880                 885                 890 tta tca aaa gag gac atc caa gac att atc t ac aga atg aag cac cag    2801
Leu Ser Lys Glu Asp Ile Gln Asp Ile Ile T yr Arg Met Lys His Gln
            895                 900                 905 ttt gga aat gaa att aaa gag tgt gtt cat g gt cgc cca ttt ttt cat    2849
Phe Gly Asn Glu Ile Lys Glu Cys Val His G ly Arg Pro Phe Phe His
        910                 915                 920 cat tta acc tat ctt cca gaa act aca tga t taaatatgt ttaagaagat     2899
His Leu Thr Tyr Leu Pro Glu Thr Thr
    925                 930 tagttaccat tgaaattggt tctgtcataa aacagcatga gtctggtttt a aattatctt  2959 tgtattatgt gtcacatggt tatttttttaa atgaggattc actgacttgt t tttatattg 3019 aaaaaagttc cacgtattgt agaaaacgta aataaactaa taac                    306 3
```

<210> SEQ ID NO 4
<211> LENGTH: 932
<212> TYPE: PRT
<213> ORGANISM: homo sapiens

<400> SEQUENCE: 4

Met Lys Gln Leu Pro Ala Ala Thr Val Arg L eu Leu Ser Ser Ser Gln
1               5                   10                  15

Ile Ile Thr Ser Val Val Ser Val Val Lys G lu Leu Ile Glu Asn Ser
            20                  25                  30

```
Leu Asp Ala Gly Ala Thr Ser Val Asp Val Lys Leu Glu Asn Tyr Gly
     35                  40                  45
Phe Asp Lys Ile Glu Val Arg Asp Asn Gly Glu Gly Ile Lys Ala Val
 50                  55                  60
Asp Ala Pro Val Met Ala Met Lys Tyr Tyr Thr Ser Lys Ile Asn Ser
65                  70                  75                  80
His Glu Asp Leu Glu Asn Leu Thr Thr Tyr Gly Phe Arg Gly Glu Ala
                 85                  90                  95
Leu Gly Ser Ile Cys Cys Ile Ala Glu Val Leu Ile Thr Thr Arg Thr
                100                 105                 110
Ala Ala Asp Asn Phe Ser Thr Gln Tyr Val Leu Asp Gly Ser Gly His
                115                 120                 125
Ile Leu Ser Gln Lys Pro Ser His Leu Gly Gln Gly Thr Thr Val Thr
        130                 135                 140
Ala Leu Arg Leu Phe Lys Asn Leu Pro Val Arg Lys Gln Phe Tyr Ser
145                 150                 155                 160
Thr Ala Lys Lys Cys Lys Asp Glu Ile Lys Lys Ile Gln Asp Leu Leu
                165                 170                 175
Met Ser Phe Gly Ile Leu Lys Pro Asp Leu Arg Ile Val Phe Val His
                180                 185                 190
Asn Lys Ala Val Ile Trp Gln Lys Ser Arg Val Ser Asp His Lys Met
        195                 200                 205
Ala Leu Met Ser Val Leu Gly Thr Ala Val Met Asn Asn Met Glu Ser
210                 215                 220
Phe Gln Tyr His Ser Glu Glu Ser Gln Ile Tyr Leu Ser Gly Phe Leu
225                 230                 235                 240
Pro Lys Cys Asp Ala Asp His Ser Phe Thr Ser Leu Ser Thr Pro Glu
                245                 250                 255
Arg Ser Phe Ile Phe Ile Asn Ser Arg Pro Val His Gln Lys Asp Ile
                260                 265                 270
Leu Lys Leu Ile Arg His His Tyr Asn Leu Lys Cys Leu Lys Glu Ser
        275                 280                 285
Thr Arg Leu Tyr Pro Val Phe Phe Leu Lys Ile Asp Val Pro Thr Ala
    290                 295                 300
Asp Val Asp Val Asn Leu Thr Pro Asp Lys Ser Gln Val Leu Leu Gln
305                 310                 315                 320
Asn Lys Glu Ser Val Leu Ile Ala Leu Glu Asn Leu Met Thr Thr Cys
                325                 330                 335
Tyr Gly Pro Leu Pro Ser Thr Asn Ser Tyr Glu Asn Asn Lys Thr Asp
                340                 345                 350
Val Ser Ala Ala Asp Ile Val Leu Ser Lys Thr Ala Glu Thr Asp Val
        355                 360                 365
Leu Phe Asn Lys Val Glu Ser Ser Gly Lys Asn Tyr Ser Asn Val Asp
    370                 375                 380
Thr Ser Val Ile Pro Phe Gln Asn Asp Met His Asn Asp Glu Ser Gly
385                 390                 395                 400
Lys Asn Thr Asp Asp Cys Leu Asn His Gln Ile Ser Ile Gly Asp Phe
                405                 410                 415
Gly Tyr Gly His Cys Ser Ser Glu Ile Ser Asn Ile Asp Lys Asn Thr
                420                 425                 430
Lys Asn Ala Phe Gln Asp Ile Ser Met Ser Asn Val Ser Trp Glu Asn
        435                 440                 445
```

-continued

```
Ser Gln Thr Glu Tyr Ser Lys Thr Cys Phe Ile Ser Ser Val Lys His
    450                 455                 460
Thr Gln Ser Glu Asn Gly Asn Lys Asp His Ile Asp Glu Ser Gly Glu
465                 470                 475                 480
Asn Glu Glu Glu Ala Gly Leu Glu Asn Ser Ser Glu Ile Ser Ala Asp
                485                 490                 495
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
            515                 520                 525
Ser Asn Asn Tyr Pro Ile Pro Glu Gln Met Asn Leu Asn Glu Asp
    530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
                565                 570                 575
Ala Ser Ala Leu Phe Val Gln Asp His Arg Pro Gln Phe Leu Ile Glu
            580                 585                 590
Asn Pro Lys Thr Ser Leu Glu Asp Ala Thr Leu Gln Ile Glu Glu Leu
            595                 600                 605
Trp Lys Thr Leu Ser Glu Glu Lys Leu Lys Tyr Glu Glu Lys Ala
    610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Lys Ile Lys Pro
                645                 650                 655
Thr Ser Ala Trp Asn Leu Ala Gln Lys His Lys Leu Lys Thr Ser Leu
            660                 665                 670
Ser Asn Gln Pro Lys Leu Asp Glu Leu Leu Gln Ser Gln Ile Glu Lys
            675                 680                 685
Arg Arg Ser Gln Asn Ile Lys Met Val Gln Ile Pro Phe Ser Met Lys
690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
                725                 730                 735
Leu Met Thr Ser Lys Thr Glu Val Met Leu Leu Asn Pro Tyr Arg Val
            740                 745                 750
Glu Glu Ala Leu Leu Phe Lys Arg Leu Leu Glu Asn His Lys Leu Pro
    755                 760                 765
Ala Glu Pro Leu Glu Lys Pro Ile Met Leu Thr Glu Ser Leu Phe Asn
770                 775                 780
Gly Ser His Tyr Leu Asp Val Leu Tyr Lys Met Thr Ala Asp Asp Gln
785                 790                 795                 800
Arg Tyr Ser Gly Ser Thr Tyr Leu Ser Asp Pro Arg Leu Thr Ala Asn
                805                 810                 815
Gly Phe Lys Ile Lys Leu Ile Pro Gly Val Ser Ile Thr Glu Asn Tyr
            820                 825                 830
Leu Glu Ile Glu Gly Met Ala Asn Cys Leu Pro Phe Tyr Gly Val Ala
            835                 840                 845
Asp Leu Lys Glu Ile Leu Asn Ala Ile Leu Asn Arg Asn Ala Lys Glu
850                 855                 860
```

-continued

| | | | | | | | | | | | | |
|---|---|---|---|---|---|---|---|---|---|---|---|---|
| Val | Tyr | Glu | Cys | Arg | Pro | Arg | Lys | Val | Ile | Ser | Tyr | Leu | Glu | Gly | Glu |
| 865 | | | | 870 | | | | 875 | | | | 880 |

Ala Val Arg Leu Ser Arg Gln Leu Pro Met Tyr Leu Ser Lys Glu Asp
            885                 890                 895

Ile Gln Asp Ile Ile Tyr Arg Met Lys His Gln Phe Gly Asn Glu Ile
        900                 905                 910

Lys Glu Cys Val His Gly Arg Pro Phe Phe His His Leu Thr Tyr Leu
    915                 920                 925

Pro Glu Thr Thr
    930

<210> SEQ ID NO 5
<211> LENGTH: 2771
<212> TYPE: DNA
<213> ORGANISM: homo sapiens
<220> FEATURE:
<221> NAME/KEY: CDS
<222> LOCATION: (25)..(2613)

<400> SEQUENCE: 5

```
cgaggcggat cgggtgttgc atcc atg gag cga gct gag agc tcg agt aca         51
                      Met Glu Arg Ala Glu Ser Ser Ser Thr
                        1               5 gaa cct gct aag gcc atc aaa cct att gat cgg aag tca gtc cat cag        99
Glu Pro Ala Lys Ala Ile Lys Pro Ile Asp Arg Lys Ser Val His Gln
 10                  15                  20                  25 att tgc tct ggg cag gtg gta ctg agt cta agc act gcg gta aag gag      147
Ile Cys Ser Gly Gln Val Val Leu Ser Leu Ser Thr Ala Val Lys Glu
                 30                  35                  40 tta gta gaa aac agt ctg gat gct ggt gcc act aat att gat cta aag      195
Leu Val Glu Asn Ser Leu Asp Ala Gly Ala Thr Asn Ile Asp Leu Lys
             45                  50                  55 ctt aag gac tat gga gtg gat ctt att gaa gtt tca gac aat gga tgt      243
Leu Lys Asp Tyr Gly Val Asp Leu Ile Glu Val Ser Asp Asn Gly Cys
         60                  65                  70 ggg gta gaa gaa gaa aac ttc gaa ggc tta act ctg aaa cat cac aca      291
Gly Val Glu Glu Glu Asn Phe Glu Gly Leu Thr Leu Lys His His Thr
     75                  80                  85 tct aag att caa gag ttt gcc gac cta act cag gtt gaa act ttt ggc      339
Ser Lys Ile Gln Glu Phe Ala Asp Leu Thr Gln Val Glu Thr Phe Gly
 90                  95                 100                 105 ttt cgg ggg gaa gct ctg agc tca ctt tgt gca ctg agc gat gtc acc      387
Phe Arg Gly Glu Ala Leu Ser Ser Leu Cys Ala Leu Ser Asp Val Thr
                110                 115                 120 att tct acc tgc cac gca tcg gcg aag gtt gga act cga ctg atg ttt      435
Ile Ser Thr Cys His Ala Ser Ala Lys Val Gly Thr Arg Leu Met Phe
            125                 130                 135 gat cac aat ggg aaa att atc cag aaa acc ccc tac ccc gcc ccc aga      483
Asp His Asn Gly Lys Ile Ile Gln Lys Thr Pro Tyr Pro Arg Pro Arg
        140                 145                 150 ggg acc aca gtc agc gtg cag cag tta ttt tcc aca cta cct gtg cgc      531
Gly Thr Thr Val Ser Val Gln Gln Leu Phe Ser Thr Leu Pro Val Arg
    155                 160                 165 cat aag gaa ttt caa agg aat att aag aag gag tat gcc aaa atg gtc      579
His Lys Glu Phe Gln Arg Asn Ile Lys Lys Glu Tyr Ala Lys Met Val
170                 175                 180                 185 cag gtc tta cat gca tac tgt atc att tca gca ggc atc cgt gta agt      627
Gln Val Leu His Ala Tyr Cys Ile Ile Ser Ala Gly Ile Arg Val Ser
                190                 195                 200
```

-continued

| | |
|---|---|
| tgc acc aat cag ctt gga caa gga aaa cga c ag cct gtg gta tgc aca<br>Cys Thr Asn Gln Leu Gly Gln Gly Lys Arg G ln Pro Val Val Cys Thr<br>              205                  210                  215 | 675 |
| ggt gga agc ccc agc ata aag gaa aat atc g gc tct gtg ttt ggg cag<br>Gly Gly Ser Pro Ser Ile Lys Glu Asn Ile G ly Ser Val Phe Gly Gln<br>              220                  225                  230 | 723 |
| aag cag ttg caa agc ctc att cct ttt gtt c ag ctg ccc cct agt gac<br>Lys Gln Leu Gln Ser Leu Ile Pro Phe Val G ln Leu Pro Pro Ser Asp<br>              235                  240                  245 | 771 |
| tcc gtg tgt gaa gag tac ggt ttg agc tgt t cg gat gct ctg cat aat<br>Ser Val Cys Glu Glu Tyr Gly Leu Ser Cys S er Asp Ala Leu His Asn<br>250                  255                  260                  265 | 819 |
| ctt ttt tac atc tca ggt ttc att tca caa t gc acg cat gga gtt gga<br>Leu Phe Tyr Ile Ser Gly Phe Ile Ser Gln C ys Thr His Gly Val Gly<br>              270                  275                  280 | 867 |
| agg agt tca aca gac aga cag ttt ttc ttt a tc aac cgg cgg cct tgt<br>Arg Ser Ser Thr Asp Arg Gln Phe Phe Phe I le Asn Arg Arg Pro Cys<br>              285                  290                  295 | 915 |
| gac cca gca aag gtc tgc aga ctc gtg aat g ag gtc tac cac atg tat<br>Asp Pro Ala Lys Val Cys Arg Leu Val Asn G lu Val Tyr His Met Tyr<br>              300                  305                  310 | 963 |
| aat cga cac cag tat cca ttt gtt gtt ctt a ac att tct gtt gat tca<br>Asn Arg His Gln Tyr Pro Phe Val Val Leu A sn Ile Ser Val Asp Ser<br>              315                  320                  325 | 1011 |
| gaa tgc gtt gat atc aat gtt act cca gat a aa agg caa att ttg cta<br>Glu Cys Val Asp Ile Asn Val Thr Pro Asp L ys Arg Gln Ile Leu Leu<br>330                  335                  340                  345 | 1059 |
| caa gag gaa aag ctt ttg ttg gca gtt tta a ag acc tct ttg ata gga<br>Gln Glu Glu Lys Leu Leu Leu Ala Val Leu L ys Thr Ser Leu Ile Gly<br>              350                  355                  360 | 1107 |
| atg ttt gat agt gat gtc aac aag cta aat g tc agt cag cag cca ctg<br>Met Phe Asp Ser Asp Val Asn Lys Leu Asn V al Ser Gln Gln Pro Leu<br>              365                  370                  375 | 1155 |
| ctg gat gtt gaa ggt aac tta ata aaa atg c at gca gcg gat ttg gaa<br>Leu Asp Val Glu Gly Asn Leu Ile Lys Met H is Ala Ala Asp Leu Glu<br>              380                  385                  390 | 1203 |
| aag ccc atg gta gaa aag cag gat caa tcc c ct tca tta agg act gga<br>Lys Pro Met Val Glu Lys Gln Asp Gln Ser P ro Ser Leu Arg Thr Gly<br>              395                  400                  405 | 1251 |
| gaa gaa aaa aaa gac gtg tcc att tcc aga c tg cga gag gcc ttt tct<br>Glu Glu Lys Lys Asp Val Ser Ile Ser Arg L eu Arg Glu Ala Phe Ser<br>410                  415                  420                  425 | 1299 |
| ctt cgt cac aca aca gag aac aag cct cac a gc cca aag act cca gaa<br>Leu Arg His Thr Thr Glu Asn Lys Pro His S er Pro Lys Thr Pro Glu<br>              430                  435                  440 | 1347 |
| cca aga agg agc cct cta gga cag aaa agg g gt atg ctg tct tct agc<br>Pro Arg Arg Ser Pro Leu Gly Gln Lys Arg G ly Met Leu Ser Ser Ser<br>              445                  450                  455 | 1395 |
| act tca ggt gcc atc tct gac aaa ggc gtc c tg aga cct cag aaa gag<br>Thr Ser Gly Ala Ile Ser Asp Lys Gly Val L eu Arg Pro Gln Lys Glu<br>              460                  465                  470 | 1443 |
| gca gtg agt tcc agt cac gga ccc agt gac c ct acg gac aga gcg gag<br>Ala Val Ser Ser Ser His Gly Pro Ser Asp P ro Thr Asp Arg Ala Glu<br>              475                  480                  485 | 1491 |
| gtg gag aag gac tcg ggg cac ggc agc act t cc gtg gat tct gag ggg<br>Val Glu Lys Asp Ser Gly His Gly Ser Thr S er Val Asp Ser Glu Gly<br>490                  495                  500                  505 | 1539 |
| ttc agc atc cca gac acg ggc agt cac tgc a gc agc gag tat gcg gcc<br>Phe Ser Ile Pro Asp Thr Gly Ser His Cys S er Ser Glu Tyr Ala Ala<br>              510                  515                  520 | 1587 |

```
                                                    -continued agc tcc cca ggg gac agg ggc tcg cag gaa c at gtg gac tct cag gag    1635
Ser Ser Pro Gly Asp Arg Gly Ser Gln Glu H is Val Asp Ser Gln Glu
            525                 530                 535 aaa gcg cct gaa act gac gac tct ttt tca g at gtg gac tgc cat tca    1683
Lys Ala Pro Glu Thr Asp Asp Ser Phe Ser A sp Val Asp Cys His Ser
        540                 545                 550 aac cag gaa gat acc gga tgt aaa ttt cga g tt ttg cct cag cca act    1731
Asn Gln Glu Asp Thr Gly Cys Lys Phe Arg V al Leu Pro Gln Pro Thr
555                 560                 565 aat ctc gca acc cca aac aca aag cgt ttt a aa aaa gaa gaa att ctt    1779
Asn Leu Ala Thr Pro Asn Thr Lys Arg Phe L ys Lys Glu Glu Ile Leu
570                 575                 580                 585 tcc agt tct gac att tgt caa aag tta gta a at act cag gac atg tca    1827
Ser Ser Ser Asp Ile Cys Gln Lys Leu Val A sn Thr Gln Asp Met Ser
                590                 595                 600 gcc tct cag gtt gat gta gct gtg aaa att a at aag aaa gtt gtg ccc    1875
Ala Ser Gln Val Asp Val Ala Val Lys Ile A sn Lys Lys Val Val Pro
            605                 610                 615 ctg gac ttt tct atg agt tct tta gct aaa c ga ata aag cag tta cat    1923
Leu Asp Phe Ser Met Ser Ser Leu Ala Lys A rg Ile Lys Gln Leu His
        620                 625                 630 cat gaa gca cag caa agt gaa ggg gaa cag a at tac agg aag ttt agg    1971
His Glu Ala Gln Gln Ser Glu Gly Glu Gln A sn Tyr Arg Lys Phe Arg
    635                 640                 645 gca aag att tgt cct gga gaa aat caa gca g cc gaa gat gaa cta aga    2019
Ala Lys Ile Cys Pro Gly Glu Asn Gln Ala A la Glu Asp Glu Leu Arg
650                 655                 660                 665 aaa gag ata agt aaa acg atg ttt gca gaa a tg gaa atc att ggt cag    2067
Lys Glu Ile Ser Lys Thr Met Phe Ala Glu M et Glu Ile Ile Gly Gln
                670                 675                 680 ttt aac ctg gga ttt ata ata acc aaa ctg a at gag gat atc ttc ata    2115
Phe Asn Leu Gly Phe Ile Ile Thr Lys Leu A sn Glu Asp Ile Phe Ile
            685                 690                 695 gtg gac cag cat gcc acg gac gag aag tat a ac ttc gag atg ctg cag    2163
Val Asp Gln His Ala Thr Asp Glu Lys Tyr A sn Phe Glu Met Leu Gln
        700                 705                 710 cag cac acc gtg ctc cag ggg cag agg ctc a ta gca cct cag act ctc    2211
Gln His Thr Val Leu Gln Gly Gln Arg Leu I le Ala Pro Gln Thr Leu
    715                 720                 725 aac tta act gct gtt aat gaa gct gtt ctg a ta gaa aat ctg gaa ata    2259
Asn Leu Thr Ala Val Asn Glu Ala Val Leu I le Glu Asn Leu Glu Ile
730                 735                 740                 745 ttt aga aag aat ggc ttt gat ttt gtt atc g at gaa aat gct cca gtc    2307
Phe Arg Lys Asn Gly Phe Asp Phe Val Ile A sp Glu Asn Ala Pro Val
                750                 755                 760 act gaa agg gct aaa ctg att tcc ttg cca a ct agt aaa aac tgg acc    2355
Thr Glu Arg Ala Lys Leu Ile Ser Leu Pro T hr Ser Lys Asn Trp Thr
            765                 770                 775 ttc gga ccc cag gac gtc gat gaa ctg atc t tc atg ctg agc gac agc    2403
Phe Gly Pro Gln Asp Val Asp Glu Leu Ile P he Met Leu Ser Asp Ser
        780                 785                 790 cct ggg gtc atg tgc cgg cct tcc cga gtc a ag cag atg ttt gcc tcc    2451
Pro Gly Val Met Cys Arg Pro Ser Arg Val L ys Gln Met Phe Ala Ser
    795                 800                 805 aga gcc tgc cgg aag tcg gtg atg att ggg a ct gct ctt aac aca agc    2499
Arg Ala Cys Arg Lys Ser Val Met Ile Gly T hr Ala Leu Asn Thr Ser
810                 815                 820                 825 gag atg aag aaa ctg atc acc cac atg ggg g ag atg gac cac ccc tgg    2547
Glu Met Lys Lys Leu Ile Thr His Met Gly G lu Met Asp His Pro Trp
                830                 835                 840
```

```
aac tgt ccc cat gga agg cca acc atg aga c ac atc gcc aac ctg ggt    2595
Asn Cys Pro His Gly Arg Pro Thr Met Arg H is Ile Ala Asn Leu Gly
            845                 850                 855 gtc att tct cag aac tga ccgtagtcac tgtatggaat a attggtttt           2643
Val Ile Ser Gln Asn
        860 atcgcagatt tttatgtttt gaaagacaga gtcttcacta accttttttg t tttaaaatg  2703 aaacctgcta cttaaaaaaa atacacatca cacccattta aaagtgatct t gagaacctt  2763 ttcaaacc                                                            2771

<210> SEQ ID NO 6
<211> LENGTH: 862
<212> TYPE: PRT
<213> ORGANISM: homo sapiens

<400> SEQUENCE: 6

Met Glu Arg Ala Glu Ser Ser Thr Glu P ro Ala Lys Ala Ile Lys
1               5                   10                  15

Pro Ile Asp Arg Lys Ser Val His Gln Ile C ys Ser Gly Gln Val Val
            20                  25                  30

Leu Ser Leu Ser Thr Ala Val Lys Glu Leu V al Glu Asn Ser Leu Asp
        35                  40                  45

Ala Gly Ala Thr Asn Ile Asp Leu Lys Leu L ys Asp Tyr Gly Val Asp
    50                  55                  60

Leu Ile Glu Val Ser Asp Asn Gly Cys Gly V al Glu Glu Asn Phe
65                  70                  75                  80

Glu Gly Leu Thr Leu Lys His His Thr Ser L ys Ile Gln Glu Phe Ala
                85                  90                  95

Asp Leu Thr Gln Val Glu Thr Phe Gly Phe A rg Gly Glu Ala Leu Ser
            100                 105                 110

Ser Leu Cys Ala Leu Ser Asp Val Thr Ile S er Thr Cys His Ala Ser
        115                 120                 125

Ala Lys Val Gly Thr Arg Leu Met Phe Asp H is Asn Gly Lys Ile Ile
    130                 135                 140

Gln Lys Thr Pro Tyr Pro Arg Pro Arg Gly T hr Thr Val Ser Val Gln
145                 150                 155                 160

Gln Leu Phe Ser Thr Leu Pro Val Arg His L ys Glu Phe Gln Arg Asn
                165                 170                 175

Ile Lys Lys Glu Tyr Ala Lys Met Val Gln V al Leu His Ala Tyr Cys
            180                 185                 190

Ile Ile Ser Ala Gly Ile Arg Val Ser Cys T hr Asn Gln Leu Gly Gln
        195                 200                 205

Gly Lys Arg Gln Pro Val Val Cys Thr Gly G ly Ser Pro Ser Ile Lys
    210                 215                 220

Glu Asn Ile Gly Ser Val Phe Gly Gln Lys G ln Leu Gln Ser Leu Ile
225                 230                 235                 240

Pro Phe Val Gln Leu Pro Pro Ser Asp Ser V al Cys Glu Glu Tyr Gly
                245                 250                 255

Leu Ser Cys Ser Asp Ala Leu His Asn Leu P he Tyr Ile Ser Gly Phe
            260                 265                 270

Ile Ser Gln Cys Thr His Gly Val Gly Arg S er Ser Thr Asp Arg Gln
        275                 280                 285

Phe Phe Phe Ile Asn Arg Arg Pro Cys Asp P ro Ala Lys Val Cys Arg
    290                 295                 300
```

-continued

```
Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
            325                 330                 335

Thr Pro Asp Lys Arg Gln Ile Leu Leu Gln Glu Lys Leu Leu Leu
            340                 345                 350

Ala Val Leu Lys Thr Ser Leu Ile Gly Met Phe Asp Ser Asp Val Asn
        355                 360                 365

Lys Leu Asn Val Ser Gln Gln Pro Leu Leu Asp Val Glu Gly Asn Leu
370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
            405                 410                 415

Ile Ser Arg Leu Arg Glu Ala Phe Ser Leu Arg His Thr Thr Glu Asn
        420                 425                 430

Lys Pro His Ser Pro Lys Thr Pro Glu Pro Arg Arg Ser Pro Leu Gly
        435                 440                 445

Gln Lys Arg Gly Met Leu Ser Ser Ser Thr Ser Gly Ala Ile Ser Asp
450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
            485                 490                 495

Gly Ser Thr Ser Val Asp Ser Glu Gly Phe Ser Ile Pro Asp Thr Gly
        500                 505                 510

Ser His Cys Ser Ser Glu Tyr Ala Ala Ser Ser Pro Gly Asp Arg Gly
    515                 520                 525

Ser Gln Glu His Val Asp Ser Gln Glu Lys Ala Pro Glu Thr Asp Asp
530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
            565                 570                 575

Lys Arg Phe Lys Lys Glu Glu Ile Leu Ser Ser Ser Asp Ile Cys Gln
        580                 585                 590

Lys Leu Val Asn Thr Gln Asp Met Ser Ala Ser Gln Val Asp Val Ala
        595                 600                 605

Val Lys Ile Asn Lys Lys Val Val Pro Leu Asp Phe Ser Met Ser Ser
610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
            645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
        675                 680                 685

Thr Lys Leu Asn Glu Asp Ile Phe Ile Val Asp Gln His Ala Thr Asp
        690                 695                 700

Glu Lys Tyr Asn Phe Glu Met Leu Gln Gln His Thr Val Leu Gln Gly
705                 710                 715                 720
```

```
Gln Arg Leu Ile Ala Pro Gln Thr Leu Asn Leu Thr Ala Val Asn Glu
            725                 730                 735
Ala Val Leu Ile Glu Asn Leu Glu Ile Phe Arg Lys Asn Gly Phe Asp
            740                 745                 750
Phe Val Ile Asp Glu Asn Ala Pro Val Thr Glu Arg Ala Lys Leu Ile
            755                 760                 765
Ser Leu Pro Thr Ser Lys Asn Trp Thr Phe Gly Pro Gln Asp Val Asp
            770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                805                 810                 815
Met Ile Gly Thr Ala Leu Asn Thr Ser Glu Met Lys Lys Leu Ile Thr
            820                 825                 830
His Met Gly Glu Met Asp His Pro Trp Asn Cys Pro His Gly Arg Pro
            835                 840                 845
Thr Met Arg His Ile Ala Asn Leu Gly Val Ile Ser Gln Asn
        850                 855                 860

<210> SEQ ID NO 7
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 7
gttgaacatc tagacgtctc                                              20

<210> SEQ ID NO 8
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 8
tcgtggcagg ggttattcg                                               19

<210> SEQ ID NO 9
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 9
ctacccaatg cctcaaccg                                               19

<210> SEQ ID NO 10
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 10
gagaactgat agaaattgga tg                                           22

<210> SEQ ID NO 11
<211> LENGTH: 18
<212> TYPE: DNA
```

```
<213> ORGANISM: Artificial Sequence
<220> FEATURE:
<223> OTHER INFORMATION: hMLH1 sense primer

<400> SEQUENCE: 11
gggacatgag gttctccg                                                 18

<210> SEQ ID NO 12
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 12
gggctgtgtg aatcctcag                                                19

<210> SEQ ID NO 13
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 13
cggttcacca ctgtctcgtc                                               20

<210> SEQ ID NO 14
<211> LENGTH: 18
<212> TYPE: DNA
<213> ORGANISM: Artificial Sequence
<220> FEATURE:
<223> OTHER INFORMATION: hMLH1 antisense primer

<400> SEQUENCE: 14
tccaggatgc tctcctcg                                                 18

<210> SEQ ID NO 15
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 15
caagtcctgg tagcaaagtc                                               20

<210> SEQ ID NO 16
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 16
atggcaaggt caaagagcg                                                19

<210> SEQ ID NO 17
<211> LENGTH: 22
<212> TYPE: DNA
<213> ORGANISM: Artificial Sequence
<220> FEATURE:
<223> OTHER INFORMATION: hMLH1 antisense primer
<221> NAME/KEY: misc_feature
<222> LOCATION: (22)..(22)
<223> OTHER INFORMATION: n equals a, t, g or c
```

```
<400> SEQUENCE: 17
caacaatgta ttcagnaagt cc                                        22

<210> SEQ ID NO 18
<211> LENGTH: 21
<212> TYPE: DNA
<213> ORGANISM: Artificial Sequence
<220> FEATURE:
<223> OTHER INFORMATION: hMLH1 antisense primer

<400> SEQUENCE: 18
ttgatacaac actttgtatc g                                         21

<210> SEQ ID NO 19
<211> LENGTH: 21
<212> TYPE: DNA
<213> ORGANISM: Artificial Sequence
<220> FEATURE:
<223> OTHER INFORMATION: hMLH1 antisense primer

<400> SEQUENCE: 19
ggaatactat cagaaggcaa g                                         21

<210> SEQ ID NO 20
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 20
acagagcaag ttactcagat g                                         21

<210> SEQ ID NO 21
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 21
gtacacaatg caggcattag                                           20

<210> SEQ ID NO 22
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 22
aatgtggatg ttaatgtgca c                                         21

<210> SEQ ID NO 23
<211> LENGTH: 18
<212> TYPE: DNA
<213> ORGANISM: Artificial Sequence
<220> FEATURE:
<223> OTHER INFORMATION: hMLH1 sense primer

<400> SEQUENCE: 23
ctgacctcgt cttcctac                                             18

<210> SEQ ID NO 24
<211> LENGTH: 19
```

```
<212> TYPE: DNA
<213> ORGANISM: Artificial Sequence
<220> FEATURE:
<223> OTHER INFORMATION: hMLH1 sense primer

<400> SEQUENCE: 24
cagcaagatg aggagatgc                                                19

<210> SEQ ID NO 25
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 25
ggaaatggtg aagatgatt c                                              21

<210> SEQ ID NO 26
<211> LENGTH: 16
<212> TYPE: DNA
<213> ORGANISM: Artificial Sequence
<220> FEATURE:
<223> OTHER INFORMATION: hMLH1 sense primer

<400> SEQUENCE: 26
cttctcaaca ccaagc                                                   16

<210> SEQ ID NO 27
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 27
gaaattgatg aggaagggaa c                                             21

<210> SEQ ID NO 28
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 28
cttctgattg acaactatgt gc                                            22

<210> SEQ ID NO 29
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 29
cacagaagat ggaaatatcc tg                                            22

<210> SEQ ID NO 30
<211> LENGTH: 20
<212> TYPE: DNA
<213> ORGANISM: Artificial Sequence
<220> FEATURE:
<223> OTHER INFORMATION: hMLH1 sense primer
```

```
<400> SEQUENCE: 30
gtgttggtag cacttaagac                                              20

<210> SEQ ID NO 31
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 31
tttcccatat tcttcacttg                                              20

<210> SEQ ID NO 32
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 32
gtaacatgag ccacatggc                                               19

<210> SEQ ID NO 33
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 33
ccactgtctc gtccagccg                                               19

<210> SEQ ID NO 34
<211> LENGTH: 26
<212> TYPE: DNA
<213> ORGANISM: Artificial Sequence
<220> FEATURE:
<223> OTHER INFORMATION: hMLH1 5' primer wit h BamHI restriction site

<400> SEQUENCE: 34
cgggatccat gtcgttcgtg gcaggg                                       26

<210> SEQ ID NO 35
<211> LENGTH: 26
<212> TYPE: DNA
<213> ORGANISM: Artificial Sequence
<220> FEATURE:
<223> OTHER INFORMATION: hMLH1 3' primer wit h XbaI restriction site

<400> SEQUENCE: 35
gctctagatt aacacctctc aaagac                                       26

<210> SEQ ID NO 36
<211> LENGTH: 21
<212> TYPE: DNA
<213> ORGANISM: Artificial Sequence
<220> FEATURE:
<223> OTHER INFORMATION: hMLH1 primer useful fo r amplifying codons 1
      to 394

<400> SEQUENCE: 36
gcatctagac gtttccttgg c                                            21
```

<210> SEQ ID NO 37
<211> LENGTH: 20
<212> TYPE: DNA
<213> ORGANISM: Artificial Sequence
<220> FEATURE:
<223> OTHER INFORMATION: primer useful for ampl ifying codons 1 to
      394 of hMLH1

<400> SEQUENCE: 37
catccaagct tctgttcccg                                              20

<210> SEQ ID NO 38
<211> LENGTH: 19
<212> TYPE: DNA
<213> ORGANISM: Artificial Sequence
<220> FEATURE:
<223> OTHER INFORMATION: primer useful for ampl ifying codons 326 to
      729 of hMLH1

<400> SEQUENCE: 38
ggggtgcagc agcacatcg                                               19

<210> SEQ ID NO 39
<211> LENGTH: 20
<212> TYPE: DNA
<213> ORGANISM: Artificial Sequence
<220> FEATURE:
<223> OTHER INFORMATION: primer useful for ampl ifying codons 326 to
      729 of hMLH1

<400> SEQUENCE: 39
ggaggcagaa tgtgtgagcg                                              20

<210> SEQ ID NO 40
<211> LENGTH: 19
<212> TYPE: DNA
<213> ORGANISM: Artificial Sequence
<220> FEATURE:
<223> OTHER INFORMATION: primer useful for ampl ifying codons 602 to
      756 plus 128 nucleotides of 3' untranslated sequence of hMLH1

<400> SEQUENCE: 40
 tcccaaagaa ggacttgct                                              19

<210> SEQ ID NO 41
<211> LENGTH: 22
<212> TYPE: DNA
<213> ORGANISM: Artificial Sequence
<220> FEATURE:
<223> OTHER INFORMATION: primer useful for ampl ifying codons 602 to
      756 plus 128 nucleotides of 3' untranslated sequence of hMLH1

<400> SEQUENCE: 41
agtataagtc ttaagtgcta cc                                           22

<210> SEQ ID NO 42
<211> LENGTH: 20
<212> TYPE: DNA
<213> ORGANISM: Artificial Sequence
<220> FEATURE:
<223> OTHER INFORMATION: primer useful for ampl ifying codons 578 to 632
      of hMLH1

<400> SEQUENCE: 42
tttatggttt ctcacctgcc                                              20

<210> SEQ ID NO 43
<211> LENGTH: 19

```
<212> TYPE: DNA
<213> ORGANISM: Artificial Sequence
<220> FEATURE:
<223> OTHER INFORMATION: primer useful for amplifying codons 578 to 632
      of hMLH1

<400> SEQUENCE: 43
gttatctgcc cacctcagc                                              19

<210> SEQ ID NO 44
<211> LENGTH: 59
<212> TYPE: DNA
<213> ORGANISM: Artificial Sequence
<220> FEATURE:
<223> OTHER INFORMATION: primer useful for amplifying codons 1 to 394
      of hMLH1 wherein PCR product may be used for coupled
      transcription-translation

<400> SEQUENCE: 44
ggatcctaat acgactcact atagggagac caccatggca tctagacgtt t cccttggc     59

<210> SEQ ID NO 45
<211> LENGTH: 20
<212> TYPE: DNA
<213> ORGANISM: Artificial Sequence
<220> FEATURE:
<223> OTHER INFORMATION: primer useful for amplifying codons 1 to 394
      of hMLH1 wherein PCR product may be used for coupled
      transcription-translation

<400> SEQUENCE: 45
catccaagct tctgttcccg                                             20

<210> SEQ ID NO 46
<211> LENGTH: 56
<212> TYPE: DNA
<213> ORGANISM: Artificial Sequence
<220> FEATURE:
<223> OTHER INFORMATION: primer useful for amplifying codons 326 to
      729 of hMLH1 wherein PCR product may be used for coupled
      transcription-translation

<400> SEQUENCE: 46
ggatcctaat acgactcact atagggagac caccatgggg gtgcagcagc a catcg        56

<210> SEQ ID NO 47
<211> LENGTH: 20
<212> TYPE: DNA
<213> ORGANISM: Artificial Sequence
<220> FEATURE:
<223> OTHER INFORMATION: primer useful for amplifying codons 326 to
      729 of hMLH1 wherein PCR product may be used for coupled
      transcription-translation

<400> SEQUENCE: 47
ggaggcagaa tgtgtgagcg                                             20

<210> SEQ ID NO 48
<211> LENGTH: 28
<212> TYPE: DNA
<213> ORGANISM: Artificial Sequence
<220> FEATURE:
<223> OTHER INFORMATION: hMLH2 5' primer with a BamHI restriction site

<400> SEQUENCE: 48
cgggatccat gaaacaattg cctgcggc                                    28
```

<210> SEQ ID NO 49
<211> LENGTH: 26
<212> TYPE: DNA
<213> ORGANISM: Artificial Sequence
<220> FEATURE:
<223> OTHER INFORMATION: hMLH2 3' primer wit h XbaI restriction site

<400> SEQUENCE: 49
gctctagacc agactcatgc tgtttt                                    26

<210> SEQ ID NO 50
<211> LENGTH: 26
<212> TYPE: DNA
<213> ORGANISM: Artificial Sequence
<220> FEATURE:
<223> OTHER INFORMATION: hMLH3 5' primer wit h a BamHI restriction site

<400> SEQUENCE: 50
cgggatccat ggagcgagct gagagc                                    26

<210> SEQ ID NO 51
<211> LENGTH: 23
<212> TYPE: DNA
<213> ORGANISM: Artificial Sequence
<220> FEATURE:
<223> OTHER INFORMATION: hMLH3 3' primer wit h XbaI restriction site

<400> SEQUENCE: 51
gctctagagt gaagactctg tct                                       23

<210> SEQ ID NO 52
<211> LENGTH: 20
<212> TYPE: DNA
<213> ORGANISM: Artificial Sequence
<220> FEATURE:
<223> OTHER INFORMATION: hMLH2 primer

<400> SEQUENCE: 52
aagctgctct gttaaaagcg                                           20

<210> SEQ ID NO 53
<211> LENGTH: 18
<212> TYPE: DNA
<213> ORGANISM: Artificial Sequence
<220> FEATURE:
<223> OTHER INFORMATION: hMLH2 primer

<400> SEQUENCE: 53
gcaccagcat ccaaggag                                             18

<210> SEQ ID NO 54
<211> LENGTH: 19
<212> TYPE: DNA
<213> ORGANISM: Artificial Sequence
<220> FEATURE:
<223> OTHER INFORMATION: hMLH3 primer

<400> SEQUENCE: 54
caaccatgag acacatcgc                                            19

<210> SEQ ID NO 55
<211> LENGTH: 20
<212> TYPE: DNA
<213> ORGANISM: Artificial Sequence
<220> FEATURE:
<223> OTHER INFORMATION: hMLH3 primer
<210> SEQ ID NO 55
<211> LENGTH: 20
<212> TYPE: DNA
<213> ORGANISM: Artificial Sequence
<220> FEATURE:
<223> OTHER INFORMATION: primer useful for amplifying codons 1 to 500 of hMLH2

<400> SEQUENCE: 55
aggttagtga agactctgtc                                              20

<210> SEQ ID NO 56
<211> LENGTH: 53
<212> TYPE: DNA
<213> ORGANISM: Artificial Sequence
<220> FEATURE:
<223> OTHER INFORMATION: primer useful for amplifying codons 1 to 500 of hMLH2

<400> SEQUENCE: 56
ggatcctaat acgactcact atagggagac caccatggaa caattgcctg c gg        53

<210> SEQ ID NO 57
<211> LENGTH: 18
<212> TYPE: DNA
<213> ORGANISM: Artificial Sequence
<220> FEATURE:
<223> OTHER INFORMATION: primer useful for amplifying codons 1 to 500 of hMLH2

<400> SEQUENCE: 57
cctgctccac tcatctgc                                                18

<210> SEQ ID NO 58
<211> LENGTH: 60
<212> TYPE: DNA
<213> ORGANISM: Artificial Sequence
<220> FEATURE:
<223> OTHER INFORMATION: primer useful for amplifying codons 270 to 755 of hMLH2

<400> SEQUENCE: 58
ggatcctaat acgactcact atagggagac caccatggaa gatatcttaa a gttaatccg 60

<210> SEQ ID NO 59
<211> LENGTH: 21
<212> TYPE: DNA
<213> ORGANISM: Artificial Sequence
<220> FEATURE:
<223> OTHER INFORMATION: primer useful for amplifying codons 270 to 755 of hMLH2

<400> SEQUENCE: 59
ggcttcttct actctatatg g                                            21

<210> SEQ ID NO 60
<211> LENGTH: 58
<212> TYPE: DNA
<213> ORGANISM: Artificial Sequence
<220> FEATURE:
<223> OTHER INFORMATION: primer useful for amplifying from codon 485 to the translation termination site at codon 933 of hMLH2

<400> SEQUENCE: 60
ggatcctaat acgactcact atagggagac caccatggca ggtcttgaaa a ctcttcg   58

<210> SEQ ID NO 61
<211> LENGTH: 21
<212> TYPE: DNA
<213> ORGANISM: Artificial Sequence
<220> FEATURE:
<223> OTHER INFORMATION: primer useful for amplifying from codon 485 to the translation termination site at codon 933 of hMLH2

```
<400> SEQUENCE: 61
aaaacaagtc agtgaatcct c                                              21

<210> SEQ ID NO 62
<211> LENGTH: 20
<212> TYPE: DNA
<213> ORGANISM: Artificial Sequence
<220> FEATURE:
<223> OTHER INFORMATION: 3' primer useful fo r amplifying up to codon
      369 of hMLH2

<400> SEQUENCE: 62
aagcacatct gtttctgctg                                                20

<210> SEQ ID NO 63
<211> LENGTH: 20
<212> TYPE: DNA
<213> ORGANISM: Artificial Sequence
<220> FEATURE:
<223> OTHER INFORMATION: 3' primer useful fo r amplifying up to codon
      290 of hMLH2

<400> SEQUENCE: 63
acgagtagat tcctttaggc                                                20

<210> SEQ ID NO 64
<211> LENGTH: 19
<212> TYPE: DNA
<213> ORGANISM: Artificial Sequence
<220> FEATURE:
<223> OTHER INFORMATION: 3' primer useful fo r amplifying up to codon
      214 of hMLH2

<400> SEQUENCE: 64
cagaactgac atgagagcc                                                 19

<210> SEQ ID NO 65
<211> LENGTH: 52
<212> TYPE: DNA
<213> ORGANISM: Artificial Sequence
<220> FEATURE:
<223> OTHER INFORMATION: primer useful for ampl ifying codons 1 to 863
      hMLH3

<400> SEQUENCE: 65
ggatcctaat acgactcact atagggagac caccatggag cgagctgaga g c           52

<210> SEQ ID NO 66
<211> LENGTH: 20
<212> TYPE: DNA
<213> ORGANISM: Artificial Sequence
<220> FEATURE:
<223> OTHER INFORMATION: primer useful for ampl ifying codons 1 to 863
      hMLH3

<400> SEQUENCE: 66
aggttagtga agactctgtc                                                20

<210> SEQ ID NO 67
<211> LENGTH: 17
<212> TYPE: DNA
<213> ORGANISM: Artificial Sequence
<220> FEATURE:
<223> OTHER INFORMATION: primer useful for ampl ifying up to codon 472
      of hMLH3
```

<210> SEQ ID NO 68
<211> LENGTH: 57
<212> TYPE: DNA
<213> ORGANISM: Artificial Sequence
<220> FEATURE:
<223> OTHER INFORMATION: primer useful for amp1 ifying codons 415 to 863
     of hMLH3

<400> SEQUENCE: 68
ggatcctaat acgactcact atagggagac caccatggtg tccatttcca g actgcg    57

<210> SEQ ID NO 69
<211> LENGTH: 20
<212> TYPE: DNA
<213> ORGANISM: Artificial Sequence
<220> FEATURE:
<223> OTHER INFORMATION: primer useful for amp1 ifying codons 415 to 863
     of hMLH3

<400> SEQUENCE: 69
aggttagtga agactctgtc                                              20

<210> SEQ ID NO 70
<211> LENGTH: 21
<212> TYPE: DNA
<213> ORGANISM: Artificial Sequence
<220> FEATURE:
<223> OTHER INFORMATION: primer useful for amp ifying codons 195 to
     233 of hMLH2

<400> SEQUENCE: 70
ttatttggca gaaaagcaga g                                            21

<210> SEQ ID NO 71
<211> LENGTH: 21
<212> TYPE: DNA
<213> ORGANISM: Artificial Sequence
<220> FEATURE:
<223> OTHER INFORMATION: primer useful for amp ifying codons 195 to 233
     of hMLH2

<400> SEQUENCE: 71
ttaaaagact aacctcttgc c                                            21

<210> SEQ ID NO 72
<211> LENGTH: 21
<212> TYPE: DNA
<213> ORGANISM: Artificial Sequence
<220> FEATURE:
<223> OTHER INFORMATION: sequencing primer useful for sequencing codons
     195 to 233 of hMLH2

<400> SEQUENCE: 72
ctgctgttat gaacaatatg g                                            21

<210> SEQ ID NO 73
<211> LENGTH: 19
<212> TYPE: DNA
<213> ORGANISM: Artificial Sequence
<220> FEATURE:
<223> OTHER INFORMATION: primer useful for amp ifying codons 233 to 257
     of hMLH3

```
<400> SEQUENCE: 73
cagaagcagt tgcaaagcc                                                    19

<210> SEQ ID NO 74
<211> LENGTH: 20
<212> TYPE: DNA
<213> ORGANISM: Artificial Sequence
<220> FEATURE:
<223> OTHER INFORMATION: primer useful for amp1 ifying codons 233 to 257
      of hMLH3

<400> SEQUENCE: 74
aaaccgtact cttcacacac                                                   20

<210> SEQ ID NO 75
<211> LENGTH: 20
<212> TYPE: DNA
<213> ORGANISM: Artificial Sequence
<220> FEATURE:
<223> OTHER INFORMATION: primer useful for amp1 ifying codons 347 of 377
      of hMLH3

<400> SEQUENCE: 75
gaggaaaagc ttttgttggc                                                   20

<210> SEQ ID NO 76
<211> LENGTH: 18
<212> TYPE: DNA
<213> ORGANISM: Artificial Sequence
<220> FEATURE:
<223> OTHER INFORMATION: primer useful for amp1 ifying codons 347 of 377
      of hMLH3

<400> SEQUENCE: 76
cagtggctgc tgactgac                                                     18

<210> SEQ ID NO 77
<211> LENGTH: 19
<212> TYPE: DNA
<213> ORGANISM: Artificial Sequence
<220> FEATURE:
<223> OTHER INFORMATION: primer useful for amp1 ifying codons 439 to 472
      of hMLH3

<400> SEQUENCE: 77
tccagaacca agaaggagc                                                    19

<210> SEQ ID NO 78
<211> LENGTH: 16
<212> TYPE: DNA
<213> ORGANISM: Artificial Sequence
<220> FEATURE:
<223> OTHER INFORMATION: primer useful for amp1 ifying codons 439 to 472
      of hMLH3

<400> SEQUENCE: 78
tgaggtctca gcaggc                                                       16
```